United States Patent [19]

Suzuki et al.

[11] Patent Number: 5,750,349
[45] Date of Patent: May 12, 1998

[54] ANTIBODIES TO β-AMYLOIDS OR THEIR DERIVATIVES AND USE THEREOF

[75] Inventors: Nobuhiro Suzuki; Asano Odaka, both of Ibaraki; Chieko Kitada, Osaka, all of Japan

[73] Assignee: Takeda Chemical Industries Ltd., Osaka, Japan

[21] Appl. No.: 302,808

[22] PCT Filed: Jan. 24, 1994

[86] PCT No.: PCT/JP94/00089

§ 371 Date: Sep. 15, 1994

§ 102(e) Date: Sep. 15, 1994

[87] PCT Pub. No.: WO94/17197

PCT Pub. Date: Aug. 4, 1994

[30] Foreign Application Priority Data

Jan. 25, 1993 [JP] Japan ................. 5-010132
Feb. 5, 1993 [JP] Japan ................. 5-019035
Nov. 16, 1993 [JP] Japan ................. 5-286985
Dec. 28, 1993 [JP] Japan ................. 5-334773

[51] Int. Cl.$^6$ ........................... G01N 33/53
[52] U.S. Cl. ............ 435/7.1; 435/7.92; 435/7.94; 435/7.95; 435/70.21; 435/326; 435/331; 530/387.9; 530/388.1; 530/389.1
[58] Field of Search ................. 435/7.1, 7.92, 435/7.94, 70.21, 240.27, 240.26, 7.95, 331, 326; 436/811; 530/387.9, 388.1, 389.1

[56] References Cited

PUBLICATIONS

Nature, vol. 359, pp. 322-325, 1992.

Seubert et al. "Insolation and quantification of soluble Alzheimers β-peptide from biological fluids", Nature 359:325-327.

Morris et al "The Consortium to Establish a Registry for Alzheimer's Disease (CERAD)". Sep. 1989, Neurology, 39: 1159-1165.

*Primary Examiner*—Paula K. Hutzell
*Assistant Examiner*—Patricia A. Duffy
*Attorney, Agent, or Firm*—David G. Conlin; David S. Resnick; Dike, Bronstein, Roberts & Cushman, LLP

[57] ABSTRACT

According to this invention, antibodies which are useful and novel in that they have binding specificity to β-amyloids or derivatives thereof, namely recognize the N-terminal, the C-terminal or central portions of the β-amyloids, respectively, were obtained. By combining these antibodies, determination methods by which the β-amyloids could be determined sensitively and specifically are provided. These determination methods are useful for diagnosis of diseases to which the β-amyloids or their derivatives are related (for example, Alzheimer's disease), and the antibodies of this invention are useful for the development of preventive-therapeutic compositions for Alzheimer's disease.

9 Claims, 16 Drawing Sheets

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 38 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:1:

| Asp | Ala | Glu | Phe | Arg | His | Asp | Ser | Gly | Tyr | Glu | Val | His | His | Gln | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Val | Phe | Phe | Ala | Glu | Asp | Val | Gly | Ser | Asn | Lys | Gly | Ala | Ile | Ile |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Leu | Met | Val | Gly | Gly |
|-----|-----|-----|-----|-----|-----|
|     |     | 35  |     |     |     |

( 2 ) INFORMATION FOR SEQ ID NO:2:

( i ) SEQUENCE CHARACTERISTICS:
        ( A ) LENGTH: 39 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:2:

| Asp | Ala | Glu | Phe | Arg | His | Asp | Ser | Gly | Tyr | Glu | Val | His | His | Gln | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Val | Phe | Phe | Ala | Glu | Asp | Val | Gly | Ser | Asn | Lys | Gly | Ala | Ile | Ile |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Leu | Met | Val | Gly | Gly | Val |
|-----|-----|-----|-----|-----|-----|-----|
|     |     | 35  |     |     |     |     |

( 2 ) INFORMATION FOR SEQ ID NO:3:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:3:

| Asp | Ala | Glu | Phe | Arg | His | Asp | Ser | Gly | Tyr | Glu | Val | His | His | Gln | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Val | Phe | Phe | Ala | Glu | Asp | Val | Gly | Ser | Asn | Lys | Gly | Ala | Ile | Ile |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Leu | Met | Val | Gly | Gly | Val | Val |
|-----|-----|-----|-----|-----|-----|-----|-----|
|     |     | 35  |     |     |     |     | 40  |

( 2 ) INFORMATION FOR SEQ ID NO:4:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:4:

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile
        35                  40
```

( 2 ) INFORMATION FOR SEQ ID NO:5:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:5:

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

( 2 ) INFORMATION FOR SEQ ID NO:6:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:6:

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
```

( 2 ) INFORMATION FOR SEQ ID NO:7:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:7:

```
Asp Ala Glu Phe Arg His Asp Ser Gly Tyr Glu Val His His Gln Lys
 1               5                  10                  15
Leu Val Phe Phe Ala Glu Asp Val Gly Ser Asn Lys
            20                  25
```

( 2 ) INFORMATION FOR SEQ ID NO:8:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:8:

```
Gly Ser Asn Lys Gly Ala Ile Ile Gly Leu Met
 1               5                  10
```

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:9:

```
Met Val Gly Gly Val Val Ile Ala Thr
 1               5
```

( 2 ) INFORMATION FOR SEQ ID NO:10:

( i ) SEQUENCE CHARACTERISTICS:
  ( A ) LENGTH: 16 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:10:

Asp Ala Glu Phe Arg His Asp Ser Gly Tyr Glu Val His His Gln Lys
1               5                   10                  15

( 2 ) INFORMATION FOR SEQ ID NO:11:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:11:

Leu Val Phe Phe Ala Glu Asp Val Gly Ser Asn Lys
1               5                   10

( 2 ) INFORMATION FOR SEQ ID NO:12:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:12:

Val Phe Phe Ala Glu Asp Val Gly Ser Asn Lys
1               5                   10

( 2 ) INFORMATION FOR SEQ ID NO:13:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: cDNA

```
    ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:13:

ATCCCACTCG CACAGCAGCG CACTC                                                        2 5

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:14:

TGCTGTCCAA CTTCAGAGGC TGCTG                                                        2 5
```

ANTIBODIES TO β-AMYLOIDS OR THEIR DERIVATIVES AND USE THEREOF

TECHNICAL FIELD

The present invention relates to antibodies which are useful and novel in that they have binding specificity to β-amyloids or their derivatives. More particularly, the present invention relates to antibodies useful for the development of assays of β-amyloids or their derivatives based on antigen-antibody reaction, diagnoses of diseases to which β-amyloids or their derivatives are related (for example, Alzheimer's disease), or the development of preventive-therapeutic compositions for Alzheimer's disease.

BACKGROUND ART

Senile dementia caused by Alzheimer's disease has raised a serious social problem, and the early establishment of diagnoses and therapeutic methods of Alzheimer's disease has been desired. As lesion characteristic of the brains of patients with Alzheimer's disease, the excessive formation of senile plaques and neurofibrillary tangles have been known. Of these, one of the main constituents of the senile plaque is a β-amyloid or a derivative thereof.

The β-amyloid is a peptide composed of about 40 amino acids, and is coded in the vicinity of the transmembrane region of an amyloid precursor protein (hereinafter referred to as an APP). Amino acid sequences of the β-amyloids are shown below:

However, assay systems for detecting the β-amyloids easily and with high sensitivity have hitherto been scarcely reported, although deep interest has been expressed in the β-amyloids. The sandwich enzyme immunoassay of the β-amyloids is only reported by P. Seubert et al., [*Nature*, 359, 325–327 (1992)].

The assay system of P. Seubert et al. is reported to have a detection sensitivity of 100 pg/ml, which is not satisfactory. Further, the assay system is reported to react also with a partial peptide consisting of N-terminal 28 residues [hereinafter refereed to as β-amyloid (1–28)]. However, a number of hydrophobic amino acids exist in C-terminal portions of the β-amyloids, β-amyloid (29–39), β-amyloid (29–40), β-amyloid (29–41), β-amyloid (29–42) or β-amyloid (29–43). This C-terminal region is therefore considered to be embedded in a cell membrane, and is assumed to play an important role in aggregation and deposition of peptides. For this reason, it is important to quantify β-amyloids having the C-terminal hydrophobic regions. However, the above-mentioned assay system of P. Seubert et al. does not satisfy the social demands in the specificity and sensitivity.

Usually, antibodies to peptides are prepared by immunizing complexes of the peptides and natural or synthetic polymer carriers. Also in the case of the β-amyloids, the report of P. Seubert et al. described above shows that antibodies reactive to β-amyloid (1–40) can be prepared using N-terminal portions of the β-amyloids which are hydrophilic regions, for example, β-amyloid (1–16), as

---

[β-Amyloid (1–38)] SEQ ID NO: 1

Asp—Ala—Glu—Phe—Arg—His—Asp—Ser—Gly—Tyr—Glu—Val—His—
His—Gln—Lys—Leu—Val—Phe—Phe—Ala—Glu—Asp—Val—Gly—Ser—Asn—
Lys—Gly—Ala—Ile—Ile—Gly—Leu—Met—Val—Gly—Gly
[β-Amyloid (1–39)] SEQ ID NO: 2

Asp—Ala—Glu—Phe—Arg—His—Asp—Ser—Gly—Tyr—Glu—Val—His—
His—Gln—Lys—Leu—Val—Phe—Phe—Ala—Glu—Asp—Val—Gly—Ser—Asn—
Lys—Gly—Ala—Ile—Ile—Gly—Leu—Met—Val—Gly—Gly—Val
[β-Amyloid (1–40)] SEQ ID NO: 3

Asp—Ala—Glu—Phe—Arg—His—Asp—Ser—Gly—Tyr—Glu—Val—His—
His—Gln—Lys—Leu—Val—Phe—Phe—Ala—Glu—Asp—Val—Gly—Ser—Asn—
Lys—Gly—Ala—Ile—Ile—Gly—Leu—Met—Val—Gly—Gly—Val—Val
[β-Amyloid (1–41)] SEQ ID NO: 4

Asp—Ala—Glu—Phe—Arg—His—Asp—Ser—Gly—Tyr—Glu—Val—His—
His—Gln—Lys—Leu—Val—Phe—Phe—Ala—Glu—Asp—Val—Gly—Ser—Asn—
Lys—Gly—Ala—Ile—Ile—Gly—Leu—Met—Val—Gly—Gly—Val—Val—Ile
[β-Amyloid (1–42)] SEQ ID NO: 5

Asp—Ala—Glu—Phe—Arg—His—Asp—Ser—Gly—Tyr—Glu—Val—His—
His—Gln—Lys—Leu—Val—Phe—Phe—Ala—Glu—Asp—Val—Gly—Ser—Asn—
Lys—Gly—Ala—Ile—Ile—Gly—Leu—Met—Val—Gly—Gly—Val—Val—Ile—Ala
[β-Amyloid (1–43)] SEQ ID NO: 6

Asp—Ala—Glu—Phe—Arg—His—Asp—Ser—Gly—Tyr—Glu—Val—His—
His—Gln—Lys—Leu—Val—Phe—Phe—Ala—Glu—Asp—Val—Gly—Ser—Asn—
Lys—Gly—Ala—Ile—Ile—Gly—Leu—Met—Val—Gly—Gly—Val—Val—Ile—
Ala—Thr

---

According to recent reports, some of the patients with familial Alzheimer's disease belong to families having point mutations on APP, and the possibility has been pointed out that the β-amyloids are one of the causative substances for Alzheimer's disease. Based on such a background, the β-amyloids have been intensively studied as a main subject for the investigation of Alzheimer's disease, and various results of the studies have been presented.

immunogens. However, it is not clear whether or not an antibody to the C-terminal portion of the β-amyloid which is the hydrophobic region embedded in the cell membrane can be prepared by usual methods. Further, even if the antibody to such a region can be obtained, it does not provide an assurance at all that it reacts with the β-amyloid. Furthermore, if the antibody only shows an extremely low affinity for the β-amyloid, it is generally difficult to expect that, for example, the above-mentioned sandwich enzyme immunoassay of P. Seubert et al. can be established with the antibody. Namely, although various antibodies have hitherto been prepared for the purpose of detecting the β-amyloids, there is no report that the antibody to the C-terminal portion of the β-amyloid has been prepared and applied to the sandwich enzyme immunoassay, thereby developing an immunoassay by which the β-amyloid can be detected with high sensitivity and specificity without cross reaction with β-amyloid (1–28). It is further reported that β-amyloid (25–35) has homology to tachykinin in its amino acid sequence, and has cytotoxicity [B. A. Yankner et al., *Science*, 250, 279–282 (1990)]. However, there is no report at all that an antibody to β-amyloid (25–35) has been prepared and applied to the sandwich enzyme immunoassay, thereby developing an immunoassay by which the β-amyloid can be detected with high sensitivity and specificity without cross reaction with β-amyloid (1–28).

Recently, it is further reported that, of the β-amyloids, β-amyloid (1–42) is mainly deposited in the cerebral cortex (senile plaques), whereas β-amyloid (1–40) is mainly deposited in the cerebral blood vessel (angiopathy) [*Arch. Biochem. Biophys.*, 301, 41–53 (1993)]. It is further suggested that the seed formation of C-terminal portion-containing peptides such as β-amyloid (1–42), β-amyloid (26–42), β-amyloid (26–43) and β-amyloid (34–42) causes the deposition of water-soluble β-amyloid (1–40) [*Biochemistry*, 32, 4693–4697 (1993)]. From such reports, the difference in the deposition manner between β-amyloid (1–40) and β-amyloid (1–42) is considered to be largely related to Alzheimer's disease. When Alzheimer's disease is diagnosed, therefore, sensitive and discriminative determination of β-amyloid (1–40) and β-amyloid (1–42) is important. However, suitable antibodies for this purpose have not been reported yet.

An object of the present invention is to provide a novel antibody which can sensitively, specifically determine a β-amyloid having a C-terminal hydrophobic region or a derivative thereof, preferably a monoclonal antibody. Another object of the present invention is to provide a method for assaying a β-amyloid or a derivative thereof with the antibody.

DISCLOSURE OF INVENTION

In order to solve the above-mentioned problem, the present inventors have conducted intensive investigations. As a result, the present inventors have prepared a plurality of monoclonal antibodies which recognize different portions of β-amyloids or derivatives thereof and developed an excellent method for assaying β-amyloids by the use of the antibodies, followed by further investigations, thus completing the present invention.

That is, the present invention provides an antibody (preferably a monoclonal antibody) specifically reactive to a partial peptide on the C-terminal side of a β-amyloid or a derivative thereof; a monoclonal antibody specifically reactive to a partial peptide on the N-terminal side of a β-amyloid or a derivative thereof; an antibody (preferably a monoclonal antibody) specifically reactive to a partial peptide in a central portion of a β-amyloid or a derivative thereof; a hybridoma cell producing the monoclonal antibody; methods for producing the antibody and the hybridoma cell; and an immunoassay for a β-amyloid or a derivative thereof by a competitive method or a sandwich method using the antibody (a method for diagnosing Alzheimer's disease, etc.).

More particularly, the present inventors have prepared a plurality of monoclonal antibodies using β-amyloid (25–35), β-amyloid (35–43), β-amyloid (1–40) and β-amyloid (1–16) as immunogens. By combination of the antibodies, the present inventors developed an immunoassay by which β-amyloids or derivatives thereof can be detected with high sensitivity and specificity without cross reaction with β-amyloid (1–28). Namely, using β-amyloid (25–35), β-amyloid (35–43) and β-amyloid (1–40) as immunogens, the present inventors have established monoclonal antibodies which recognize C-terminal portions of β-amyloids or derivatives thereof, for example, antibodies designated BA-27a, BS-85a and BC-05a. Of these, BS-85a and BA-27a each only show an extremely low affinity for the β-amyloids in a competitive immunoassay using labeled β-amyloids. Nevertheless, studies have revealed that combinations of them with two kinds of antibodies selected from monoclonal antibodies to an N-terminal portion (β-amyloid (1–16)) of the β-amyloids, namely antibodies designated BAN-052a and BAN-50a, can provide a sandwich immunoassay with extremely high sensitivity to the β-amyloids. Further, the present inventors have shown that a sandwich immunoassay in which BC-05a is combined with BAN-50a detects the β-amyloids with high sensitivity in a formic acid extract from the brain of a patient with Alzheimer's disease without cross reaction with β-amyloid (1–40). Furthermore, the present inventors have established monoclonal antibodies which recognize partial peptides in central portions of β-amyloids or derivatives thereof, for example, the antibody designated BP-90a.

One of the major features of the present invention is to provide sandwich immunoassays which allow highly sensitive and discriminative determination of β-amyloid (1–40) and β-amyloid (1–42). Namely, the sandwich immunoassay in which BA-27a is combined with BAN-052a or BAN-50a can detect β-amyloid (1–40), but can not detect β-amyloid (1–42). Further, the sandwich immunoassay in which BC-05a is combined with BAN-052a or BAN-50a can detect β-amyloid (1–42), but can not detect β-amyloid (1–40). Furthermore, the sandwich immunoassay in which BS-85a is combined with BAN-052a or BAN-50a can detect β-amyloid (1–40) and β-amyloid (1–42). Therefore, according to the sandwich immunoassays in which the monoclonal antibodies of the present invention are combined, highly sensitive and discriminative quantification of β-amyloid (1–40) and β-amyloid (1–42) can be conducted. Such a technique is a surprising finding which can not be deduced from the prior art.

More specifically, the present invention provides:

(1) An antibody specifically reactive to a partial peptide on the C-terminal side of a β-amyloid or a derivative thereof;

(2) The antibody described in (1), in which said antibody does not recognize a partial peptide having an amino acid sequence represented by SEQ ID NO:8 and a partial peptide having an amino acid sequence represented by SEQ ID NO:9;

(3) The antibody described in (1), in which said antibody recognizes a partial peptide having an amino acid sequence represented by SEQ ID NO:8, but does not recognize a partial peptide having an amino acid sequence represented by SEQ ID NO:9;

(4) The antibody described in (1), in which said antibody does not recognize a partial peptide having an amino acid sequence represented by SEQ ID NO:8, but recognizes a partial peptide having an amino acid sequence represented by SEQ ID NO:9;

(5) The antibody described in any one of (1) to (4), in which said antibody is a monoclonal antibody;

(6) A hybridoma cell producing the monoclonal antibody described in (5);

(7) A monoclonal antibody indicated by BAN-052a and specifically reactive to a partial peptide on the N-terminal side of a β-amyloid or a derivative thereof, in which said antibody recognizes a partial peptide having an amino acid sequence represented by SEQ ID NO:7 and/or a partial peptide having an amino acid sequence represented by SEQ ID NO:10;

(8) A monoclonal antibody indicated by BAN-50a and specifically reactive to a partial peptide on the N-terminal side of a β-amyloid or a derivative thereof, in which said antibody recognizes a partial peptide having an amino acid sequence represented by SEQ ID NO:7 and/or a partial peptide having an amino acid sequence represented by SEQ ID NO:10;

(9) A hybridoma cell producing the monoclonal antibody described in (7);

(10) A hybridoma cell producing the monoclonal antibody described in (8);

(11) An antibody specifically reactive to a β-amyloid or a derivative thereof, in which said antibody does not recognize a partial peptide having an amino acid sequence represented by SEQ ID NO:7, but recognizes a partial peptide having an amino acid sequence represented by SEQ ID NO:12;

(12) The antibody described in (11), in which said antibody is a monoclonal antibody;

(13) A hybridoma cell producing the monoclonal antibody described in (12);

(14) A method for determining a β-amyloid or a derivative thereof in a test solution which comprises using the antibody described in (1), (7), (8) or (11);

(15) A method for determining a β-amyloid in a test solution which comprises using the antibody described in (1) and the antibody described in (7) or (8);

(16) A method for determining a β-amyloid in a test solution which comprises using the antibody described in (11) and the antibody described in (1), (7) or (8); and

(17) The method described in any one of (14) to (16), in which said method is used for diagnosis of Alzheimer's disease.

Preferred embodiments of (1) described above are as follows:

(18) The antibody described in (1), in which said β-amyloid is a peptide having an amino acid sequence represented by SEQ ID NO:1, SEQ ID NO:2, SEQ ID NO:3, SEQ ID NO:4, SEQ ID NO:5 or SEQ ID NO:6;

(19) The antibody described in (1), in which said derivative of the β-amyloid is a peptide having an amino acid sequence consisting of the 2nd to the 42nd amino acids of an amino acid sequence represented by SEQ ID NO:5, a peptide having an amino acid sequence consisting of the 3rd to the 42nd amino acids of the amino acid sequence represented by SEQ ID NO:5, the N-terminal glutamic acid being substituted by pyroglutamic acid, a peptide having an amino acid sequence consisting of the 4th to the 42nd amino acids of the amino acid sequence represented by SEQ ID NO:5, or a peptide having an amino acid sequence lacking the 1st to the 16th amino acids or the 1st to the 17th amino acids from an amino acid sequence represented by any one of SEQ ID NO:1 to SEQ ID NO:6;

(20) The antibody described in (1), in which the partial peptide on the C-terminal side of the β-amyloid or the derivative thereof is a partial peptide having an amino acid sequence beginning from the 25th or later amino acid from the N-terminal amino acid of the β-amyloid;

(21) The antibody described in (1), (18) to (20), in which said antibody does not recognize a partial peptide having an amino acid sequence represented by SEQ ID NO:7;

(22) The antibody described in (1), (18) to (21), in which said antibody recognizes a partial peptide having an amino acid sequence represented by SEQ ID NO:8; and

(23) The antibody described in (1), (18) to (21), in which said antibody recognizes a partial peptide having an amino acid sequence represented by SEQ ID NO:9.

Preferred embodiments of (2) described above are as follows:

(24) An antibody specifically reactive to a partial peptide on the C-terminal side of a β-amyloid having an amino acid sequence represented by SEQ ID NO:1, a β-amyloid having an amino acid sequence represented by SEQ ID NO:2 and/or a β-amyloid having an amino acid sequence represented by SEQ ID NO:3, in which said antibody does not recognize a partial peptide having an amino acid sequence represented by SEQ ID NO:8 and/or a partial peptide having an amino acid sequence represented by SEQ ID NO:9; and

(25) The antibody described in (24), in which said antibody recognizes a partial peptide having an amino acid sequence represented by SEQ ID NO:5.

A preferred embodiment of (3) described above is as follows:

(26) An antibody specifically reactive to a partial peptide on the C-terminal side of a β-amyloid having an amino acid sequence represented by SEQ ID NO:1, a β-amyloid having an amino acid sequence represented by SEQ ID NO:2, a β-amyloid having an amino acid sequence represented by SEQ ID NO:3 and/or a β-amyloid having an amino acid sequence represented by SEQ ID NO:5, in which said antibody recognizes a partial peptide having an amino acid sequence represented by SEQ ID NO:8, but does not recognize a partial peptide having an amino acid sequence represented by SEQ ID NO:9.

Preferred embodiments of (4) described above are as follows:

(27) An antibody specifically reactive to a β-amyloid or a derivative thereof contained in a formic acid extract from the brain of a patient with Alzheimer's disease, in which said antibody does not recognize a partial peptide having an amino acid sequence represented by SEQ ID NO:8, but recognizes a partial peptide having an amino acid sequence represented by SEQ ID NO:9;

(28) The antibody described in (27), in which said β-amyloid or said derivative thereof contained in the formic acid extract from the brain of the patient with Alzheimer's disease is a β-amyloid having an amino acid sequence represented by SEQ ID NO:5; and

(29) The antibody described in (28), in which said antibody does not recognize a β-amyloid having an amino acid sequence represented by SEQ ID NO:1, a β-amyloid having an amino acid sequence represented by SEQ ID NO:2 and a β-amyloid having an amino acid sequence represented by SEQ ID NO:3.

Preferred embodiments of (5) described above are as follows:

(30) The monoclonal antibody described in (24) or (25), in which said antibody is indicated by BA-27a;

(31) The monoclonal antibody described in (26), in which said antibody is indicated by BS-85a; and

(32) The monoclonal antibody described in (27) to (29), in which said antibody is indicated by BC-05a.

Particularly preferred is

(33) The antibody described in any one of (1) to (5) and (18) to (32), in which said antibody is used for determination of a β-amyloid or a derivative thereof by a sandwich enzyme immunoassay.

Preferred embodiments of (6) described above are as follows:

(34) A hybridoma cell producing the monoclonal antibody described in (30);

(35) A hybridoma cell producing the monoclonal antibody described in (31); and

(36) A hybridoma cell producing the monoclonal antibody described in (32).

Preferred embodiments of (7) and (8) described above are as follows:

(37) The monoclonal antibody described in (7) or (8), in which said β-amyloid is a peptide having an amino acid sequence represented by SEQ ID NO:1, SEQ ID NO:2, SEQ ID NO:3, SEQ ID NO:4, SEQ ID NO:5 or SEQ ID NO:6;

(38) The monoclonal antibody described in (7) or (8), in which said derivative of the β-amyloid is a peptide having an amino acid sequence consisting of the 2nd to the 42nd amino acids of an amino acid sequence represented by SEQ ID NO:5, a peptide having an amino acid sequence consisting of the 3rd to the 42nd amino acids of the amino acid sequence represented by SEQ ID NO:5, and whose N-terminal glutamic acid being substituted by pyroglutamic acid, or a peptide having an amino acid sequence consisting of the 4th to the 42nd amino acids of the amino acid sequence represented by SEQ ID NO:5; and

(39) The antibody described in any one of (7), (8), (37) or (38), in which said antibody is used for determination of a β-amyloid or a derivative thereof by a sandwich enzyme immunoassay.

Preferred embodiments of (11) described above are as follows:

(40) The antibody described in (11), in which said β-amyloid is a peptide having an amino acid sequence represented by SEQ ID NO:1, SEQ ID NO:2, SEQ ID NO:3, SEQ ID NO:4, SEQ ID NO:5 or SEQ ID NO:6;

(41) The antibody described in (11), in which said derivative of the β-amyloid is a peptide having an amino acid sequence consisting of the 2nd to the 42nd amino acids of an amino acid sequence represented by SEQ ID NO:5, a peptide having an amino acid sequence consisting of the 3rd to the 42nd amino acids of the amino acid sequence represented by SEQ ID NO:5, and whose N-terminal glutamic acid being substituted by pyroglutamic acid, a peptide having an amino acid sequence consisting of the 4th to the 42nd amino acids of the amino acid sequence represented by SEQ ID NO:5, or a peptide having an amino acid sequence lacking the 1st to the 16th amino acids or the 1st to the 17th amino acids from an amino acid sequence represented by any one of SEQ ID NO:1 to SEQ ID NO:6;

(42) The antibody described in (11), in which said β-amyloid or said derivative thereof is a peptide having an amino acid sequence lacking the 1st to the 16th amino acids or the 1st to the 17th amino acids from an amino acid sequence represented by any one of SEQ ID NO:1 to SEQ ID NO:6;

(43) The antibody described in (11), in which said β-amyloid or said derivative thereof is a peptide having an amino acid sequence lacking the 1st to the 16th amino acids or the 1st to the 17th amino acids from an amino acid sequence represented by SEQ ID NO:3;

(44) The antibody described in (11), (40) or (43), in which said antibody recognizes a peptide having an amino acid sequence represented by SEQ ID NO:11; and

(45) The antibody described in (11), (40) or (43), in which said antibody is used for determination of a β-amyloid or a derivative thereof by a sandwich enzyme immunoassay.

A preferred embodiment of (12) described above is as follows:

(46) The monoclonal antibody described in (12), in which said antibody is indicated by BP-90a.

A preferred embodiment of (13) described above is as follows:

(47) A hybridoma cell producing the monoclonal antibody described in (46).

A preferred embodiment of (14) described above is as follows:

(48) A method for determining a β-amyloid or a derivative thereof in a test solution which comprises competitively reacting the antibody described in (1), (7), (8) or (11) with the test solution and a labeled β-amyloid or a derivative thereof, and measuring the ratio of the labeled β-amyloid or the derivative thereof bound to said antibody.

Preferred embodiments of (15) described above are as follows:

(49) A method for determining a β-amyloid or a derivative thereof in a test solution which comprises reacting an antibody to a β-amyloid or a derivative thereof insolubilized on a carrier, a labeled antibody to a β-amyloid or a derivative thereof and the test solution with one another, and then, measuring the activity of a labeling agent on the carrier, one of the antibody to the β-amyloid or the derivative thereof insolubilized on the carrier and the labeled antibody to the β-amyloid or the derivative thereof being the antibody described in (1), and the other being an antibody which recognizes a partial peptide having an amino acid sequence represented by SEQ ID NO:7 or SEQ ID NO:10;

(50) The determining method described in (49), in which the antibody which recognizes the partial peptide having the amino acid sequence represented by SEQ ID NO:7 or SEQ ID NO:10 is a monoclonal antibody indicated by BAN-052a or BAN-50a;

(51) The determining method described in (49), in which one of the antibody to the β-amyloid insolubilized on the carrier and the labeled antibody to the β-amyloid is a monoclonal antibody indicated by BA-27a, BS-85a or BC-05a, and the other is a monoclonal antibody indicated by BAN-052a or BAN-50a;

(52) The determining method described in (49), in which one of the antibody to the β-amyloid insolubilized on the carrier and the labeled antibody to the β-amyloid is a monoclonal antibody indicated by BA-27a, the other is a monoclonal antibody indicated by BAN-052a or BAN-50a, and the β-amyloid or the derivative thereof is a peptide having an amino acid sequence represented by SEQ ID NO:1, a peptide having an amino acid sequence represented by SEQ ID NO:2, a peptide having an amino acid sequence represented by SEQ ID NO:3 and/or a peptide having an amino acid sequence represented by SEQ ID NO:5;

(53) The determining method described in (49), in which one of the antibody to the β-amyloid insolubilized on the carrier and the labeled antibody to the β-amyloid is a monoclonal antibody indicated by BS-85a, the other is a monoclonal antibody indicated by BAN-052a or BAN-50a, and the β-amyloid or the derivative thereof is a peptide having an amino acid sequence represented by SEQ ID NO:1, a peptide having an amino acid sequence represented by SEQ ID NO:2, a peptide having an amino acid sequence represented by SEQ ID NO:3 and/or a peptide having an amino acid sequence represented by SEQ ID NO:5; and

(54) The determining method described in (49), in which one of the antibody to the β-amyloid insolubilized on the carrier and the labeled antibody to the β-amyloid is a monoclonal antibody indicated by BC-05a, the other is a monoclonal antibody indicated by BAN-052a or BAN-50a, and the β-amyloid or the derivative thereof is a peptide having an amino acid sequence represented by SEQ ID NO:5.

Preferred embodiments of (16) described above are as follows:

(55) A method for determining a β-amyloid or a derivative thereof in a test solution which comprises reacting an antibody to a β-amyloid or a derivative thereof insolubilized on a carrier, a labled antibody to a β-amyloid or a derivative thereof and the test solution with one another, and then, measuring the activity of a labeling agent on the carrier, one of the antibody to the β-amyloid or the derivative thereof insolubilized on the carrier and the labled antibody to the β-amyloid or the derivative thereof being the antibody described in (11), and the other being the antibody described in (1) or an antibody which recognizes a partial peptide having an amino acid sequence represented by SEQ ID NO:7 or SEQ ID NO:10;

(56) The determining method described in (55), in which the antibody which recognizes the partial peptide having the amino acid sequence represented by SEQ ID NO:7 or SEQ ID NO:10 is a monoclonal antibody indicated by BAN-052a or BAN-50a;

(57) The determining method described in (55), in which one of the antibody to the β-amyloid insolubilized on the carrier and the labled antibody to the β-amyloid is a monoclonal antibody indicated by BP-90a, and the other is a monoclonal antibody indicated by BA-27a, BS-85a, BC-05a, BAN-052a or BAN-50a;

(58) The determining method described in (55), in which one of the antibody to the β-amyloid insolubilized on the carrier and the labeled antibody to the β-amyloid is a monoclonal antibody indicated by BP-90a, the other is a monoclonal antibody indicated by BAN-052a or BAN-50a, and the β-amyloid or the derivative thereof is a peptide having an amino acid sequence represented by SEQ ID NO:1, a peptide having an amino acid sequence represented by SEQ ID NO:2, a peptide having an amino acid sequence represented by SEQ ID NO:3, a peptide having an amino acid sequence represented by SEQ ID NO:4, a peptide having an amino acid sequence represented by SEQ ID NO:5 and/or a peptide having an amino acid sequence represented by SEQ ID NO:6; and

(59) The determining method described in (55), in which one of the antibody to the β-amyloid insolubilized on the carrier and the labeled antibody to the β-amyloid is a monoclonal antibody indicated by BP-90a, the other is a monoclonal antibody indicated by BA-27a, BS-85a or BC-05a, and the β-amyloid or the derivative thereof is a peptide having an amino acid sequence lacking the 1st to the 16th amino acids or the 1st to the 17th amino acids from an amino acid sequence represented by any one of SEQ ID NO:1 to SEQ ID NO:6.

Of the anti-β-amyloid antibody-producing hybridomas obtained by the present invention, BAN-052, BA-27 and BS-85 were deposited with the Institute for Fermentation, Osaka, Japan (IFO) under the following accession numbers on Dec. 22, 1992, and with the National Institute of Bioscience and Human-technology, the Agency of Industrial Science and Technology, the Ministry of International Trade and Industry, Japan (NIBH) under the following accession numbers on Jan. 7, 1993.

| Hybridoma | IFO | FERM-BP (NIBH) |
| --- | --- | --- |
| BAN-052 | 50386 | 4138 |
| BA-27 | 50387 | 4139 |
| BS-85 | 50388 | 4140 |

Further, of the hybridoma cells obtained by the present invention, BAN-50 was deposited with the Institute for Fermentation, Osaka, Japan (IFO) under the following accession number on Jan. 8, 1993, and with the National Institute of Bioscience and Human-technology, the Agency of Industrial Science and Technology, the Ministry of International Trade and Industry, Japan (NIBH) under the following accession number on Jan. 27, 1993.

| Hybridoma | IFO | FERM-BP (NIBH) |
| --- | --- | --- |
| BAN-50 | 50390 | 4163 |

Furthermore, of the hybridoma cells obtained by the present invention, BC-05 and BP-90 were deposited with the National Institute of Bioscience and Human-technology, the Agency of Industrial Science and Technology, the Ministry of International Trade and Industry, Japan (NIBH) under the following accession numbers on Nov. 2, 1993.

| Hybridoma | FERM-BP (NIBH) |
| --- | --- |
| BC-05 | 4457 |
| BP-90 | 4458 |

The antibody obtained from each hybridomas represented by attaching the suffix "a" to the hybridoma name.

Of the SEQ ID NOs used in this specification, SEQ ID NO:1 to SEQ ID NO:12 indicate amino acid sequences of the following peptides:

[SEQ ID NO:1] β-Amyloid (1–38)
[SEQ ID NO:2] β-Amyloid (1–39)
[SEQ ID NO:3] β-Amyloid (1–40)
[SEQ ID NO:4] β-Amyloid (1–41)
[SEQ ID NO:5] β-Amyloid (1–42)
[SEQ ID NO:6] β-Amyloid (1–43)
[SEQ ID NO:7] β-Amyloid (1–28)
[SEQ ID NO:8] β-Amyloid (25–35)
[SEQ ID NO:9] β-Amyloid (35–43)
[SEQ ID NO:10] β-Amyloid (1–16)
[SEQ ID NO:11] β-Amyloid (17–28)
[SEQ ID NO:12] β-Amyloid (18–28)

The β-amyloids used in the present invention include β-amyloid (1–38) having the amino acid sequence represented by SEQ ID NO:1, β-amyloid (1–39) having the amino acid sequence represented by SEQ ID NO:2, β-amyloid (1–40) having the amino acid sequence represented by SEQ ID NO:3, β-amyloid (1–41) having the amino acid sequence represented by SEQ ID NO:4, β-amyloid (1–42) having the amino acid sequence represented by SEQ ID NO:5, and β-amyloid (1–43) having the amino acid sequence represented by SEQ ID NO:6.

The derivatives of the β-amyloids used in the present invention include peptides each lacking about 1 to 17 amino acid residues from the N-terminal portions of the above-mentioned β-amyloids, peptides in which L-aspartic acid of the above-mentioned β-amyloids is isomerized to L-isoaspartic acid, D-isoaspartic acid or D-aspartic acid, and peptides in which the N-terminal portions of the above-mentioned β-amyloids have pyroglutamic acid. Examples thereof include the peptide having the amino acid sequence consisting of the 2nd to the 42nd amino acids of the amino acid sequence represented by SEQ ID NO:5, the peptide having the amino acid sequence consisting of the 3rd to the 42nd amino acids of the amino acid sequence represented by SEQ ID NO:5 and the N-terminal glutamic acid being substituted by pyroglutamic acid, the peptide having the amino acid sequence consisting of the 4th to the 42nd amino acids of the amino acid sequence represented by SEQ ID NO:5, and the peptide having the amino acid sequence lacking the 1st to the 16th amino acids or the 1st to the 17th amino acids from the amino acid sequence represented by any one of SEQ ID NO:1 to SEQ ID NO:6 (for example, β-amyloid (17–40) or β-amyloid (18–40)). These β-amyloids or the derivatives thereof can be prepared, for example, from mammals such as humans, monkeys, rats and mice by methods which are per se known, and may also be purified natural samples which are commercially available.

Examples of the partial peptides on the C-terminal sides of the β-amyloids or the derivatives thereof include the partial peptides having the amino acid sequences each beginning from the 25th or later amino acids from the N-terminal amino acids of the β-amyloids.

Examples of the antibodies (preferably the monoclonal antibodies) specifically reactive to the partial peptides on the C-terminal sides of the β-amyloids or the derivatives thereof include the antibodies which recognize the partial peptides or the derivatives thereof, but do not recognize the partial peptide having the amino acid sequence represented by SEQ ID NO:7 (namely, the partial peptide on the N-terminal sides of the β-amyloids, which is represented by β-amyloid (1–28) ). More specifically, of these antibodies, the following antibodies are preferred:

(i) The antibodies which do not recognize the partial peptides each having the amino acid sequences represented by SEQ ID NO:8 and SEQ ID NO:9 (namely, β-amyloid (25–35) and β-amyloid (35–43));

(ii) The antibodies which recognize the partial peptide having the amino acid sequences represented by SEQ ID NO:8 (namely, β-amyloid (25–35)), and more preferably the antibodies which recognize the partial peptide having the amino acid sequence represented by SEQ ID NO:8 (namely β-amyloid (25–35)), but do not recognize the partial peptide having the amino acid sequence represented by SEQ ID NO:9 (namely β-amyloid (35–43)); and (iii) The antibodies which recognize the partial peptide having the amino acid sequences represented by SEQ ID NO:9 (namely, β-amyloid (35–43)), and more preferably the antibodies which do not recognize the partial peptide having the amino acid sequence represented by SEQ ID NO:8 (namely β-amyloid (25–35)), but recognize the partial peptide having the amino acid sequence represented by SEQ ID NO:9 (namely β-amyloid (35–43)).

Of the antibodies of (i) described above, the antibodies are preferred which particularly recognize β-amyloid (1–38) having the amino acid sequence represented by SEQ ID NO:1, β-amyloid (1–39) having the amino acid sequence represented by SEQ ID NO:2 and/or β-amyloid (1–40) having the amino acid sequence represented by SEQ ID NO:3. Further, the antibodies are preferred which recognize β-amyloid (1–38) having the amino acid sequence represented by SEQ ID NO:1, β-amyloid (1–39) having the amino acid sequence represented by SEQ ID NO:2, β-amyloid (1–40) having the amino acid sequence represented by SEQ ID NO:3 and β-amyloid (1–42) having the amino acid sequence represented by SEQ ID NO:5.

Of the antibodies of (ii) described above, the antibodies are preferred which particularly recognize β-amyloid (1–38) having the amino acid sequence represented by SEQ ID NO:1, β-amyloid (1–39) having the amino acid sequence represented by SEQ ID NO:2, β-amyloid (1–40) having the amino acid sequence represented by SEQ ID NO:3 and/or β-amyloid (1–42) having the amino acid sequence represented by SEQ ID NO:5.

Further, of the antibodies of (iii) described above, the antibodies are preferred which particularly recognize the β-amyloids contained in the formic acid extracts from the brains of the patients with Alzheimer's disease (particularly, β-amyloid (1–42) having the amino acid sequence represented by SEQ ID NO:5). Furthermore, the antibodies are preferred which recognize β-amyloid (1–42) having the amino acid sequence represented by SEQ ID NO:5, but do not recognize β-amyloid (1–38) having the amino acid sequence represented by SEQ ID NO:1, β-amyloid (1–39) having the amino acid sequence represented by SEQ ID NO:2 and β-amyloid (1–40) having the amino acid sequence represented by SEQ ID NO:3.

Typical examples of the antibodies of (i) described above include the monoclonal antibody indicated by BA-27a, typical examples of the antibodies of (ii) described above include the monoclonal antibody indicated by BS-85a, and typical examples of the antibodies of (iii) described above include the monoclonal antibodies indicated by BC-05a, BC-15a, BC-65a, BC-75a and BC-55a (particularly, BC-05a is preferred).

Then, the monoclonal antibodies specifically reactive to the partial peptides on the N-terminal sides of the β-amyloids or the derivatives thereof used in the present invention include, for example, the monoclonal antibodies which recognize the partial peptide having the amino acid sequence represented by SEQ ID NO:7 (β-amyloid (1–28)) and/or the partial peptide having the amino acid sequence represented by SEQ ID NO:10 (β-amyloid (1–16)). Specifically, the monoclonal antibodies indicated by BAN-50a, BAN-052a, BAN-11a, BAN-30a, BAN-20a and BAN-40a are shown, and particularly, the monoclonal antibodies indicated by BAN-052a and BAN-50a are preferred.

Further, the monoclonal antibodies specifically reactive to the partial peptides in the central portions of the β-amyloids or the derivatives thereof used in the present invention include, for example, the antibodies (preferably, the monoclonal antibodies) which do not recognize the partial peptide having the amino acid sequence represented by SEQ ID NO:7 and recognize the partial peptide having the amino acid sequence represented by SEQ ID NO:12. Of these antibodies, the antibodies are preferred which particularly recognize the peptides having the amino acid sequences each lacking the 1st to the 16th amino acids or the 1st to the 17th amino acids from the amino acid sequences represented by any one of SEQ ID NO:1 to SEQ ID NO:.6. In particular, the antibodies are preferred which particularly recognize the peptide having the amino acid sequence lacking the 1st to the 16th amino acids from the amino acid sequence represented by SEQ ID NO:3 (the amino acid sequence of SEQ ID NO:11) or the peptide having the amino acid sequence lacking the 1st to the 17th amino acids therefrom (the amino acid sequence of SEQ ID NO:12). Specifically, the monoclonal antibodies indicated by BP-01a, BP-02a, BP-03a and BP-90a are used. Of these monoclonal antibodies, BP-03a and BP-90a can also recognize the partial peptide having the amino acid sequence indicated by SEQ ID NO:11. Of these monoclonal antibodies, BP-90a is particularly suitable.

Methods of preparing the antigens and methods of preparing the monoclonal antibodies are explained below in detail.

(1) Preparation of Antigens

As antigens used for preparing the antibodies of the present invention, for example, any of the β-amyloids or the derivatives thereof, partial peptides obtained by hydrolyzing the β-amyloids or the derivatives thereof and synthetic peptides having one or more kinds of antigenic determinants which are the same as those of the β-amyloids can be used (these are hereinafter also briefly referred to as β-amyloid antigens).

As the β-amyloids or the derivatives thereof, the above-mentioned ones are used. These β-amyloids or the derivatives thereof can be prepared, for example, from mammals such as humans, monkeys, rats and mice by methods which are per se known, and may also be purified natural samples which are commercially available.

Examples of the partial peptides obtained by hydrolyzing the β-amyloids include partial peptides obtained by hydrolyzing β-amyloid (1–43) having the amino acid sequence represented by SEQ ID NO:6 successively from the N-terminus and/or the C-terminus with exoproteases such as aminopeptidase and carboxypeptidase or mixtures thereof, and partial peptides obtained by hydrolyzing β-amyloid (1–43) with various endopeptidases or mixtures thereof. When β-amyloid (1–42) is prepared by this method, the sample is contaminated with β-amyloid (1–41) and/or β-amyloid (1–43) in some cases.

Examples of the synthetic peptides used in the present invention include peptides having the same structure as the above-mentioned purified natural β-amyloid antigens, and peptides having one or more kinds of amino acid sequences which are the same as those of any portions consisting of at least 3 amino acids, preferably at least 6 amino acids in the amino acid sequences of β-amyloid (1–43), etc. (hereinafter briefly referred to as β-amyloid-relating synthetic peptides).

The above-mentioned synthetic peptides can be produced by methods known in the art, which may be either solid phase synthesis methods or liquid phase synthesis methods. Examples of such methods for peptide synthesis include methods described in B. Merrifield, *J. Am. Chem. Soc.*, 85, 2149 (1963); M. Bodanszky and M. A. Ondetti, *Peptide Synthesis*, Interscience Publishers, New York (1966); Schroder and Lubke, *The Peptide*, Academic Press, New York, (1965); N. Izumiya et al., *Peptide Gosei no Kiso to Jikken (Fundamentals and Experiments of Peptide Synthesis)*, Maruzen (1985); and H. Yazima and S. Sakakibara, *Seikaqaku Jikken Koza* 1 (*Course of Biochemical Experiments* 1), *Chemistry of Proteins IV*, 205 (1977). For example, when the β-amyloids or the β-amyloid-relating synthetic peptides are synthesized by the solid methods, any resins known in the art as insoluble resins (such as chloromethyl resins and 4-oxymethylphenylacetamidomethyl resins) are used for a successive condensation of protected amino acids to the C-terminal sides of the β-amyloids or the β-amyloid-relating synthetic peptides according to usual methods. Then, all the protective groups are removed by hydrogen fluoride treatment, followed by purification by methods which are per se known, such as high performance liquid chromatography. Thus, the desired β-amyloids or β-amyloid-relating synthetic peptides can be obtained.

N-protected amino acids can be produced by the methods of protecting the a-amino-groups with Boc groups; further, for example, the hydroxyl groups of serine and threonine with Bzl groups; the ω-carboxylic acid groups of glutamic acid and aspartic acid with OBzl groups; the ε-amino group of lysine with a Cl-Z group; the guanido group of arginine with a Tos group; and the imidazole group of histidine with a Bom group.

When amino acids and so on are indicated by abbreviations in the specification of this invention, the abbreviations adopted by the IUPAC-IUB Commission on Biochemical Nomenclature or commonly used in the art are employed. For example, the following abbreviations are used. When the amino acids are capable of existing as optical isomers, it is understood that the L-forms are represented unless otherwise specified.

PAM: Phenylacetamidomethyl
Boc: t-Butyloxycarbonyl
Cl-Z: 2-Chloro-benzyloxycarbonyl
Br-Z: 2-Bromo-benzyloxycarbonyl
Bzl: Benzyl
OcHex: Cyclohexyl ester
OBzl: Benzyl ester
Tos: p-Toluenesulfonyl
HOBt: 1-Benzotriazole
MeBzl: 4-Methylbenzyl
Bom: Benzyloxymethyl
DCC: N,N'-Dicyclohexylcarbodiimide
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine Because the β-amyloid antigens aggregate easily, insolubilized ones can also be directly immunized. Further, complexes in which the β-amyloid antigens are bound to or adsorbed by appropriate carriers may also be immunized. For the carriers and the mixing ratio of the carriers to the β-amyloid antigens (haptens), the antigens may be bound to or adsorbed by any carriers at any ratio, as long as antibodies effectively raised to the β-amyloid antigens bound to or adsorbed by the carriers. Complexes can be used in which the hapten antigens are bound to or adsorbed by natural or synthetic polymer carriers which are usually used in preparing antibodies to the hapten antigens at a weight ratio of 0.1–100 based on 1 of hapten. The natural polymer carriers include, for example, serum albumin of mammals such as bovine, rabbits and human, thyroglobulin of mammals such as bovine and rabbits, hemoglobin of mammals such as bovine, rabbits, human and sheep, and keyhole limpet hemocyanin. Examples of the synthetic polymer carriers which can be used include various latexes of polymers or copolymers such as amino acid polymers, styrene polymers, acrylic polymers, vinyl polymers and propylene polymers.

In addition, various condensing agents can be used for coupling of the haptens and the carriers. Examples of the condensation agents which are conveniently used include diazonium compounds such as bis-diazotized benzidine which crosslinks tyrosine, histidine and tryptophan; dialdehyde compounds such as glutaraldehyde which crosslinks amino groups together; diisocyanate compounds such as toluene-2,4-diisocyanate; dimaleimide compounds such as N,N'-o-phenylenedimaleimide which crosslinks thiol groups together; maleimide active ester compounds which crosslink amino groups and thiol groups; and carbodiimide compounds crosslinking amino groups and carboxyl groups. When amino groups are crosslinked together, there is another way in which an active ester reagent (for example, SPDP) having a dithiopyridyl group is reacted with one amino acid, followed by reduction to introduce a thiol group, whereas a maleimide group is introduced into the other amino group by the use of a maleimide active ester reagent, and then, both can be reacted with each other.

(2) Preparation of Monoclonal Antibodies

The β-amyloid antigens are given alone or together with carriers and diluents to warm-blooded animals at antibody-producible sites, for example, by intraperitoneal, intravenous and subcutaneous injections. When the β-amyloid antigens are given, Freund's complete adjuvant or Freund's incomplete adjuvant may be given to enhance antibody producing ability. The dosing is usually carried out once every 2 to 6 weeks, totally 2 to 10 times. The warm-blooded animals include, for example, monkeys, rabbits, dogs, guinea pigs, mice, rats, sheep, goat and chickens. For preparation of the monoclonal antibodies, mice and rats are preferably used.

In preparing the monoclonal antibodies, individuals showing a high antibody titer are selected from the warm-blooded animals, for example, mice, immunized with the β-amyloid antigens. After 2 to 5 days from the final immunization, the spleens or the lymph nodes are collected therefrom, and antibody-producing cells contained therein are fused with myeloma cells, whereby anti-β-amyloid monoclonal antibody-producing hybridomas can be prepared. The anti-β-amyloid antibody titer in the serum is determined, for example, by reacting a labeled β-amyloid described below with an antiserum, and then assaying the activity of an labeling agent bound to the antibody. The fusing procedure can be conducted according to methods known in the art, for example, the method of Kohler and Milstein [*Nature*, 256, 495 (1975)]. Fusion accelerators, including polyethylene glycol (PEG) and Sendai virus, may be used. In particular, PEG is preferably used. Examples of the myeloma cells include NS-1, P3U1, SP2/0 and AP-1, and P3U1 is preferably used. The ratio of the antibody-producing cells (spleen cells) to be used to the myeloma cells is preferably about 1:1 to 20:1. PEG (preferably PEG 1,000 to PEG 6,000) can be added in a concentration of about 10 to 80%, followed by incubation at 20° to 40° C., preferably 30 to 37° C., for 1 to 10 minutes, thereby effectively performing cell fusion.

Various methods can be used for screening the anti-β-amyloid antibody-producing hybridomas. Examples of such methods include a method comprising adding a hybridoma culture supernatant to a solid phase (for example, a microplate) by which a β-amyloid or a β-amyloid-relating synthetic peptide is allowed to be adsorbed directly or together with a carrier, and then, adding an anti-immunoglobulin antibody (when a mouse cell is used for cell fusion, an anti-mouse immunoglobulin antibody is used) or protein A labeled with a radioactive material or an enzyme to detect an anti-β-amyloid monoclonal antibody bound to the solid phase; and a method comprising adding a hybridoma culture supernatant to a solid phase by which an anti-immunoglobulin antibody or Protein A is allowed to be adsorbed, and adding a β-amyloid labeled with a radioactive material or an enzyme to detect an anti-β-amyloid monoclonal antibody bound to the solid phase. Selection and breeding of the anti-β-amyloid monoclonal antibody are usually conducted in a medium for animal cells supplemented with 10–20% fetal calf serum (for example, RPMI 1640), to which HAT (hypoxanthine, aminopterin and thymidine) is added. The antibody titer of the hybridoma culture supernatant can be assayed in a manner similar to the above-mentioned assay of the anti-β-amyloid monoclonal antibody in the anti-serum.

Separation and purification of the anti-β-amyloid monoclonal antibodies are carried out similarly to usual separation and purification of polyclonal antibodies according to separating and purifying methods of immunoglobulin [for example, salt precipitation, alcohol precipitation, isoelectric precipitation, electrophoresis, adsorption and desorption with ion exchange materials (for example, DEAE), ultracentrifugation, gel filtration and specific purification in which only the antibodies are collected with active adsorbing agents such as antigen-binding solid phases, protein A and protein G]. Further, the hybridoma producing the anti-β-amyloid monoclonal antibody reactive to a partial region of the β-amyloid and the hybridoma producing the anti-β-amyloid monoclonal antibody reactive to the β-amyloid, but unreactive to a partial region thereof can be selected, for example, by assaying the binding property of a peptide corresponding to the partial region and an antibody produced by the hybridoma.

The antibody of the present invention thus obtained which is specifically reactive to the partial peptide on the C-terminal side of the β-amyloid or the derivative thereof; the monoclonal antibody indicated by BAN-052a; the monoclonal antibody indicated by BAN-50a; and the antibody specifically reactive to the partial peptide in the central portion of the β-amyloid or the derivative thereof can each specifically recognize the partial peptides on the N-terminal and C-terminal sides and in the central portion of the β-amyloid. They can be therefore used for determination of the β-amyloid or the derivative thereof in a test solution, particularly determination by the sandwich immunoassay.

Namely, the present invention provide:

(1) a method for determining a β-amyloid or a derivative thereof in a test solution which comprises competitively reacting an antibody of the present invention to the β-amyloid or the derivative thereof with the test solution and a labeled β-amyloid or a derivative thereof, and measuring the ratio of the labeled β-amyloid or the derivative thereof bound to said antibody;

(2) a method for determining a β-amyloid or a derivative thereof in a test solution which comprises reacting an antibody to a β-amyloid or a derivative thereof insolubilized on a carrier, a labeled antibody to a β-amyloid or a derivative thereof and the test solution with one another, and then, measuring the activity of a labeling agent on the carrier, in the method, one of the antibody to the β-amyloid or the derivative thereof insolubilized on the carrier and the labeled antibody to the β-amyloid or the derivative thereof being an antibody specifically reactive to a partial peptide on the C-terminal side of the β-amyloid or the derivative thereof, and the other being an antibody which recognizes a partial peptide having an amino acid sequence represented by SEQ ID NO:7 (namely, β-amyloid (1–28)) and/or a partial peptide having an amino acid sequence represented by SEQ ID NO:10 (namely, β-amyloid (1–16)); and (3) a method for determining a β-amyloid or a derivative thereof in a test solution which comprises reacting an antibody to a β-amyloid or a derivative thereof insolubilized on a carrier, a labeled antibody to a β-amyloid or a derivative thereof and the test solution with one another, and then, measuring the activity of a labeling agent on the carrier, in which one of the antibody to the β-amyloid or the derivative thereof insolubilized on the carrier and the labeled antibody to the β-amyloid or the derivative thereof being an antibody specifically reactive to a partial peptide in a central portion of the β-amyloid or the derivative thereof, and the other being an antibody which recognizes a partial peptide on the C-terminal side of the β-amyloid or the derivative thereof or an antibody which recognizes a partial peptide having an amino acid sequence represented by SEQ ID NO:7 or SEQ ID NO:10.

More specifically, the antibody specifically reactive to the partial peptide on the C-terminal side of the β-amyloid or the derivative thereof is the monoclonal antibody indicated by BA-27a, BS-85a or BC-05a, the antibody which recognizes the partial peptide having the amino acid sequence represented by SEQ ID NO:7 (namely, β-amyloid (1–28)) and/or the partial peptide having the amino acid sequence represented by SEQ ID NO:10 (namely, β-amyloid (1–16)) is the monoclonal antibody indicated by BAN-052a or BAN-50a, and the antibody specifically reactive to the partial peptide in the central portion of the β-amyloid or the derivative thereof is the antibody indicated by BP-90a.

Particularly preferred examples of the above-mentioned determining methods (2) include:

a determining method in which one of the antibodies to the β-amyloid or the derivative thereof insolubilized on the carrier and the labeled antibody to the β-amyloid or the derivative thereof is the monoclonal antibody indicated by BA-27a, the other is the monoclonal antibody indicated by BAN-052a or BAN-50a, and the β-amyloid is the peptide having the amino acid sequence represented by SEQ ID NO:1, SEQ ID NO:2, SEQ ID NO:3 or SEQ ID NO:4;

a determining method in which one of the antibodies to the β-amyloid or the derivative thereof insolubilized on the carrier and the labeled antibody to the β-amyloid or the derivative thereof is the monoclonal antibody indicated by BS-85a, the other is the monoclonal antibody indicated by BAN-052a or BAN-50a, and the β-amyloid is the peptide having the amino acid sequence represented by SEQ ID NO:1, SEQ ID NO:2, SEQ ID NO:3 or SEQ ID NO:5; and a determining method in which one of the antibodies to the β-amyloid or the derivative thereof insolubilized on the carrier and the labeled antibody to the β-amyloid or the derivative thereof is the monoclonal antibody indicated by BC-05a, the other is the monoclonal antibody indicated by BAN-052a or BAN-50a, and the β-amyloid is the peptide having the amino acid sequence represented by SEQ ID NO:5.

Particularly preferred examples of the above-mentioned determining methods (3) include:

a determining method in which one of the antibodies to the β-amyloid insolubilized on the carrier and the labeled antibody to the β-amyloid is the monoclonal antibody indicated by BP-90a, the other is the monoclonal antibody indicated by BAN-052a or BAN-50a, and the β-amyloid or the derivative thereof is the peptide having the amino acid sequence represented by SEQ ID NO:1, the peptide having the amino acid sequence represented by SEQ ID NO:2, the peptide having the amino acid sequence represented by SEQ ID NO:3, the peptide having the amino acid sequence represented by SEQ ID NO:4, the peptide having the amino acid sequence represented by SEQ ID NO:5 and/or the peptide having the amino acid sequence represented by SEQ ID NO:6; and a determining method in which one of the antibody to the β-amyloid insolubilized on the carrier and the labeled antibody to the β-amyloid is the monoclonal antibody indicated by BP-90a, the other is the monoclonal antibody indicated by BA-27a, BS-85a or BC-05a, and the β-amyloid or the derivative thereof is the peptide having the amino acid sequence lacking the 1st to the 16th amino acids or the 1st to the 17th amino acids from the amino acid sequence represented by any of SEQ ID NO:1 to SEQ ID NO:6.

The determining methods (immunoassays) of the β-amyloids or the derivatives thereof (hereinafter briefly referred to as the "β-amyloids") of the present invention are described in more detail below.

The antibodies of the present invention can recognize the β-amyloids, so that the assay or the detection by tissue staining of the β-amyloids can be conducted. For these purposes, either the antibodies themselves or F(ab')$_2$, Fab' or Fab fractions of antibody molecules may be used. The measuring methods using the antibodies of the present invention are not particularly limited. Any measuring method may be used, as long as the amount of the antibodies, the antigens or the antibody-antigen complexes corresponding to the amount of the antigens (for example, the amount of the β-amyloids) in solutions to be measured is detected by chemical or physical means, and calculated from standard curves prepared by the use of standard solutions containing the antigens in known amounts. For example, nephelometry, competitive methods, immunometric methods and sandwich methods are suitably used. With respect to sensitivity and specificity, it is particularly preferred to use the sandwich methods described below.

In measuring methods using labeling substances, radioisotopes, enzymes, fluorescent substances, luminous substances, etc. are used as labeling agents. Examples of the radioisotopes include $^{125}I$ $^{131}I$ $^3H$ and $^{14}C$. As the above-mentioned enzymes, it is preferred that they are stable and have a high specific activity. Examples thereof include β-galactosidase, β-glucosidase, alkaline phosphatase, peroxidase and malate dehydrogenase. Examples of the fluorescent substances include fluorescamine and fluorescein isothiocyanate. The luminous substances include, for example, luminol, luminol derivatives, luciferin and lucigenin. Further, biotin-avidin systems can also be used for binding of the antibodies or the β-amyloids with the labeling agents.

When the antigens or the antibodies are insolubilized, either physical adsorption-or chemical binding usually used for insolubilization or fixation of proteins or enzymes may be employed. Examples of the carriers include insoluble polysaccharides such as agarose, dextran and cellulose, synthetic resins such as polystyrene, polyacrylamide and silicone polymers, and glass.

In the sandwich methods, the test solutions are reacted with the insolubilized anti-β-amyloid antibodies (the first reaction), further, the labeled anti-β-amyloid antibodies are reacted (the second reaction), and then, the activity of the labeling agents on the insolubilized carriers is assayed, whereby the amount of the β-amyloids in the test solutions can be determined. The first reaction and the second reaction may be conducted simultaneously or sequentially. The labeling agents and the insolubilizing methods can be used in accordance with those described above. Further, in the immunoassays by the sandwich methods, the antibodies used as the antibodies for solid phases or the antibodies for labeling are not necessarily of one kind, but two or more kinds of antibodies may be used as mixtures for the purpose of enhancing the measuring sensitivity, etc.

In the methods of the present invention for measuring the β-amyloids by the sandwich methods, the anti-β-amyloid antibodies used in the first reaction are preferably different from those used in the second reaction in sites at which the antibodies bound to the β-amyloids. For example, when the antibody used in the first reaction recognizes the partial peptide on the N-terminal side of the β-amyloid, the antibody used in the second reaction is preferably an antibody which recognizes a partial peptide other than the partial peptide on the N-terminal side (namely, the partial peptide on the C-terminal side).

Specifically, of monoclonal antibodies prepared using β-amyloid (1–40) as the immunogen, an antibody which does not cross react with β-amyloid (1–28) is suitably used as the monoclonal antibody specifically reactive to the partial peptide on the C-terminal side of the β-amyloid. The present inventors established two kinds of hybridomas each of which produces such an antibody. The antibodies produced from these hybridomas did not cross react with β-amyloid (1–28) in competitive enzyme immunoassays using β-galactosidase-labeled β-amyloid (1–40) described below, but they reacted with β-amyloid (1–40) (antigen concentration giving $B/B_0=0.5$: 200 to 250 nM, 40 to 50 ng/well). Furthermore, when they were used in the sandwich methods, particularly in combination with BAN-50a or BAN-052a of monoclonal antibodies prepared using β-amyloid (1–16) described below as the immunogen which recognized the partial peptide on the N-terminal side of the β-amyloid, the result revealed that the β-amyloid could be measured unexpectedly with a higher sensitivity (detection sensitivity: 0.2 pg/well). Namely, as the monoclonal antibodies of one kind specifically reactive to the partial peptide on the C-terminal side of the β-amyloid suitable for the sandwich enzyme immunoassays of the present invention, monoclonal antibodies which react with β-amyloid (1–40), but do not cross react with β-amyloid (1–28) are suitably used. These antibodies do not necessarily require a high affinity for β-amyloid (1–40). For example, BA-27a is conveniently used as such an antibody.

Further, as the monoclonal antibodies specifically reactive to the partial peptide on the C-terminal side of the β-amyloid which are used in the sandwich immunoassays of the present invention, antibodies prepared using β-amyloid (25–35) as the immunogen are suitably used. The resent inventors established five kinds of hybridomas producing these antibodies. The antibodies reacted with β-amyloid (25–35) (antigen concentration giving $B/B_0=0.5$: 20 nM, 1 ng/well) in competitive enzyme immunoassays using β-galactosidase-labeled β-amyloid (1–40) described below, and also reacted with β-amyloid (1–40) (antigen concentration giving $B/B_0=0.5$: 800 nM, 160 ng/well). Further, the combination of the antibodies with BAN-50a or BAN-052a unexpectedly gives a higher sensitivity (detection sensitivity: 3 pg/well). Namely, in the sandwich enzyme immunoassays of the present invention, monoclonal antibodies to β-amyloid (25–35) are suitably used as the monoclonal antibodies specifically reactive to the partial peptide on the C-terminal side of the β-amyloid. These antibodies do not necessarily require a high affinity for β-amyloid (1–40). For example, BS-85a is conveniently used as such an antibody.

In the sandwich methods in which BS-85a was combined with BAN-50a or BAN-052a, or BA-27a was combined with BAN-50a or BAN-052a, no cross reactivity with β-amyloid (1–28) was observed.

Furthermore, as the monoclonal antibodies specifically reactive to the partial peptide on the C-terminal side of the β-amyloid which are used in the sandwich immunoassays of the present invention, antibodies prepared using β-amyloid (35–43) as the immunogen are suitably used. The present inventors prepared eighteen kinds of hybridomas producing these antibodies. Of these, four kinds of antibodies exhibited a high reactivity to β-amyloid fractions (formic acid extracts) extracted from the brains of the patients with Alzheimer's disease by the method of Mori et al. [*J. Biol. Chem.*, 267, 17082–17086 (1988)] in competitive enzyme immunoassays using peroxidase-labeled β-amyloid (35–43) described below, whereas they exhibited no reactivity with a synthesized β-amyloid (1–40). The use of these antibodies in the sandwich methods in a combination with BAN-50a showed that the β-amyloids contained in the above-mentioned formic acid extracts from the brains of the patients with Alzheimer's disease were detected with high sensitivity, and that β-amyloid (1–40) was not detected at all. Mass spectrometry indicated that the β-amyloids contained in the formic acid extracts from the brains of the patients with Alzheimer's disease were mainly composed of β-amyloid (1–42), and that they further contained molecular species successively lacking N-terminal portions, including β-amyloid (3–42) having pyroglutamic acid at the N-terminal portion, β-amyloid (2–42) and β-amyloid (4–42).

On the other hand, as the monoclonal antibodies recognizing the partial peptide on the N-terminal side of the β-amyloid which are used in the sandwich immunoassays of the present invention, antibodies prepared using β-amyloid (1–16) as the immunogen are suitably used. The present inventors prepared eight kinds of hybridomas producing these antibodies. The reactivity of these antibodies to β-amyloid (1–40) was examined by competitive methods using peroxidase-labeled β-amyloid (1–16) described below. As a result, four kinds of antibodies showed a good reactivity to β-amyloid (1–40) (antigen concentration giving B/B₀=0.5: 25 to 70 nM, 5 to 15 ng/well). Further, when these antibodies were applied to the sandwich methods, a large difference in sensitivity among these antibodies was unexpectedly observed. Namely, monoclonal antibody BAN-052a gave outstanding high sensitive sandwich determining methods, compared with other three kinds of antibodies (BAN-11a, BAN-20a and BAN-30a). Then, sixteen kinds of antibodies were newly prepared in order to select anti-β-amyloid (1–16) monoclonal antibodies more suitable for the sandwich methods, and examined by the competitive methods using peroxidase-labeled β-amyloid (1–16). As a result, of these antibodies, ten kinds of antibodies showed a good reactivity to β-amyloid (1–40). In particular, BAN-50a gave extremely high sensitive sandwich determining methods among others. Namely, in the present invention, several kinds of antibodies to β-amyloid (1–16) are provided as the antibodies suitable for the sandwich methods, which recognize the partial peptide on the N-terminal side of the β-amyloid, and particularly, BAN-50a and BAN-052a are suitably used.

Further, as the monoclonal antibodies recognizing the partial peptide in the central portion of the β-amyloid which are used in the sandwich immunoassays of the present invention, antibodies prepared using β-amyloid (18–28) represented by SEQ ID NO:12 as the immunogen are suitably used. The present inventors prepared nine kinds of hybridomas producing these antibodies. In particular, monoclonal antibodies BP-01a, BP-02a, BP-03a and BP-90a produced from four hybridomas BP-01, BP-02, BP-03 and BP-90 are suitable, and BP-03a and BP-90a can also recognize β-amyloid (17–28) represented by SEQ ID NO:11. Of these monoclonal antibodies, BP-90a is particularly suitable.

The monoclonal antibodies of the present invention can also be used in assay systems other than the sandwich methods, for example, competitive methods, immunometric methods and nephelometry. In the competitive methods, antigens in test solutions and labeled antigens are competitively reacted with the antibodies, followed by separation of the unreacted labeled antigens (F) from the labeled antigens (B) bound to the antibodies (B/F separation). Then, the labeled amount of either B or F is measured to determine the amount of the antigens in the test solutions. These reaction methods include liquid phase methods in which soluble antibodies are used as the antibodies, and polyethylene glycol and the second antibodies to the above-mentioned antibodies are used for B/F separation, and solidifying methods in which solidified antibodies are used as the first antibodies, or soluble antibodies are used as the first antibodies and solidified antibodies are used as the second antibodies.

In the immunometric methods, antigens in test solutions and solidified antigens are competitively reacted with fixed amounts of labeled antibodies, followed by separation of solid phases from liquid phases, or antigens in test solutions are reacted with excess labeled antibodies, and then, solidified antigens are added to allow the unreacted labeled antibodies to bind to solid phases, followed by separation of the solid phases from liquid phases. Then, the labeled amount of either phases is measured to determine the amount of the antigens in the test solutions.

In the nephelometry, the amount of insoluble precipitates produced as a result of antigen-antibody reaction in gels or solutions is measured. Even when the amount of antigens in test solutions is slight, and the precipitates are obtained only in small amounts, laser nephelometry utilizing laser scattering is suitably used.

When these immunological assays are applied to the present invention, particular conditions and operations are not required to be established. Usual technical consideration of those skilled in the art may be added to ordinary conditions and operations in the respective assays to construct assay systems of the β-amyloids. Details of these general technical means can be referred to reviews and books [for example, *Radioimmunoassays* edited by H. Irie (published by Kodansha in 1974), *Radioimmunoassays, second series*, edited by H. Irie (published by Kodansha in 1979), *KOSO MENEKI SOKUTEIHO (Enzyme Immunoassays)*, edited by E. Ishikawa et al. (published by Igaku Shoin in 1978), *KOSO MENEKI SOKUTEIHO (Enzyme Immunoassays) (second edition)*, edited by E. Ishikawa et al. (published by Igaku Shoin in 1982), *KOSO MENEKI SOKUTEIHO (Enzyme Immunoassays) (third edition)*, edited by E. Ishikawa et al. (published by Igaku Shoin in 1987), *Methods in ENZYMOLOGY*, Vol. 70 (Immunochemical Techniques (Part A) published by Academic Press, ibid., Vol. 73 (Immunochemical Techniques (Part B), ibid., Vol. 74 (Immunochemical Techniques (Part C), ibid., Vol. 84 (Immunochemical Techniques (Part D: Selected Immunoassays), ibid., Vol. 92 (Immunochemical Techniques (Part E: Monoclonal Antibodies and General Immunoassay Methods), and ibid., Vol. 121 (Immunochemical Techniques (Part I: Hybridoma Technology and Monoclonal Antibodies)]. Accordingly, when the assay systems of the β-amyloids are constructed by the sandwich immunoassays of the present invention, they are not limited to examples described below.

As described above, the antibodies of the present invention can determine the β-amyloids or the derivatives thereof with a high sensitivity, so that they are useful as diagnosing agents for Alzheimer's disease.

BEST MODE FOR CARRYING OUT THE INVENTION

Examples

Figure 1:
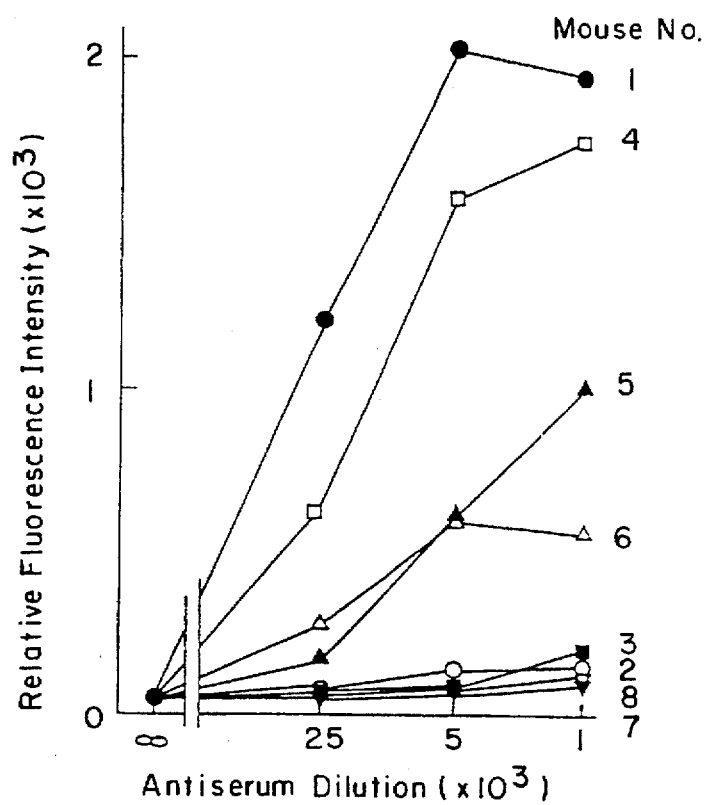
FIG. 1 is a graph showing the results of assay of the antibody titer of mice immunized with β-amyloid (1–40), said antibody titer being assayed by β-Gal-labeled β-amyloid (1–40)

[Example 1] Preparation of Antigens (1) Production of β-Amyloid (1–40)

β-Amyloid (1–40) was synthesized by using 0.71 g (0.5 mmol) of a commercially available Boc-Val-OCH$_2$-PAM resin (Applied Biosystems) with a peptide synthesizer (Model 430A, Applied Biosystems). The Boc group on the resin was treated with 50% trifluoroacetic acid/methylene chloride to deprotect the amino group. Then, 2 mmol portions of Boc-Gly, Boc-Val, Boc-Met, Boc-Leu, Boc-Ile, Boc-Ala, Boc-Lys(Cl-Z), Boc-Asn, Boc-Asp(OcHex), Boc-Glu(OcHex), Boc-Phe, Boc-Gln, Boc-His(Bom), Boc-Tyr (Br-Z), Boc-Ser(Bzl) and Boc-Arg(Tos) were activated with HOBt/DCC and condensed according to the amino acid sequence of β-amyloid (1–40) to obtain 2.70 g of a protected β-amyloid (1–40)-OCH$_2$-PAM resin. The resulting protected β-amyloid (1–40)-OCH$_2$-PAM resin (0.56 g) was treated with 10 ml of anhydrous hydrogen fluoride in the presence of p-cresol at 0C for 60 minutes, followed by removal of excess hydrogen fluoride by distillation under reduced pressure. The residue was washed twice with 10 ml of ether, and then extracted with 50% aqueous acetic acid. The insoluble material was removed by filtration, followed by washing with 50% aqueous acetic acid. The filtrate and the washings were combined, and the combined solution was concentrated to 2 to 3 ml under reduced pressure. The concentrated solution was subjected to a Sephadex G-25 column (2.0×85 cm) charged with 50% aqueous acetic acid, and developed with the same solvent. The main fractions were collected and lyophilized to obtain about 150 mg of a yellowish white powder. This was dissolved in 50 ml of 20% aqueous acetonitrile (containing 0.1% trifluoroacetic acid), and the resulting solution was subjected to a LiChroprep RP-18 column (4.1×10 cm) filled with the same solvent to elute the column with a linear gradient of from 20% to 70% aqueous acetonitrile (containing 0.1% trifluoroacetic acid). The main fractions were collected and subjected to a LiChroprep RP-18 column (2.6×6 cm) again to elute the column with a linear gradient of from 0% to 50% aqueous acetonitrile (containing 0.1% trifluoroacetic acid). The main fractions were collected and lyophilized to obtain 10 mg of a white powder.

Anal. for amino acids: Gly 6.85(6), Ala 3.44(3), Val 5.68(6), Leu 2.00(2), Ile 1.39(2), Met 0.89(1), Phe 3.21(3), Ser 1.89(2), Asp 4.35(4), Glu 4.52(4), Lys 2.05(2), His 2.86(3), Arg 1.10(1), Tyr 0.97(1)

(M+H)$^+$ by mass spectrometry: 4328.05

HPLC elution time: 22.8 minutes

Column conditions

Column: Wakosil-5C18 HG (4.6×100 mm)

Eluents: A (0.1% aqueous trifluoroacetic acid) B (acetonitrile containing 0.1% trifluoroacetic acid)

(2) Production of [Cys$^{17}$] β-Amyloid (1–16)

[Cys$^{17}$] β-Amyloid (1–16) was synthesized by using 0.75 g (0.5 mmol) of a commercially available Boc-Cys(MeBzl)-OCH$_2$-PAM resin (Applied Biosystems) with a peptide synthesizer (Model 430A, Applied Biosystems). The Boc group on the resin was treated with 50% trifluoroacetic acid/methylene chloride to deprotect the amino group. Then, 2 mmol portions of Boc-Lys(Cl-Z), Boc-Gln, Boc-His (Bom), Boc-Val, Boc-Glu(OcHex), Boc-Tyr(Br-Z), Boc-Gly, Boc-Ser(Bzl), Boc-Asp(OcHex), Boc-Arg(Tos) and Boc-Phe were activated with HOBt/DCC and condensed according to the amino acid sequence of [Cys$^{17}$] β-Amyloid (1–16) to obtain 1.90 g of a protected [Cys$^{17}$] β-Amyloid (1–16) (MeBzl)-OCH$_2$-PAM resin. The resulting protected [Cys$^{17}$] β-Amyloid (1–16) (MeBzl)-OCH$_2$-PAM resin (0.68 g) was treated with 10 ml of anhydrous hydrogen fluoride in the presence of p-cresol at 0C for 60 minutes, followed by removal of excess hydrogen fluoride by distillation under reduced pressure. The residue was washed twice with 10 ml of ether, and then extracted with 50% aqueous acetic acid. The insoluble material was removed by filtration, followed by washing with 50% aqueous acetic acid. The filtrate and the washings were combined, and the combined solution was concentrated to 1 to 2 ml under reduced pressure. The concentrated solution was subjected to a Sephadex G-25 column (2.0×85 cm) filled with 50% aqueous acetic acid, and developed with the same solvent. The main fractions were collected and lyophilized to obtain 136.7 mg of a white powder.

Anal. for amino acids: Asp 2.17(2), Ser 0.96(1), Glu 3.04(3), Gly 1.00(1), Ala 1.00(1), Cys 0.82(1), Val 0.99(1), Tyr 0.94(1), Phe 1.09(1), Lys 1.05(1), His 2.89(3), Arg 0.97(1), (M+H)$^+$ by mass spectrometry: 2056.83
HPLC elution time: 14.8 minutes
Column conditions
Column: Wakosil-5C18 HG (4.6×100 mm)
Eluents: A (0.1% aqueous trifluoroacetic acid) B (acetonitrile containing 0.1% trifluoroacetic acid)
A linear gradient elution from eluent A to eluent B (for 50 minutes)
Flow rate: 1.0 ml/minute (3) Production of β-Amyloid (25–35)

β-Amyloid (25–35) was synthesized by using 0.66 g (0.5 mmol) of a commercially available Boc-Met-OCH$_2$-PAM resin (Applied Biosystems) with a peptide synthesizer (Model 430A, Applied Biosystems). The Boc group on the resin was treated with 50% trifluoroacetic acid/methylene chloride to deprotect the amino group. Then, 2 mmol portions of Boc-Leu, Boc-Gly, Boc-Ile, Boc-Ala, Boc-Lys(Cl-Z), Boc-Asn and Boc-Ser(Bzl) were activated with HOBt/DCC and condensed according to the amino acid sequence of β-amyloid (25–35) to obtain 1.14 g of a protected β-amyloid (25–35)-OCH$_2$-PAM resin. The resulting protected β-amyloid (25–35)-OCH$_2$-PAM resin (0.61 g) was treated with 10 ml of anhydrous hydrogen fluoride in the presence of p-cresol at 0C for 60 minutes, followed by removal of excess hydrogen fluoride by distillation under reduced pressure. The residue was washed twice with 10 ml of ether, and then extracted with 50% aqueous acetic acid. The insoluble material was removed by filtration, followed by washing with 50% aqueous acetic acid. The filtrate and the washings were combined, and the combined solution was concentrated to 2 to 3 ml under reduced pressure. The concentrated solution was diluted with 50 ml of 0.1% aqueous trifluoroacetic acid, and then subjected to a LiChroprep RP-18 column (2.6×10 cm) filled with 0.1% aqueous trifluoroacetic acid to elute the column with a linear gradient of from 0% to 50% aqueous acetonitrile (containing 0.1% trifluoroacetic acid). The main fractions were collected and lyophilized to obtain 100 mg of a white powder. This powder was dissolved in 0.5 ml of N-acetic acid, and subjected to a Sephadex LH-20 column (1.0×96 cm) filled with the same solvent. The main fractions were collected and lyophilized to obtain 91 mg of a white powder.

Anal. for amino acids: Asp 0.97(1), Ser 0.95(1), Gly 2.94(3), Ala 1.00(1), Met 0.89(1), Ile 1.59(2), Leu 1.00(1), Lys 0.97(1), (M+H)$^+$ by mass spectrometry: 2056.83
HPLC elution time: 18.9 minutes
Column conditions
Column: Wakosil-5C18 HG (4.6×100 mm)
Eluents: A (0.1% aqueous trifluoroacetic acid) B (acetonitrile containing 0.1% trifluoroacetic acid)
A linear gradient elution from eluent A to eluent B (for 50 minutes)
Flow rate: 1.0 ml/minute (4) Production of [Cys$^{34}$] β-Amyloid (35–43)

A Fmoc-Thr(tBu)-Wang resin (0.46 g: 0.25 mmol, Watanabe Kagaku) was used as a starting material. After deprotection of the Fmoc group with a 20% piperidine-DMF solution, the peptide chain was sequentially extended from the C-terminal side by the DCC-HOBt method, using a Fmoc-amino acid derivative cartridge (1.0 mmol, Applied Biosystems). Thus, 0.73 g of a protected peptide resin represented by the following formula was obtained:

Fmoc-Cys(Trt)-Met-Val-Gly-Gly-Val-Val-Ile-Ala-Thr(tBu)-Wang resin

Then, 0.75 g of phenol, 0.25 ml of butanedithiol, 0.5 ml of thioanisole, 0.5 ml of deionized water and 10 ml of trifluoroacetic acid were added to 0.58 g (0.20 mmol) of this peptide resin under ice cooling, and the mixture was stirred at room temperature for 1.5 hours. The resin was removed by filtration, and the filtrate was concentrated. Ether was added to the residue under ice cooling, and a precipitate was collected by filtration. After thorough washing with ether, the precipitate was dried to obtain a white powder.

Yield: 168 mg (89%) (M+H)$^+$ by mass spectrometry: 949.5 (theoretical value=949.5)

(5) Preparation of β-Amyloid (1–38) and β-Amyloid (1–39)

β-Amyloid (1–40) was restrictedly hydrolyzed with carboxypeptidase Y, thereby preparing β-amyloid (1–38) and β-amyloid (1–39). Namely, 50 μg of β-amyloid (1–40) (Bachem) and 0.5 μg of carboxypeptidase Y (Oriental Yeast Co., Ltd.) were dissolved in 0.5% aqueous ammonium acetate to bring it up to 60 μl, followed by reaction at 10° C. for 2 hours. After reaction, the product was fractionated by reverse-phase HPLC using a Vydac C4 column (The Sep/a/ra/tions Group), and three main peaks detected by UV (210 nm) were identified by mass spectrometry.

Column conditions
Column: Vydac C4 (The Sep/a/ra/tions Group, 4.6×250 mm)
Eluents: A (5% acetonitrile containing 0.1% trifluoroacetic acid) B (80% acetonitrile containing 0.1% trifluoroacetic acid)
Elution Method: The concentration of eluent B was first maintained to 30% for 5 minutes, and then linearly increased to 30–50% for 60 minutes.

Flow rate: 0.5 ml/minute
(M+H)⁺ by mass spectrometry: 4132.9: β-amyloid (1–38) (theoretical value=4132.6) 4231.6: β-amyloid (1–39) (theoretical value=4231.8) 4330.9: β-amyloid (1–40) (theoretical value=4330.9)

[Example 2] Preparation of Immunogens
(1) Preparation of Immunogen Comprising β-Amyloid (1–40)

A complex of β-amyloid (1–40) obtained in Example 1 (1) described above and bovine thyroglobulin (BTG) was prepared, and used as an immunogen. Namely, 0.6 mg of β-amyloid (1–40) was dissolved in 1.1 ml of 3 mM phosphate buffer (pH 6.5) containing 15% DMF, and then 2.5 mg of BTG dissolved in 0.5 ml of water was added thereto. Further, glutaraldehyde was added to give a final concentration of 0.3%, followed by reaction at room temperature for 3 hours. After reaction, the product was dialyzed against physiological saline at 4° C. for 2 days.

(2) Preparation of Immunogen Containing β-Amyloid (25–35)

A complex of β-amyloid (25–35) obtained in Example 1 (3) described above and BTG was prepared, and used as an immunogen. Namely, 0.5 mg of β-amyloid (25–35) and 2.5 mg of BTG were dissolved in 1 ml of water adjusted to pH 4.5, and glutaraldehyde was further added to give a final concentration of 0.4%, followed by reaction at room temperature for 3 hours. After reaction, the product was dialyzed against physiological saline at 4° C. for 2 days.

(3) Preparation of Immunogen Containing β-Amyloid (1–16)

A complex of [Cys$^{17}$] β-amyloid (1–16) obtained in Example 1 (2) and BTG was prepared, and used as an immunogen. Namely, 20 mg of BTG was dissolved in 1.4 ml of 0.1M phosphate buffer (pH 6.9), and the resulting solution was mixed with 100 μl of a DMF solution containing 2.2 mg (8 μmols) of N-(γ-maleimidobutyryloxy)succinimide (GMBS), followed by reaction at room temperature for 40 minutes. After reaction, the product was fractionated on a Sephadex G-25 column. Then, 15 mg of maleimide group-introduced BTG was mixed with 3.6 mg of [Cys$^{17}$] β-amyloid (1–16), followed by reaction at 4° C. for 2 days. After reaction, the product was dialyzed against physiological saline at 4° C. for 2 days.

(4) Preparation of Immunogen Containing β-Amyloid (35–43)

A complex of [Cys$^{34}$] β-amyloid (35–43) obtained in Example 1 (4) and bovine serum albumin (BSA) was prepared, and used as an immunogen. Namely, 21 mg (0.31 μmol) of BSA was dissolved in 1.4 ml of 0.1M phosphate buffer (pH 6.8), and the resulting solution was mixed with 100 μl of a DMF solution containing 3.5 mg (12.5 μmols) of GMBS, followed by reaction at room temperature for 35 minutes. After reaction, the product was fractionated on a Sephadex G-25 column. Then, 4.5 mg of maleimide group-introduced BSA was mixed with 2.1 mg of [Cys$^{34}$] β-amyloid (35–43), followed by reaction overnight at 4° C. After reaction, the product was dialyzed against physiological saline at 4° C. for 2 days.

(5) Preparation of Immunogen Containing β-Amyloid (18–28)

A complex of [Cys$^{29}$] β-amyloid (18–28) and BTG was prepared, and used as an immunogen. Namely, 21 mg of BTG was dissolved in 1.5 ml of 0.1M phosphate buffer (pH 6.9), and the resulting solution was mixed with 100 μl of a DMF solution containing 2.4 mg (8.4 μmols) of GMBS, followed by reaction at room temperature for 40 minutes. After reaction, the product was fractionated on a Sephadex G-25 column. Then, about 7 mg of maleimide group-introduced BTG was mixed with 2.0 mg of [Cys$^{29}$] β-amyloid (18–28) (Accord), followed by reaction overnight at 4° C. After reaction, the product was dialyzed against physiological saline at 4° C. for 3 days.

[Example 3] Immunization

Six to eight-week-old BALB/C female mice were subcutaneously immunized with about 80 μg/mouse of each of the immunogens obtained in Example 2 described above, the β-amyloid (1–40)-BTG complex, the β-amyloid (25–35)-BTG complex, the β-amyloid (1–16)-BTG complex, the β-amyloid (35–43)-BSA complex and the β-amyloid (18–28)-BTG complex, together with Freund's complete adjuvant. Thereafter, the mice were supplementally immunized with the same dose of each of the immunogens, together with Freund's incomplete adjuvant, 2 to 3 times at 3 week intervals.

[Example 4] Preparation of Enzyme-Labeled Antigens
(1) Preparation of β-D-Galactosidase (β-Gal)-Labeled β-Amyloid (1–40)

In 40 μl of DMSO was dissolved 70 μg (16 nmols) of β-amyloid (1–40), and 160 nmols (10 μl DMSO solution) of triethylamine and 23 nmols (7 μl DMSO solution) of N-succinimidyl-3-(2-pyrimidyldithio)propionate (SPDP) were added thereto, followed by reaction at room temperature for 90 minutes. The total amount of the reaction solution was added to 1.7 mg (3.3 nmols) of β-Gal (for enzyme immunoassay, Boehringer Mannheim) dissolved in 0.45 ml of 0.1M phosphate buffer (pH 7.5), followed by reaction at 4° C. for a day. After reaction, the product was fractionated on an Ultrogel AcA34 column (LKB-Pharmacia) to obtain β-Gal-labeled β-amyloid (1–40).

(2) Preparation of Horseradish Peroxidase (HRP)-Labeled β-Amyloid (1–16)

[Cys$^{17}$] β-amyloid (1–16) obtained in Example 1 (2) described above was crosslinked with HRP (for enzyme immunoassay, Boehringer Mannheim) to prepare a labeled material for enzyme immunoassay (EIA). Namely, 5 mg (125 nmols) of HRP was dissolved in 0.95 ml of 0.1M phosphate buffer (pH 6.8), and the resulting solution was mixed with 50 μl of a DMF solution containing 3.6 mg (1.3 μmols) of GMBS, followed by reaction at room temperature for 30 minutes. Thereafter, the reaction product was fractionated on a Sephadex G-25 column. Then, 3.3 mg (78 nmols) of maleimide group-introduced HRP was mixed with 0.56 mg (270 nmols) of [Cys$^{17}$] β-amyloid (1–16), followed by reaction at 4° C. for a day. After reaction, the product was fractionated on an Ultrogel AcA34 column (LKB-Pharmacia) to obtain HRP-labeled β-amyloid (1–16).

(3) Preparation of HRP-Labeled β-Amyloid (35–43)

[Cys$^{34}$] β-amyloid (35–43) obtained in Example 1 (4) described above was crosslinked with HRP to prepare a labeled material for EIA. Namely, 12 mg (310 nmols) of HRP was dissolved in 1.4 ml of 0.1M phosphate buffer (pH 6.8), and the resulting solution was mixed with 100 μl of a DMF solution containing 1.3 mg (4.5 μmols) of GMBS, followed by reaction at room temperature for 30 minutes. Thereafter, the reaction product was fractionated on a Sephadex G-25 column. Then, 3.2 mg (76 nmols) of maleimide group-introduced HRP thus prepared was mixed with 2.1 mg (7.2 μmols) of [Cys$^{34}$] β-amyloid (35–43) obtained in Example 1(4), followed by reaction at 4° C. for a day. After reaction, the product was fractionated on an Ultrogel AcA34 column to obtain HRP-labeled β-amyloid (35–43).

(4) Preparation of HRP-Labeled β-Amyloid (18–28)

[Cys29] β-amyloid (18–28) was crosslinked with HRP to prepare a labeled material for EIA. Namely, 16 mg (390 nmols) of HRP was dissolved in 1.4 ml of 0.1M phosphate buffer (pH 6.8), and the resulting solution was mixed with 100 μl of a DMF solution containing 1.1 mg (3.9 μmols) of GMBS, followed by reaction at room temperature for 40 minutes. Thereafter, the reaction product was fractionated on a Sephadex G-25 column. Then, 6.0 mg (150 nmols) of maleimide group-introduced HRP thus prepared was mixed with 2.5 mg (1.9 μmols) of [$Cys^{29}$] β-amyloid (18–28), followed by reaction at 4° C. for 2 days. After reaction, the product was fractionated on an Ultrogel AcA34 column to obtain HRP-labeled β-amyloid (18–28).

[Example 5] Determination of Antibody Titer (1) Determination of Antibody Titer in Antisera of Mice Immunized with β-Amyloid (1–40)

The antibody titer in the antisera of mice immunized with β-amyloid (1–40) was determined by the following method. In order to prepare an anti-mouse immunoglobulin antibody-binding microplate, 100 μl of 0.1M carbonate buffer (pH 9.6) containing 100 μg/ml of an anti-mouse immunoglobulin antibody (IgG fraction, Kappel) was poured into each well of a 96-well microplate, and allowed to stand at 4° C. for 24 hours. Then, the plate was washed with phosphate buffered saline (PBS, pH 7.4), and thereafter 300 μl of PBS containing 25% Block Ace (Snow Brand Milk Products) was poured into each well to block excess binding sites of the wells, followed by treatment at 4° C. for at least 24 hours. To each well of the above-mentioned anti-mouse immunoglobulin antibody-binding microplate were added 50 μl of buffer A [0.02M phosphate buffer (pH 7.0) containing 0.1% BSA, 0.1M NaCl, 1 mM $MgCl_2$, 0.05% CHAPS [3-[(cholamidopropyl)dimethylammonio]propanesulfonic acid and 0.1% $NaN_3$] and 100 μl of the mouse anti-β-amyloid (25–35) antiserum diluted with buffer A, followed by reaction at 40C for 16 hours. Then, after the plate was washed with PBS, 100 μl of β-Gal-labeled β-amyloid (1–40) prepared in Example 4 (1) described above (200-fold dilution with buffer A) was added, followed by reaction at room temperature for a day. Then, after the plate was washed with PBS, 100 μl of a solution of 20 μg/ml 4-methyl-umbelliferyl-β-D-galactoside (4-MUG) in buffer A (with the proviso that CHAPS was not contained) was added, followed by reaction at 37° C. for 3 hours, in order to assay the enzyme activity on the solid phase by 4-MUG. After 100 μl of 0.2M $Na_2CO_3$ was added to terminate the reaction, released 4-methylumbelliferone was determined at an excitation wavelength of 355 nm at a determination wavelength of 460 nm by the use of a fluorescence plate reader (Fluoroscan II, Labosystem). Results are shown in FIG. 1. Of the 8 immunized mice, 4 mice exhibited a relatively high antibody titer.

Figure 2:
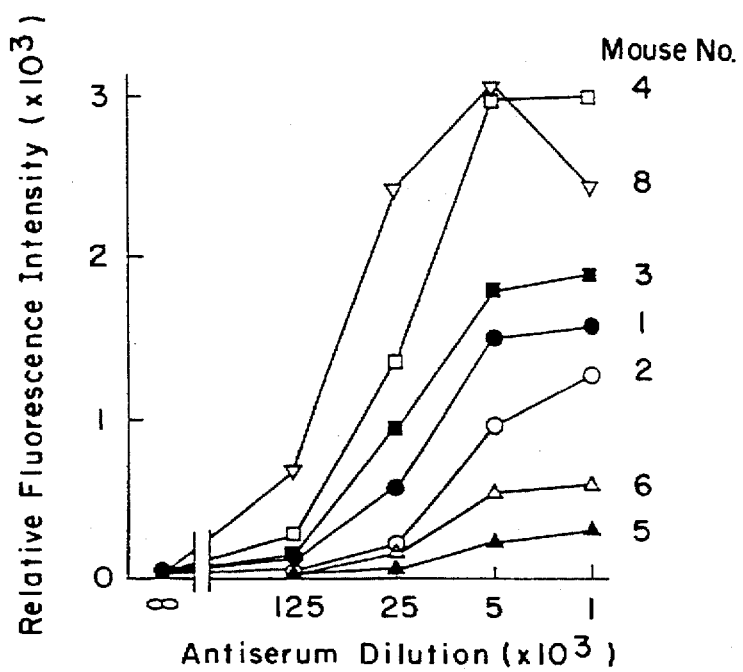
FIG. 2 is a graph showing the results of assay of the antibody titer of mice immunized with β-amyloid (25–35), said antibody titer being assayed by β-Gal-labeled β-amyloid (1–40)

(2) Determination of Antibody Titer in Antisera of Mice Immunized with β-Amyloid (25–35) The antibody titer in the antisera of mice immunized with β-amyloid (25–35) was determined in a manner similar to that described above. To each well of the anti-mouse immunoglobulin antibody-binding microplate were added 50 μl of buffer A, 50 μl of the mouse anti-β-amyloid (25–35) antiserum diluted with buffer A and 50 μl of β-Gal-labeled β-amyloid (1–40) prepared in Example 4 (1) described above (100-fold dilution with buffer A), followed by reaction at 4° C. for 16 hours. Then, after the plate was washed with PBS, the enzyme activity on the solid phase was similarly determined by the use of 4-MUG. Results are shown in FIG. 2. Of the 8 immunized mice, the 5 mice exhibited a relatively high antibody titer.

(3) Determination of Antibody Titer in Antisera of Mice Immunized with β-Amyloid (1–16)

Figure 3:
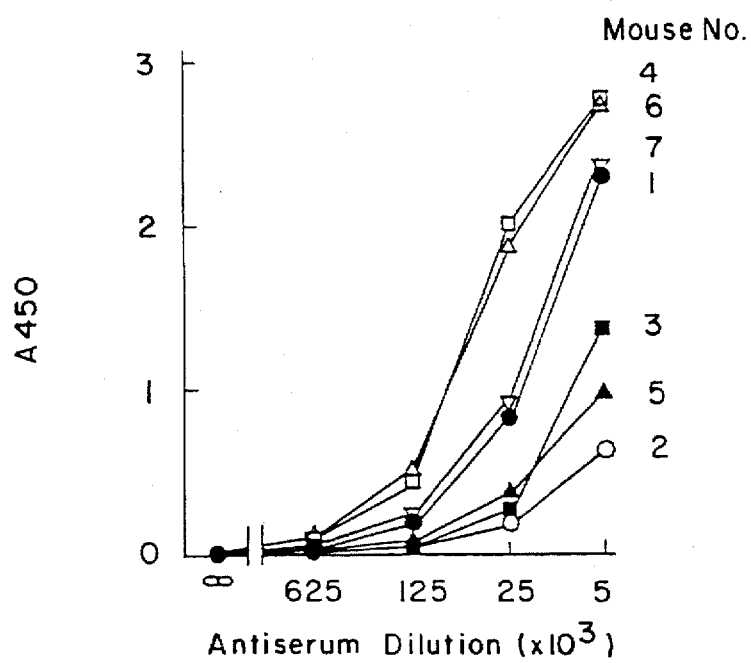
FIG. 3 is a graph showing the results of assay of the antibody titer of mice immunized with β-amyloid (1–16), said antibody titer being assayed by HRP-labeled β-amyloid (1–16)

The antibody titer in the antisera of mice immunized with β-amyloid (1–16) was determined by the following method. To each well of the anti-mouse immunoglobulin antibody-binding microplate were added 50 μl of buffer C [0.02M phosphate buffer (pH 7.0) containing 1% BSA, 0.4M NaCl and 2 mM EDTA], 50 μl of the mouse anti-β-amyloid (1–16) antiserum diluted with buffer C and 50 μl of HRP-labeled β-amyloid (1–16) prepared in Example 4 (2) described above (200-fold dilution with buffer C), followed by reaction at 4° C. for 16 hours. Then, after the plate was washed with PBS, the enzyme activity on the solid phase was determined by adding 100 μl of a TMB microwell peroxidase substrate system (KIRKEGAARD & PERRY LAB, INC., supplied by Funakosi Yakuhin), and reacting it at room temperature for 10 minutes. After 100μl of 1M phosphoric acid was added to terminate the reaction, the absorption at 450 nm was measured with a plate reader (MTP-32, Corona). Results are shown in FIG. 3. An increase in antibody titer to β-amyloid (1–16) was observed in all of the 7 immunized mice. (4) Determination of Antibody Titer in Antisera of Mice Immunized with β-Amyloid (35–43)

Figure 4:
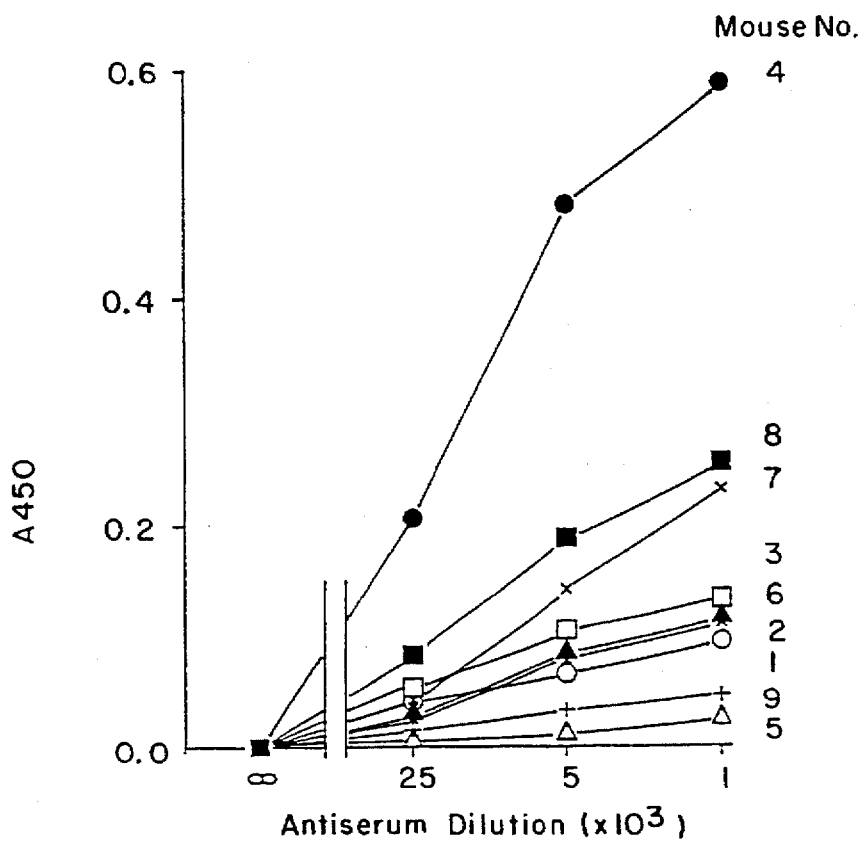
FIG. 4 is a graph showing the results of assay of the antibody titer of mice immunized with β-amyloid (35–43), said antibody titer being assayed by HRP-labeled β-amyloid (35–43)

According to the method described in Example 5 (3) described above, the anti-mouse immunoglobulin antibody-binding microplate, the mouse anti-β-amyloid (35–43) antiserum and the HRP-labeled β-amyloid (35–43) prepared in Example 4 (3) described above were reacted with one another to determine the antibody titer in the sera of mice. Results are shown in FIG. 4. Of the 9 immunized mice, 3 mice exhibited a relatively high antibody titer.

(5) Determination of Antibody Titer in Antisera of Mice Immunized with β-Amyloid (18–28)

According to the method described in Example 5 (3) described above, the anti-mouse immunoglobulin antibody-binding microplate, the mouse anti-β-amyloid (18–28) antiserum and the HRP-labeled β-amyloid (18–28) prepared in Example 4 (4) described above were reacted with one another to determine the antibody titer in the sera of mice. Of the 7 immunized mice, the 4 mice exhibited a relatively high antibody titer.

[Example 6] Preparation of Monoclonal Anti-β-Amyloid Antibody

Each of the mice which showed a relatively high antibody titer was intravenously inoculated with 0.25 to 0.3 ml of physiological saline in which 200 to 300 μg of the immunogen was contained to perform the final immunization. The spleens were taken out of the mice 3 to 4 days after the final immunization, pressed by a stainless mesh, filtered and floated in Eagle's minimum essential medium (MEM) to obtain a spleen cell floating solution. As cells used for cell fusion, BALB/C mouse-derived myeloma cells P3-X63.Ag8.U1 (P3U1) were used [Current Topics in Microbiology and Immunology, 81, 1 (1978)]. The cell fusion was conducted according to the original method [Nature, 256, 495 (1975)]. Namely, the spleen cells and P3U1 were each washed 3 times with serum-free MEM, and mixed so as to give a spleen cell number to P3U1 number ratio of 5:1. The mixture was centrifuged at 800 rpm for 15 minutes to precipitate the cells. After the supernatant was removed, the precipitate was lightly loosened, and 0.3 ml of 45% polyethylene glycol (PEG) 6000 (Kochlight) was added thereto. Then, the mixture was allowed to stand in a water bath at 37° C. for 7 minutes to perform fusion. After fusion, MEM was added to the cells at a rate of 2 ml per minute. After the total amount of MEM added reached 15 ml, the supernatant was removed by centrifugation at 600 rpm for 15 minutes. The resulting cell precipitate was floated in GIT medium (Wako Pure Chemical Industries) containing 10% fetal calf serum (GIT-10% FCS) so as to give $2 \times 10^5$ P3U1 cells per ml. The cell suspension was plated in 120 wells of 24-well multi-dishes (Linbro) in an amount of 1 ml per well. After plating, the cells were incubated in a 5% carbon dioxide incubator at 37° C. After 24 hours, GIT-10% FCS medium containing HAT ($1 \times 10^{-4}$M hypoxanthine, $4 \times 10^{-7}$M aminopterin and $1.6 \times 10^{-3}$M thymidine) (HAT medium) was added in an amount of 1 ml per well to initiate HAT selective culture. The HAT selective culture was continued by discarding 1 ml of old liquor and then adding 1 ml of HAT medium, 3, 6 and 9 days after initiation of the culture. Growth of hybridoma cells was observed 9 to 14 days after cell fusion. When the culture solution was turned yellow (about $1 \times 10^6$ cells/ml), the supernatant was collected and the antibody titer was determined according to the method described in Example 5.

Figure 5A:
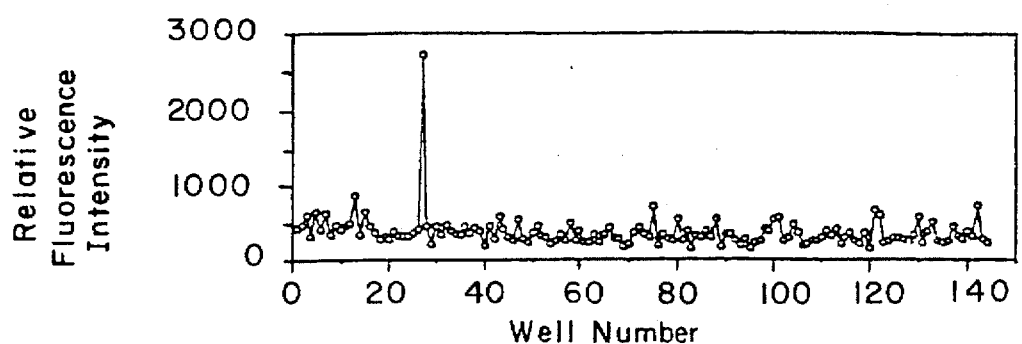
FIGS. 5(a)–5(d) show typical examples of screening of hybridomas after cell fusion. 5(a) is a case in which mice immunized with β-amyloid (1–40) were used, 5(b) is a case in which mice immunized with β-amyloid (25–35) were used, 5(c) is a case in which mice immunized with β-amyloid (1–16) were used, and 5(d) is a case in which mice immunized with β-amyloid (35–43) were used.

As a typical example of screening of the mouse-derived hybridomas immunized with β-amyloid (1–40), results obtained using mouse No. 1 (see FIG. 1) are shown in FIG. 5(a). Including this, two kinds of hybridomas were selected in total (Table 1).

TABLE 1

Reaction Specificity of Anti-β-Amyloid (23–35) and (1–40) Monoclonal Antibodies
Reactivity[1]

| Hybridoma Strain No. | Immunogen | βA(1–40) | βA(1–28) | βA(25–35) | Note |
|---|---|---|---|---|---|
| 1 | βA(1–40) | ± | – | – | BA-27 |
| 2 | βA(1–40) | ± | – | – | |
| 3 | βA(25–35) | ± | – | + | |
| 4 | βA(25–35) | ± | – | + | |
| 5 | βA(25–35) | ± | – | + | BS-85 |
| 6 | βA(25–35) | ± | – | + | |
| 7 | βA(25–35) | ± | – | + | |

[1]When 100 nM of the antigen [βA(1–40), βA(1–28) or βA(25–35)] existed,
+: (B/B$_0$) < 0.50
±: 0.50 ≦ (B/B$_0$) < 0.90
–: 0.90 ≦ (B/B$_0$)
wherein B: the amount of β-Gal-labeled βA(1–40) bound to the antibody when the antigen existed
B$_0$: the amount of β-Gal-labeled βA(1–40) bound to the antibody when the antigen did not exist.

Figure 5B:
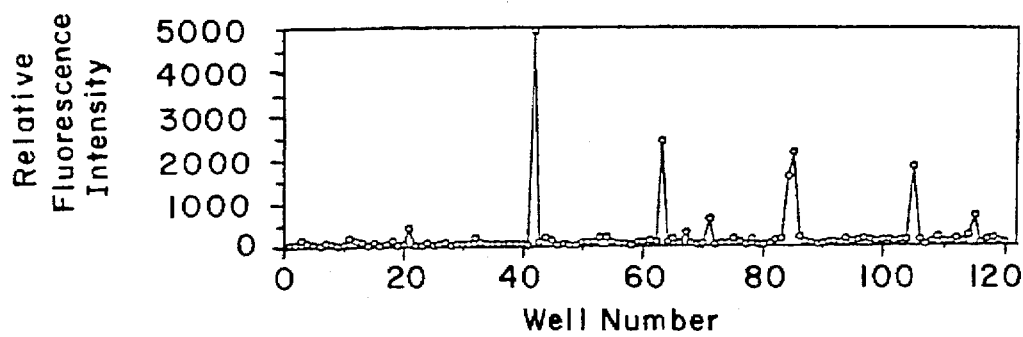

As a typical example of screening of the mouse-derived hybridomas immunized with β-amyloid (25–35), results obtained using mouse No. 8 (see FIG. 2) are shown in FIG. 5(b). Including this, five kinds of hybridomas were selected in total (Table 1).

Figure 5C:
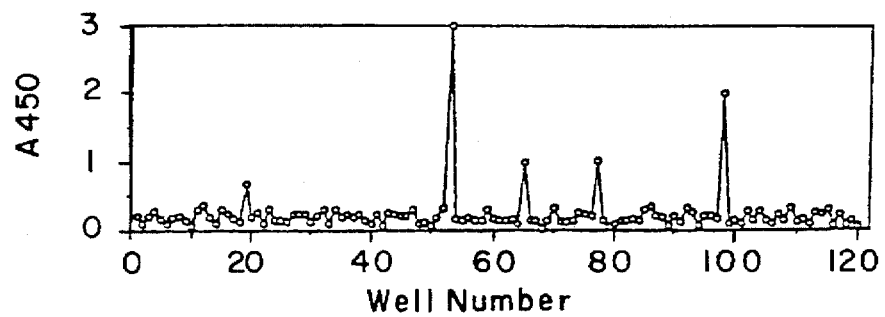

As a typical example of screening of hybridomas which are derived from mice immunized with β-amyloid (1–16), results obtained using mouse No. 5 (see FIG. 3) are shown in FIG. 5(c). Including these, 8 hybridoma strains were first selected, and thereafter 16 hybridoma strains were further selected (Table 2).

Figure 5D:
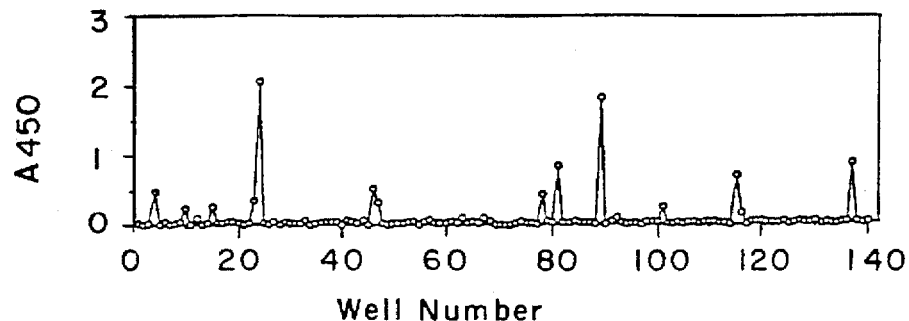

As a typical example of screening of the mouse-derived hybridomas immunized with β-amyloid (35–43), results obtained using mouse No. 4 (see FIG. 4) are shown in FIG. 5(d). Including these, eighteen kinds of hybridomas were selected in total (Table 3). Further, the mouse-derived hybridomas immunized with β-amyloid (18–28) were screened to select nine kinds of hybridomas in total (Table 4).

TABLE 2

Reactivity of Anti-β-Amyloid (1–16) Monoclonal Antibody
Reactivity[1]

| Hybridoma No. | βA(1–40) | βA(1–28) | βA(1–16) | Note |
|---|---|---|---|---|
| 1 | + | + | + | BAN-052 |
| 2 | + | + | + | BAN-11 |
| 3 | + | + | + | BAN-30 |
| 4 | ± | – | + | |
| 5 | ± | + | + | |
| 6 | + | + | + | BAN-20 |
| 7 | – | – | + | |
| 8 | – | – | + | |
| 9 | + | – | + | BAN-40 |
| 10 | + | + | + | |
| 11 | + | + | + | |
| 12 | + | + | + | BAN-50 |
| 13 | + | ± | + | |
| 15 | + | + | + | |
| 16 | ± | ± | + | |
| 17 | + | + | + | |
| 18 | + | + | + | |
| 19 | + | + | + | |
| 20 | ± | – | + | |
| 21 | – | – | + | |
| 22 | + | + | + | |
| 23 | ± | ± | + | |
| 24 | ± | | + | |

[1]When 100 nM of the antigen [βA(1–40), βA(1–28) or βA(1–16)] existed,
+: (B/B$_0$) < 0.50
±: 0.50 ≦ (B/B$_0$) < 0.80
–: 0.80 ≦ (B/B$_0$)
wherein B: the amount of β-Gal-labeled βA(1–16) bound to the antibody when the antigen existed
B$_0$: the amount of β-Gal-labeled βA(1–16) bound to the antibody when the antigen did not exist.

TABLE 3

Reactivity of Anti-β-Amyloid (35–43) Monoclonal Antibody
Reactivity[1]

| Hybridoma Strain No. | βA(35–43) | Brain Fraction | Class/Subclass | Note |
|---|---|---|---|---|
| 1 | + | – | | |
| 2 | ± | – | | |
| 3 | + | – | IgA, κ | BC-25 |
| 4 | + | – | IgG3, κ | BC-35 |
| 5 | + | + | IgG1, K | BC-05 |
| 6 | + | – | | |
| 7 | + | + | IgG1, κ | BC-15 |
| 8 | + | ± | IgG3, κ | BC-65 |
| 9 | + | – | | |
| 10 | + | ± | | |
| 11 | + | + | IgG1, κ | BC-75 |
| 12 | + | ± | | |
| 13 | + | – | IgM, κ | BC-95 |
| 14 | + | ± | | |
| 15 | + | + | IgG1, κ | BC-55 |
| 16 | + | ± | | |
| 17 | + | – | | |
| 18 | + | – | | |

[1]When 500 ng/ml of βA(35–43) or 100 μg/ml of the brain extract of patients with Alzheimer's disease existed,
+: (B/B$_0$) < 0.6
±: 0.6 ≦ (B/B$_0$) < 0.8
–: 0.8 ≦ (B/B$_0$)
wherein B: the amount of HRP-labeled βA(35–43) bound to the antibody when the antigen existed
B$_0$: the amount of HRP-labeled βA(35–43) bound to the antibody when the antigen did not exist.

TABLE 4

Reactivity of Anti-β-Amyloid (18–28) Monoclonal Antibody Reactivity[1)]

| Hybridoma Strain No. | βA(17–28) | βA(18–28) | βA(1–28) | Note |
|---|---|---|---|---|
| 1 | + | + | – | |
| 2 | – | + | – | BP-01 |
| 3 | – | + | – | BP-02 |
| 4 | + | + | – | BP-03 |
| 5 | ± | + | – | |
| 6 | + | + | – | BP-90 |
| 7 | – | + | – | |
| 8 | – | + | – | |
| 9 | ± | + | – | |

[1)]When 500 ng/ml of βA(17–28) or βA(18–28), or 1 µg of βA(1–28) existed,
+: $(B/B_0) < 0.6$
±: $0.6 \leq (B/B_0) < 0.8$
–: $0.8 \leq (B/B_0)$
wherein B: the amount of HRP-labeled βA(18–28) bound to the antibody when the antigen existed
$B_0$: the amount of HRP-labeled βA(18–28) bound to the antibody when the antigen did not exist.

Then, these hybridomas were cloned by the limiting dilution method. In cloning, the BALB/C mouse thymocytes were added as feeder cells at $5 \times 10^5$ cells per well. After cloning, each of the hybridomas was intraperitoneally given at 1 to $3 \times 10^6$ cells/mouse to mice (BALB/C) each of which had previously been given 0.5 ml of mineral oil intraperitoneally. After 6 to 20 days, the antibody-containing ascites was collected.

Each of the monoclonal antibodies was purified from the resulting ascites with a Protein-A column. That is, 6 to 20 ml of the ascites was diluted with the same amount of binding buffer (1.5M glycine containing 3.5M NaCl and 0.05% NaN₃, pH 9.0), and then subjected to a recombinant protein-A-agarose (Repligen) column previously equilibrated with the binding buffer to elute the specific antibody with elution buffer (0.1M citrate buffer containing 0.05% NaN₃, pH 3.0). The eluate was dialyzed against PBS at 4° C. for 2 days, followed by sterile filtration with a 0.22-µm filter (Millipore). The purified solution was stored at 4° C. or –80° C. The class and subclass of the monoclonal antibodies were determined by the enzyme-linked immunosorbent assay (ELISA) using a purified monoclonal antibody-binding solid phase. Namely, 100 µl of 0.1M carbonate buffer containing 2 µg/ml of the antibody (pH 9.6) was poured into each well of a 96-well microplate, followed by standing at 4° C. for 24 hours. The excess binding sites of the wells were blocked with Block Ace according to the method described in Example 5 described above, followed by examination of the class and subclass of the solidified antibody by ELISA using an isotype typing kit (Mouse-Typer™ Sub-Isotyping Kit, Bio RAD).

[Example 7] Competitive Method-Enzyme Immunoassays (1) Competitive Method-EIA (1) The reaction specificity of the monoclonal antibody prepared using β-amyloid (1–40) or β-amyloid (25–35) as the immunogen was examined by the following method. First, the antibody titer of each monoclonal antibody solution was examined according to the method described in Example 5 (1) or Example 5 (2), and the antibody concentration (about 3 to 15 ng/ml) in which the amount of the labeled material bound reached about 40% of the saturated amount bound was determined as the antibody concentration used in the competitive method-EIA. Then, 50 µl of an antibody solution diluted with buffer A to the determined concentration, 50 µl of a buffer A solution of the β-amyloids or the partial peptides thereof, namely β-amyloid (1–40) (β-amyloid (1–40) purchased from Bachem was hereinafter used for immunoassay), β-amyloid (1–28) (purchased from Peninsula) and β-amyloid (25–35), and 50 µl of β-Gal-labeled β-amyloid (1–40) described in Example 4 (1) mentioned above (100-fold dilution with buffer A) were added to each well of the anti-mouse immunoglobulin antibody-binding microplate described in Example 5 mentioned above, followed by reaction at 4° C. for 16 hours. After reaction, the plate was washed with PBS, and then the enzyme activity on the solid phase was assayed by the method described in Example 5 (2) mentioned above. Results are shown in Table 1. All the antibodies reacted with β-Gal-labeled β-amyloid (1–40), and also had reactivity to β-amyloid (1–40) (Table 1).

Figure 6A:
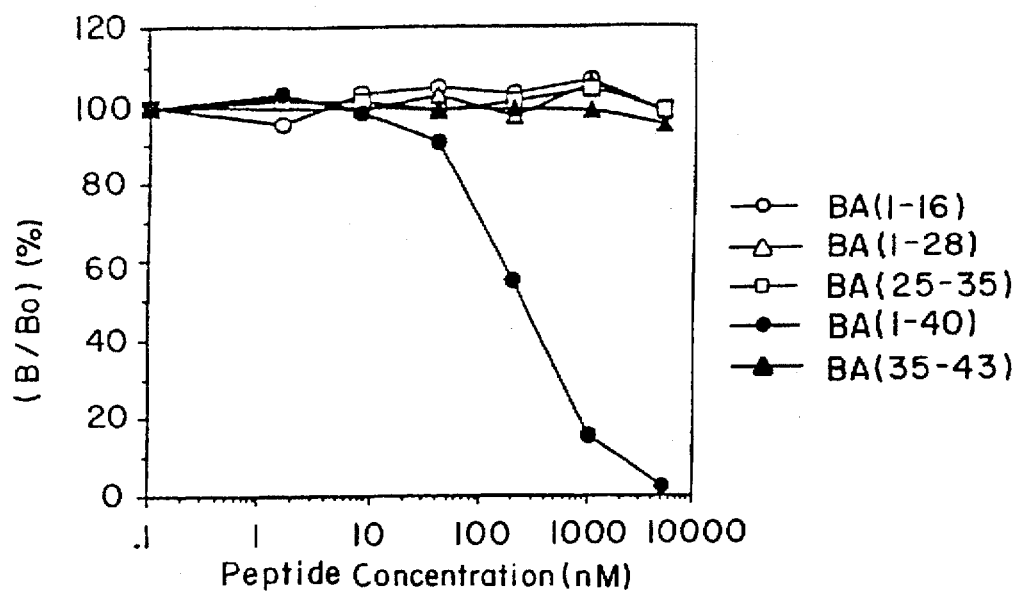
FIG. 6(a) is a graph showing the results of assay of the reactivity of monoclonal antibody BA-27a prepared using β-amyloid (1–40) as an immunogen to β-amyloid (1–40) (-●-), β-amyloid (1–28) (-Δ-), β-amyloid (1–16) (-○-), β-amyloid (25–35) (-□-) and β-amyloid (35–43) (-▲-), said reactivity being assayed by a competitive method-EIA using β-Gal-labeled β-amyloid (1–40)
Figure 6B:
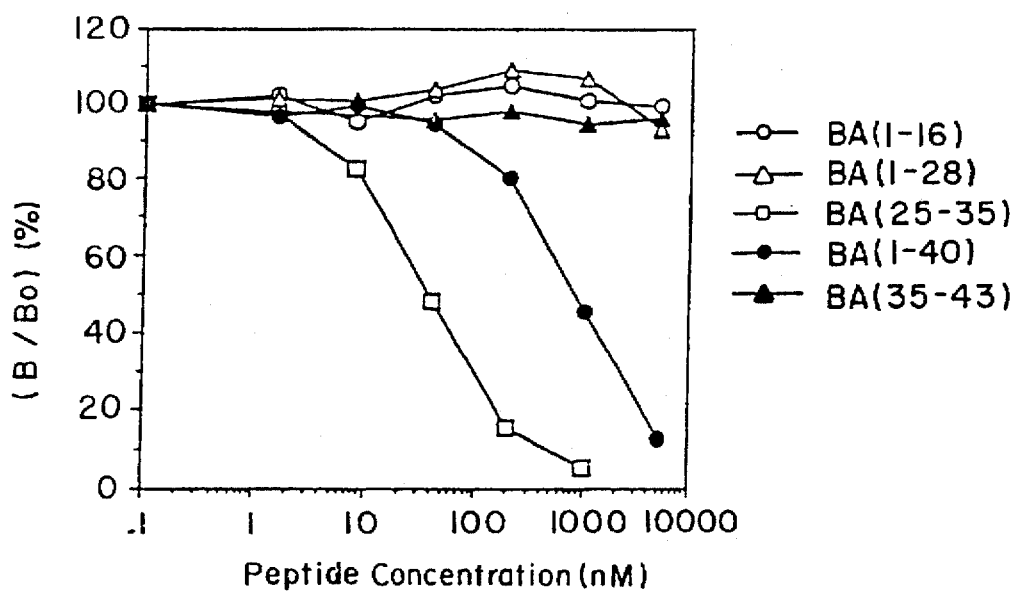
FIG. 6(b) is a graph similarly showing the results of assay of the reactivity of monoclonal antibody BS-85a prepared using β-amyloid (25–35) as an immunogen, said reactivity being assayed by a competitive method-EIA using β-Gal-labeled β-amyloid (1–40)

As typical examples, the results of the competitive method-EIA in which BA-27a (IgG2a, κ) or BS-85a (IgG1, κ) was used as an antibody to β-amyloid (1–40) or β-amyloid (25–35), respectively, are shown in FIG. 6. The standard curve of BA-27a to β-amyloid (1–40) revealed that the concentration of β-amyloid (1–40) giving $(B/B_0)=0.5$ was 200 nM, 40 ng/well. Further, this antibody did not exhibit cross reactivity to β-amyloid (1–16), β-amyloid (1–28) and β-amyloid (25–35). This proved that the antibody reacted with the partial peptide on the C-terminal side of the β-amyloid, but did not recognize the partial structure of β-amyloid (25–35) (FIG. 6(a)). On the other hand, the reactivity of BS-85a to the partial structure of β-amyloid (25–35) (antigen concentration giving $(B/B_0)=0.5$: 20 nM, 1 ng/well) was 40 times the reactivity to β-amyloid (1–40) (antigen concentration giving $(B/B_0)=0.5$: 800 µM, 160 ng/well) (FIG. 6(b)).

(2) Competitive Method-EIA (2)

Figure 7A:
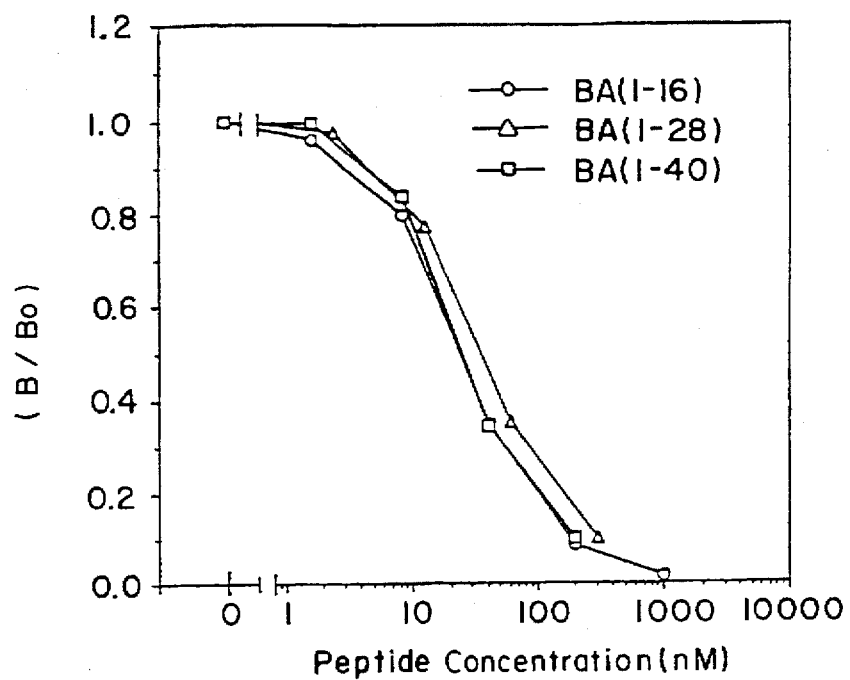
FIGS. 7(a) and 7(b) are graphs each showing the results of assay of the reactivity of monoclonal antibodies BAN-052a and BAN-50a prepared using β-amyloid (1–16) as an immunogen to β-amyloid (1–40) (-□-), β-amyloid (1–28) (-Δ-) and β-amyloid (1–16) (-○-), said reactivity being assayed by a competitive method-EIA using HRP-labeled β-amyloid (1–16)
Figure 7B:
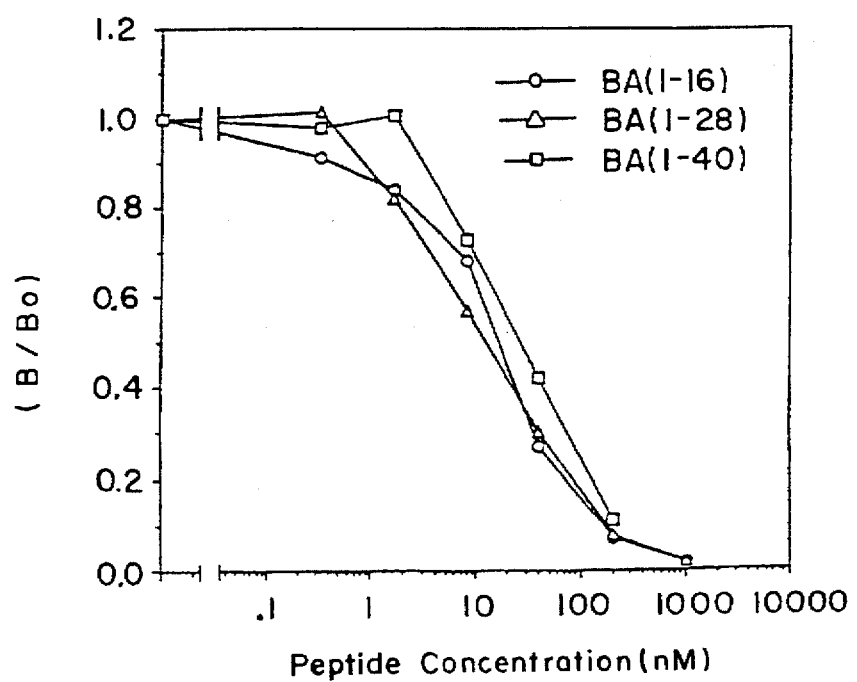
Figure 8:
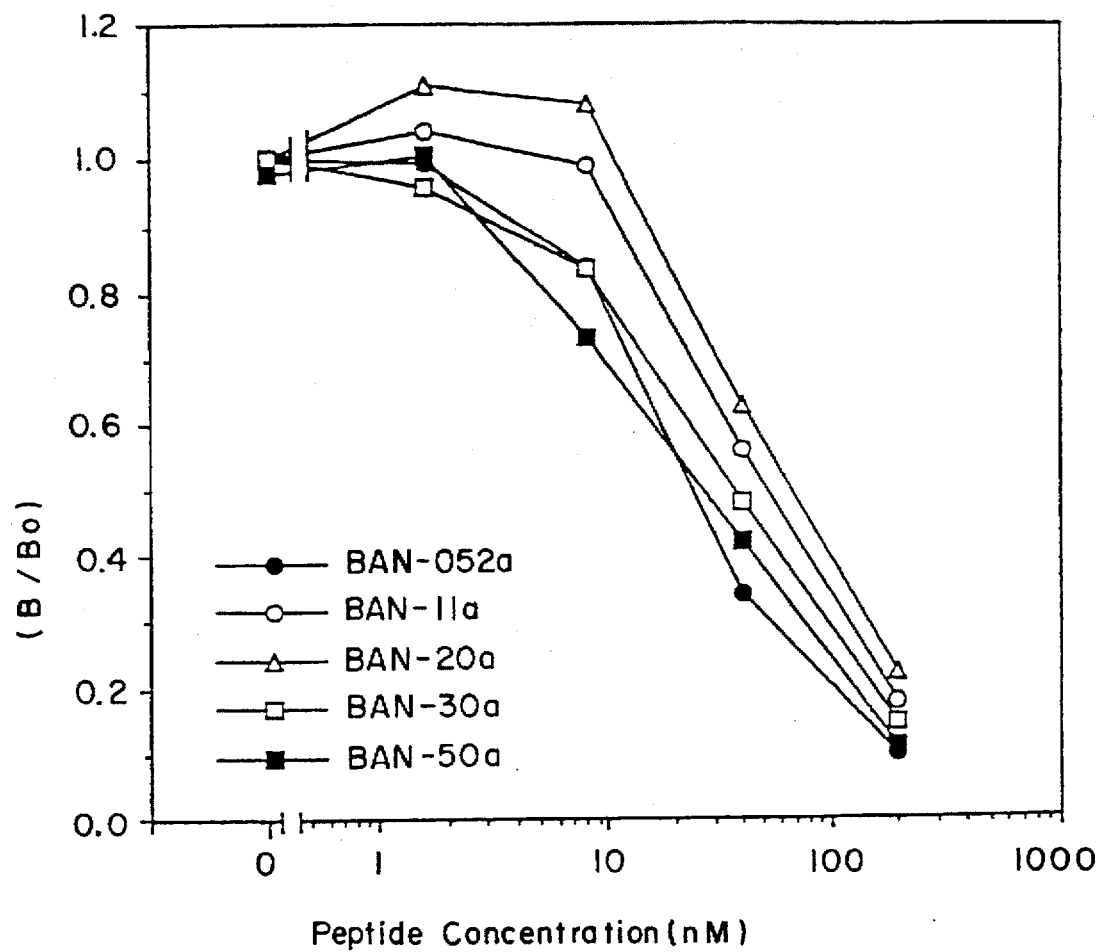
FIG. 8 is a graph showing the results of assay of the reactivity of BAN-052a (-●), BAN-11a (-○-), BAN-20a (-Δ-), BAN-30a (-□-) and BAN-50a (-■-) to β-amyloid (1–40), said reactivity being examined by a competitive method-EIA using HRP-labeled β-amyloid (1–16)

The reaction specificity of the anti-β-amyloid (1–16) monoclonal antibody was examined in a manner similar to that described above. First, the antibody titer of each monoclonal antibody solution was examined according to the method described in Example (5) 3, and the antibody concentration (about 3 to 50 ng/ml) in which the amount of the labeled material bound reached about 40% of the saturated amount bound was determined as the antibody concentration used in the competitive method-EIA. Then, 50 µl of an antibody solution diluted with buffer C to the determined concentration, 50 µl of a buffer C solution of the β-amyloids or the partial peptides thereof, namely β-amyloid (1–40), β-amyloid (1–28) and [Cys¹⁷] β-amyloid (1–16), and 50 µl of HRP-labeled β-amyloid (1–16) described in Example 4 (2) mentioned above (2000-fold dilution with buffer C) were added to each well of the anti-mouse immunoglobulin antibody-binding microplate, followed by reaction at 40C for 16 hours. After reaction, the plate was washed with PBS, and then the enzyme activity on the solid phase was assayed by the method described in Example 5 (3) mentioned above. Results are shown in Table 2. Of the eight kinds of monoclonal antibodies first selected, the four kinds thereof also reacted with β-amyloid (1–40) relatively highly, and of the sixteen kinds of monoclonal antibodies thereafter newly selected, the ten kinds thereof also reacted with β-amyloid (1–40) relatively highly (Table 2). As typical examples, the results of the competitive method-EIA of monoclonal antibodies BAN-052a (IgG1, κ) and BAN-50a (IgG1, κ) which showed the highest reactivity to β-amyloid (1–40) among these antibodies are shown in FIG. 7. FIG. 7 shows that these antibodies have a similar degree of reactivity to β-amyloid (1–40), β-amyloid (1–28) and β-amyloid (1–16). Further, β-amyloid (1–40) standard curves in the competitive method-EIA are shown in FIG. 8, in which the three kinds of monoclonal antibodies BAN-11a (IgG1, κ), BAN-20a (IgG1, κ) and BAN-30a (IgG1, κ) first selected and showing a high reactivity to β-amyloid (1–40) were used, in addition to these two kinds of antibodies. The β-amyloid (1–40) concentration of these antibodies giving $(B/B_0)=0.5$ was within the range of 25 to 70 nM (5–15 ng/well), and only a difference of less than 3 times was observed among the antibodies. Of these, the competitive method-EIA using BAN-50a was most highly sensitive, and could detect about 0.6 ng/well [$(B/B_0)=0.9$] of β-amyloid (1–40).

(3) Competitive Method-EIA (3)

From 10 g of the brain of a patient with Alzheimer's disease, 0.1 g of β-amyloid fractions (formic acid extracts) was obtained according to the method of Mori et al. (see the text). Then, according to the method described in Example 7 (2) mentioned above, the anti-mouse immunoglobulin antibody-binding microplate, the antibody solution, the β-amyloids or the partial peptide thereof, namely β-amyloid (1–40) and [$Cys^{34}$] β-amyloid (35–43) or the above-mentioned Alzheimer's disease patient's brain-derived β-amyloid fraction, and HRP-labeled β-amyloid (35–43) described in Example 4 (3) mentioned above (50-fold dilution with buffer C) were allowed to react. Results are shown in Table 3. Of the monoclonal antibodies first selected, the four kinds of antibodies relatively highly reacted with the Alzheimer's disease patient's brain-derived β-amyloid fraction. Of these, monoclonal antibody BC-05a (IgG1, κ) which exhibited a high antibody titer was selected, and used in the following experiment.

(4) Competitive Method-EIA (4)

The reaction specificity of the anti-β-amyloid (18–28) monoclonal antibody was examined by the method described in Example 7 (2) mentioned above. That is, after determination of the concentration of each antibody, reaction was conducted using β-amyloid (1–40), [$Cys^{29}$] β-amyloid (17–28) (Accord), [Cys29 ] β-amyloid (18–28) and β-amyloid (1–28) as the β-amyloids or the partial peptides thereof, and using HRP-labeled β-amyloid (18–28) described in Example 4 (4) mentioned above (1000-fold dilution with buffer C) as the labeled antigen, followed by assay of enzyme activity. Results are shown in Table 4. All of the nine kinds of antibodies selected had a high reactivity to β-amyloid (18–28) which is an antigen. Further, of these, the five kinds of antibodies relatively highly reacted also with β-amyloid (17–28). All of the antibodies did not react with β-amyloid (1–28) and β-amyloid (1–40).

Of these, monoclonal antibody BP-90a (IgG1, κ) having a high reactivity with both β-amyloid (17–28) and β-amyloid (18–28) were mainly used in the subsequent experiments.

[Example 8] Preparation of HRP-Labeled-Anti-β-Amyloid Monoclonal Antibody (1) BS-85a-HRP To 0.1M phosphate buffer (pH 6.8) containing 4.2 mg (28 nmols) of a purified BS-85a fraction was added 50 μl of DMF containing 420 nmols of GMBS, followed by reaction at room temperature for 40 minutes. The reaction solution was separated on a Sephadex G-25 column (eluent: 0.1M phosphate buffer, pH 6.7) to obtain 3 mg of a fraction of a maleimide group-introduced antibody. Then, 50 μl of DMF containing 4.5 μmols of SPDP was added to 1.4 ml of 0.02M phosphate buffer (containing 0.15M NaCl, pH 6.8) containing 12 mg (300 nmols) of HRP, followed by reaction at room temperature for 40 minutes. Then, 0.5 ml of 0.2M acetate buffer (pH 4.5) containing 68 μmols of dithiothreitol was added thereto and allowed to react for 20 minutes at room temperature, followed by separation on a Sephadex G-25 column (eluent: 0.1M phosphate buffer containing 2 mM EDTA, pH 6) to obtain 8 mg of SH group-introduced HRP. Subsequently, 8 mg of SH group-introduced HRP was mixed with 3 mg of the fraction of the maleimide group-introduced antibody, and the mixture was concentrated by a collodion bag (Sartorius) to about 0.3 ml, followed by standing at 4° C. for 16 hours. The reaction solution was subjected to an Ultrogel AcA34 column in which 0.1M phosphate buffer (pH 6.5) was used as an eluent, thereby purifying a BS-85a-HRP complex fraction.

(2) BA-27a-HRP

Using 4.7 mg of a purified BA-27a fraction and 14 mg of HRP, a BA-27a-HRP complex fraction was prepared in a similar manner.

(3) BAN-052a-HRP

Using 5 mg of a purified BAN-052a fraction and 14 mg of HRP, a BAN-052a-HRP complex fraction was prepared in a similar manner.

(4) BC-05a-HRP

Using 5 mg of a purified BC-05a fraction and 14 mg of HRP, a BC-05a-HRP complex fraction was prepared in a similar manner.

[Example 9] Sandwich Method-EIA (1)

(1) Sandwich Method-EIA Using BS-85a-HRP

Into each well of a 96-well microtiter plate was poured 100 μl of 0.1M carbonate buffer (pH 9.6) containing purified monoclonal antibody BAN-052a, BAN-11a, BAN-20a, BAN-30a, BS-85a or BA-27a described in Example 6 mentioned above, followed by standing at 4° C. for 24 hours. Then, 300 μl of Block Ace diluted 4 times with PBS was added to inactivate excess binding sites of the wells.

Figure 9:
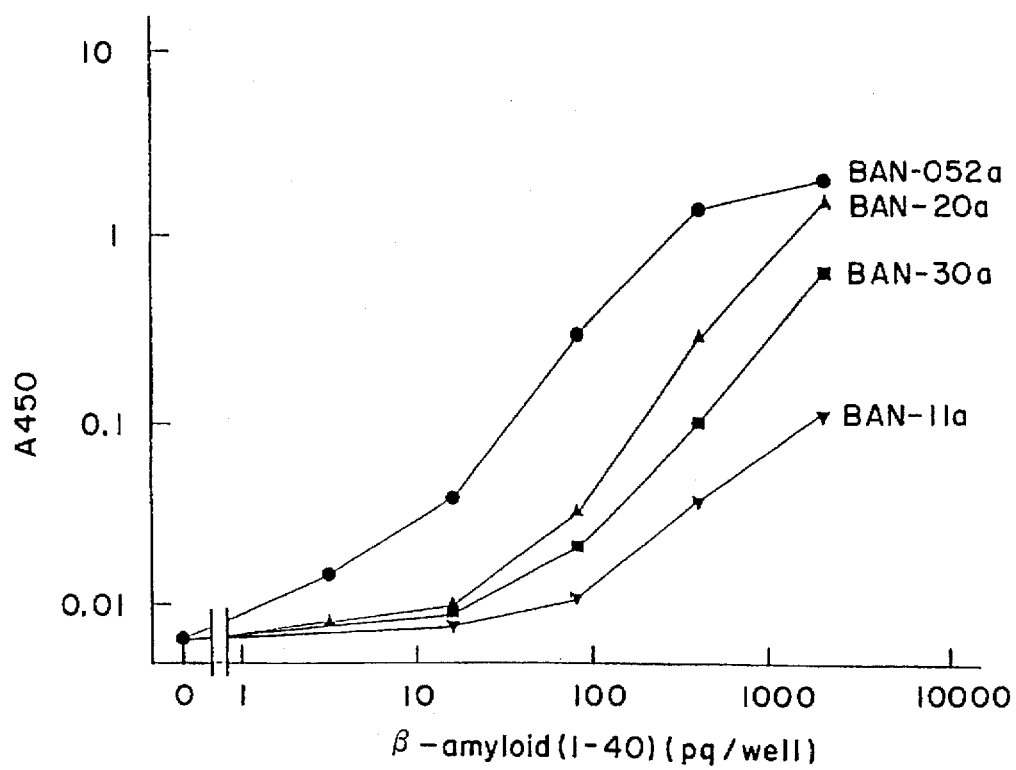
FIG. 9 is a graph showing standard curves of β-amyloid (1–40) in a sandwich EIA using BS-85a-HRP as an enzyme-labeled antibody, and BAN-052a (-●), BAN-11a (-▼-), BAN-20a (-▲-) or BAN-30a (-■-) as antibodies for solid phases.

To the plate prepared as described above was added 100 μl of a standard solution of β-amyloid (1–40) diluted with buffer E (0.02M phosphate buffer containing 10% Block Ace, 0.2% BSA, 0.4M NaCl, 0.05% CHAPS and 0.05% $NaN_3$), followed by reaction at 4° C. for 24 hours. After washing with PBS, 100 μl of BS-85a-HRP prepared in Example 8 (1) (1500-fold dilution with buffer C) was added, followed by reaction at 4° C. for 24 hours. After washing with PBS, the enzyme activity on the solid phase was assayed using TMB by the method described in Example 5 (3) mentioned above (enzyme reaction: 20 minutes). Results are shown in FIG. 9. As described in Example 7, the reactivity of BS-85a to β-amyloid (1–40) in the competitive method-EIA is not so high. However, when used as the labeled antibody in the sandwich method-EIA in which the monoclonal antibody using β-amyloid (1–16) as the antigen was in the solid phase as described above, it detected β-amyloid (1–40) with an extremely high sensitivity. In particular, the use of the solid phase of BAN-052a resulted in a sensitivity 10 to 30 times higher than that of the other three kinds of antibody solid phases, and it was possible to detect 3 pg/well of β-amyloid (1–40).

(2) Sandwich Method-EIA Using BA-27a-HRP

Figure 10:
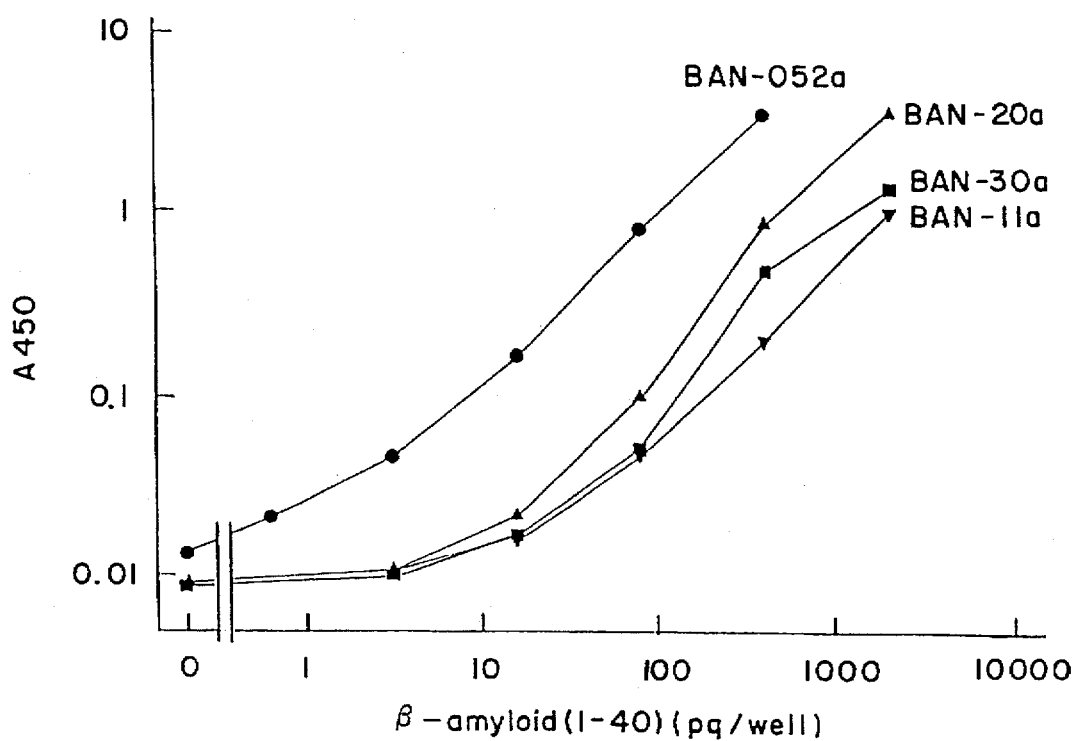
FIG. 10 is a graph showing standard curves of β-amyloid (1–40) in a sandwich EIA using BA-27a-HRP as an enzyme-labeled antibody, and BAN-052a (-●), BAN-11a (-▼-), BAN-20a (-▲-) or BAN-30a (-■-) as antibodies for solid phases.

Similarly, 100 μl of the standard solution of β-amyloid (1–40) was added to the microplate to which BAN-052a, BAN-11a, BAN-20a, BAN-30a, BS-85a or BA-27a was fixed, followed by reaction at 4° C. for 24 hours. After washing with PBS, 100 μl of BA-27a-HRP prepared in Example 8 (2) described above (2500-fold dilution with buffer C) was added, followed by reaction at 4° C. for 24 hours. After washing with PBS, the enzyme activity on the solid phase was assayed using TMB (enzyme reaction: 20 minutes). Results are shown in FIG. 10. Similarly with BS-85a, BA-27a did not show a high reactivity to β-amyloid (1–40) in the competitive method-EIA. However, when used as the labeled antibody in the sandwich method-EIA as described above, it detected β-amyloid (1–40) with a sensitivity higher than BS-85a. In particular, the use of the solid phase of BAN-052a resulted in a sensitivity about 30 times higher than that of the other three kinds of antibody solid phases, and it was possible to detect 0.6 pg/well of β-amyloid (1–40).

(3) Sandwich Method-EIA Using BAN-052a-HRP

Figure 11:
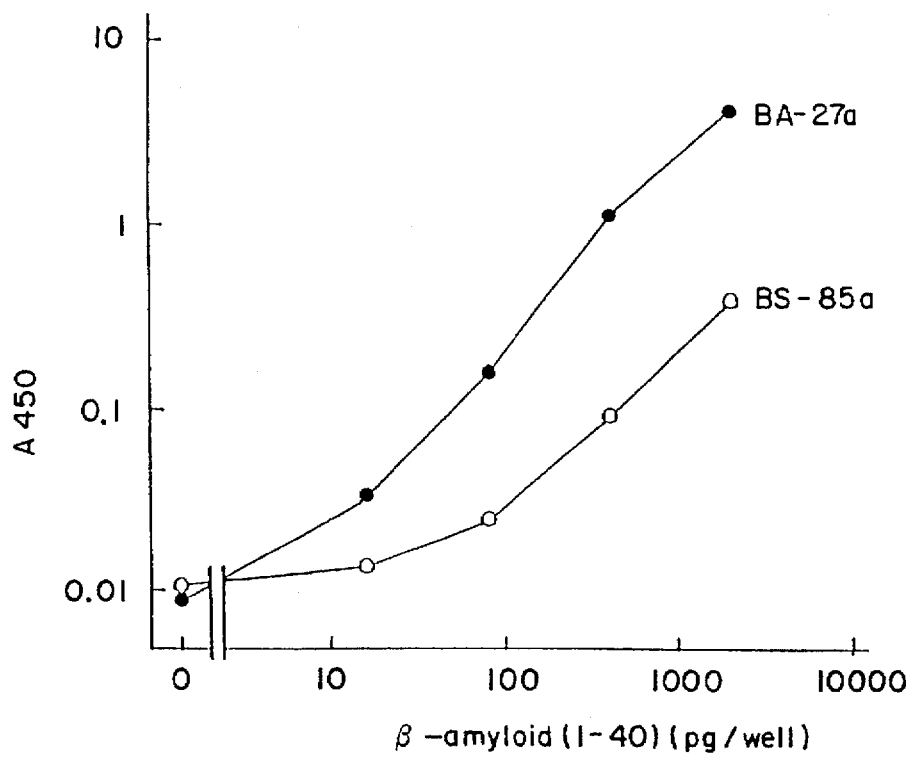
FIG. 11 is a graph showing standard curves of β-amyloid (1–40) in a sandwich EIA using BAN-052a-HRP as an enzyme-labeled antibody, and BA-27a (-●) or BS-85a (-○-) as antibodies for solid phases.

To the microplate to which BS-85a or BA-27a was fixed, 100 μl of the standard solution of β-amyloid (1–40) was added, followed by reaction at 4° C. for 24 hours. After washing with PBS, 100 μl of BAN-052a-HRP prepared in Example 8 (3) described above (2500-fold dilution with buffer C) was added, followed by reaction at 4° C. for 24 hours. After washing with PBS, the enzyme activity on the solid phase was assayed using TMB (enzyme reaction: 20 minutes). Results are shown in FIG. 11. Thus, also in the system constructed reversely to that of Example 8 (2), namely in the sandwich method-EIA in which the C-terminal antibody such as BS-85a or BA-27a was used as the solid phase and the N-terminal antibody, BAN-052a, was used as the labeled material, it was possible to detect 80 pg/well and 10 pg/well of β-amyloid (1–40), respectively.

Figure 12:
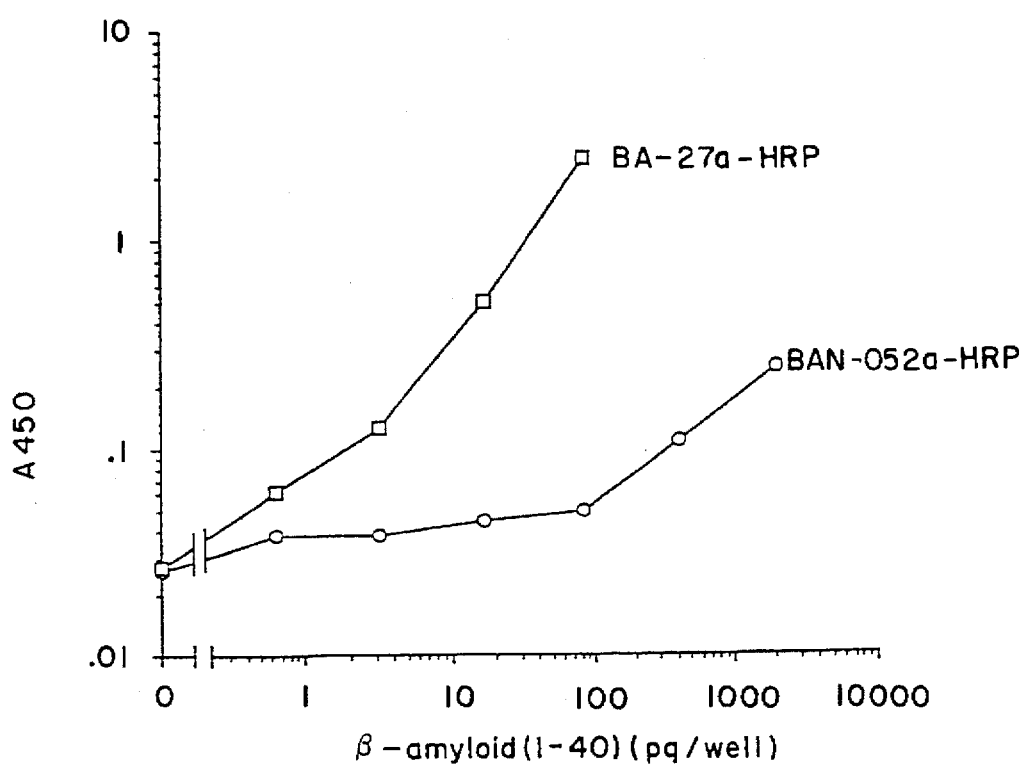
FIG. 12 is a graph showing standard curves of β-amyloid (1–40) in a sandwich EIA using BAN-052a-HRP (-○-) or BA-27a-HRP (-□-) as enzyme-labeled antibodies, and BAN-052a as an antibody for solid phases.

Further, when BAN-052a-HRP (1000-fold dilution with buffer C) was also used as the labeled material in the sandwich method-EIA using BAN-052a as the solid phase, the detection sensitivity fell to 1/100, compared with the case that BA-27a-HRP (1500-fold dilution with buffer C) was used. This suggests that a multimer of β-amyloid (1–40), scarcely exists under the experimental conditions used in the present invention (FIG. 12).

[Example 10] Sandwich Method-EIA (2)

Figure 13:
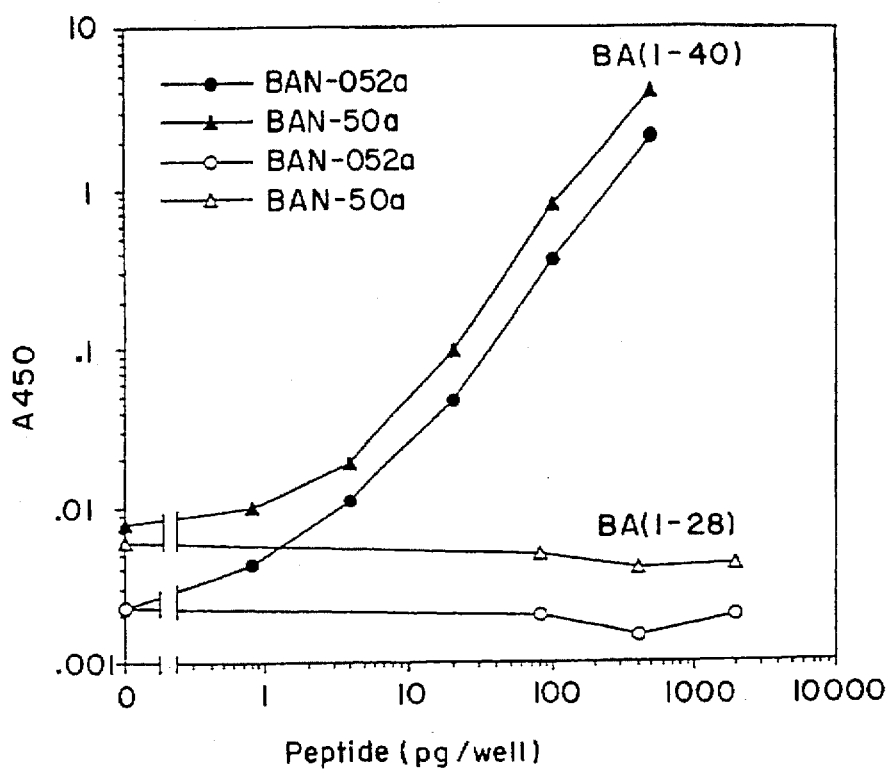
FIG. 13 is a graph showing standard curves of β-amyloid (1–40) (-●▲-) or β-amyloid (1–28) (-○, Δ-) in a sandwich EIA using BS-85a-HRP as an enzyme-labeled antibody, and BAN-052a (-□, ○-) or BAN-50a (-▼, Δ-) as antibodies for solid phases.
Figure 14:
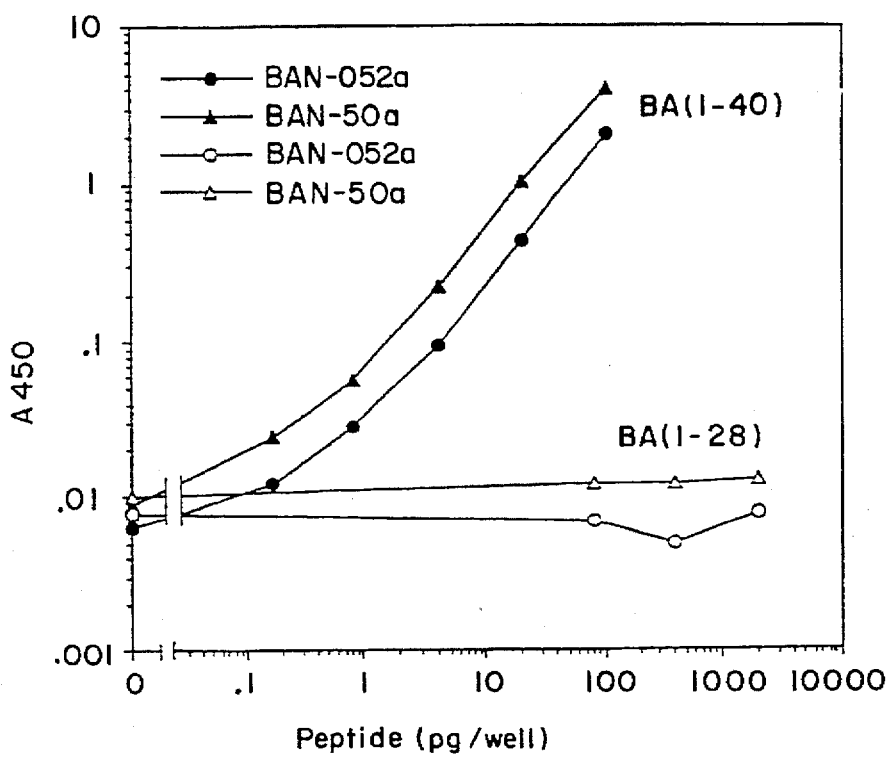
FIG. 14 is a graph showing standard curves of β-amyloid (1–40) (-●▲-) or β-amyloid (1–28) (-○, Δ-) in a sandwich EIA using BA-27a-HRP as an enzyme-labeled antibody, and BAN-052a (-●○-) or BAN-50a (-▲, Δ-) as antibodies for solid phases.

From the fact that, of the anti-β-amyloid (1–16) monoclonal antibodies, BAN-052a provided the sandwich method-EIA having an extremely high sensitivity, sixteen kinds of antibodies were further prepared to select anti-β-amyloid (1–16) monoclonal antibodies more suitable for the sandwich method-EIA (Table 2). As a result, BAN-50a was obtained. Results of the sandwich method-EIA using BAN-50a as the solid antibody are shown in FIG. 13 and FIG. 14. Although the assay was conducted according to Example 9 (3) described above, 1000-fold dilution (FIG. 13) was used as the concentration of the labeled material for BS-85a-HRP, and 1500-fold dilution (FIG. 14) for BA-27a-HRP. Further, in order to examine the specificity of these assay systems, the reactivity to β-amyloid (1–28) was also examined [in the figures, ● and ▲ indicate the reactivity to β-amyloid (1–40), and ○ and △ indicate the reactivity to β-amyloid (1–28)]. As a result, even when either of the labeled materials was used, the sensitivity for the BAN-50a solid phase was 2 to 3 times higher than that for the BAN-052a solid phase. When it was combined with the BA-27a-HRP labeled material, it was possible to detect 0.2 pg/well of β-amyloid (1–40). Further, the results showed that all the assay systems did not detect β-amyloid (1–28), and was specific for β-amyloid (1–40).

Figure 15A:
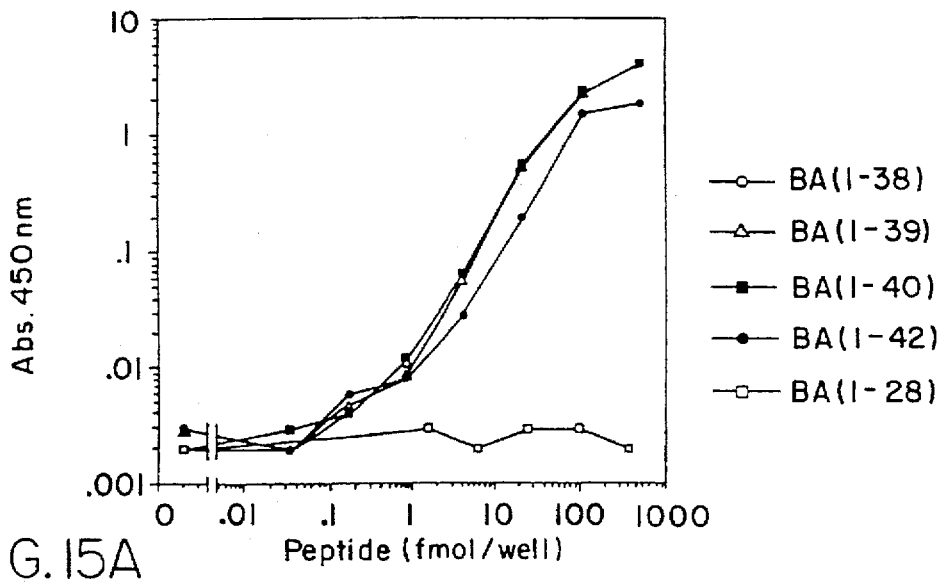
FIGS. 15(a)–15(c) show standard curves of β-amyloid (1–38) (-○-), β-amyloid (1–39) (-Δ-), β-amyloid (1–40) (-■-), β-amyloid (1–42) (-●) or β-amyloid (1–28) (-□-) in a sandwich EIA using 15(a) BS-85a-HRP, 15(b) BA-27a-HRP or 15(c) BC-05a-HRP as enzyme-labeled antibodies, and BAN-50a as an antibody for solid phases.
Figure 15B:
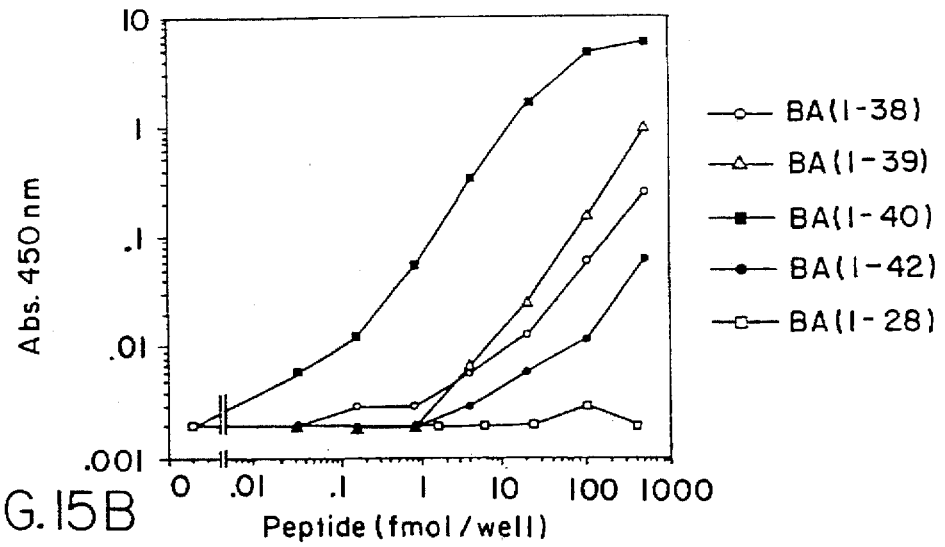

[Example 11] Sandwich Method-EIA (3)
(1) Specificity of Sandwich Method-EIA Using BS-85a-HRP or BA-27a-HRP The specificity of two kinds of sandwich method-EIA systems was examined in more detail in which BAN-50a was used as a solid phase antibody and BS-85a-HRP or BA-27a-HRP was used as a labeled material. Although the assay was conducted according to Example 10 described above, 670-fold dilution was used as the concentration of the labeled material for BS-85a-HRP, and 1000-fold dilution for BA-27a-HRP, and the reactivity to β-amyloid (1–38), β-amyloid (1–39), β-amyloid (1–40), β-amyloid (1–42) and β-amyloid (1–28) was examined (FIGS. 15(a) and 15(b)) wherein β-amyloid (1–38) and β-amyloid (1–39) prepared in Example 1 (5) were used. The concentration of β-amyloid (1–38) and β-amyloid (1–39) in respective fractions of reverse-phase HPLC corresponding thereto in Example 1 (5) was determined by the competitive method-EIA using BAN-50a according to the method of Example 7 (2). Results revealed that the assay system using BS-85a-HRP as the labeled material (FIG. 15(a)) detected β-amyloid (1–38), β-amyloid (1–39) and β-amyloid (1–40) with an almost similar sensitivity (0.7 pg/well), and that it detected β-amyloid (1–42) with a sensitivity one-half to one-third that of the above-mentioned three kinds of β-amyloids. Furthermore, β-amyloid (1–28) was not detected at all, giving results similar to those of Example 10. On the other hand, the assay system using BA-27a-HRP as the labeled material (FIG. 15(b)) detected β-amyloid (1–40) and β-amyloid (1–42) with sensitivities of 0.2 pg/well and 18 pg/well, respectively. Further, for β-amyloid (1–38) and β-amyloid (1–39), it was possible to detect with sensitivities of 85 pg/well and 17 pg/well, respectively.

Figure 15C:
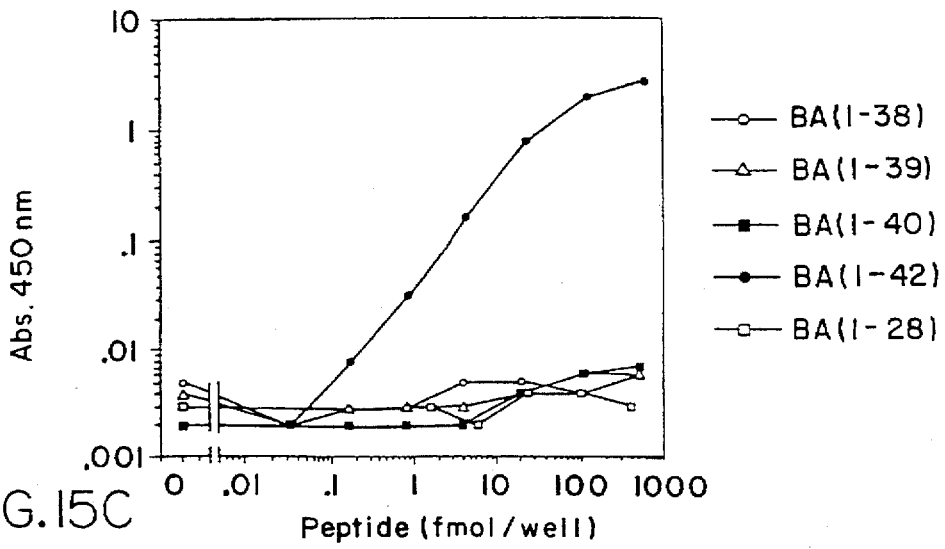

The above-mentioned results showed that the assay system using BS-85a-HRP as the labeled material was nonspecific for the C-terminal portions of the β-amyloids, and that it was approximately equivalently sensitive to the β-amyloids containing the sequence of β-amyloid (25–35) which was a partial peptide used as the immunogen to the labeled antibody. On the other hand, the assay system using BA-27a-HRP as the labeled material was considered to be specific for the C-terminus of β-amyloid (1–40), and weakly reacted to β-amyloid (1–38), 0-amyloid (1–39) and β-amyloid (1–42) with a-cross reactivity of 2% or less. (2) Specificity and Sensitivity of Sandwich Method-EIA Using BC-05a-HRP The specificity and sensitivity of a sandwich method-EIA was examined in which BAN-50a was used as a solid antibody and BC-05a-HRP prepared in Example 8 (4) described above was used as a labeled material. The reactivity to β-amyloid (1–38), β-amyloid (1–39), β-amyloid (1–40), β-amyloid (1–42) and β-amyloid (1–28) was examined in the same manner as with Example 11 (1) described above with the exception that 200-fold dilution was used as the concentration of the labeled material (FIG. 15(c)). As a result, the sandwich method-EIA using BC-05a-HRP could detect 0.7 pg/well of β-amyloid (1–42), but it did not detect the four kinds of β-amyloids other than β-amyloid (1–42), namely β-amyloid (1–38), β-amyloid (1–39), β-amyloid (1–40) and β-amyloid (1–28), at all. Hence, this proved that the sandwich method-EIA using BAN-50a as the solid antibody and BC-05a-HRP as the labeled material could detect β-amyloid (1–42) with an extremely high sensitivity and selectivity.

The above-mentioned results showed that β-amyloid (1–40) and β-amyloid (1–42) could be separately determined by combining the two kinds of assay systems in which BAN-50a was used as the solid antibody and BA-27a-HRP or BC-05a-HRP was used as the labeled material.

[Example 12] Preparation of Monoclonal Antibody-Fixed Affinity Solid Phase.

(1) Preparation of BAN-052a-Fixed Affinity Solid Phase

BAN-052a was fixed to a resin, thereby preparing an affinity solid phase. Namely, 45 mg of BAN-052a was allowed to react with 5 g of TSKgel AF-Trecyltoyopearl 650M (Toso) in a 0.1M aqueous solution of sodium hydrogencarbonate containing 0.5M NaCl, overnight at 4° C.

After reaction, the product was washed with 0.5M saline, and allowed to react in 0.1M Tris-HCl (pH 8.0) containing 0.5M NaCl at room temperature for 1 hour to block excess active groups. Then, 25 ml of BAN-052a-Trecyltoyopearl thus obtained was washed with PBS, followed by storage in buffer E at 4° C.

(2) Preparation of BA-27a Fixed Affinity Solid Phase

Similarly to (1) described above, BA-27a was fixed to a filler, thereby preparing an affinity solid phase. Namely, 15 mg of BA-27a was allowed to react with 2 g of TSKgel AF-Trecyltoyopearl 650M to obtain 10 ml of BA-27a-Trecyltoyopearl.

[Example 13] Analysis of β-Amyloids Contained in Cerebrospinal Fluid of Patient with Alzheimer's Disease The cerebrospinal fluid of a patient with Alzheimer's disease purified by the use of the BAN-052a fixed affinity solid phase prepared in Example 12 (1) described above was fractionated by reverse-phase HPLC, and analyzed by the sandwich-EIA.

Figure 16A:
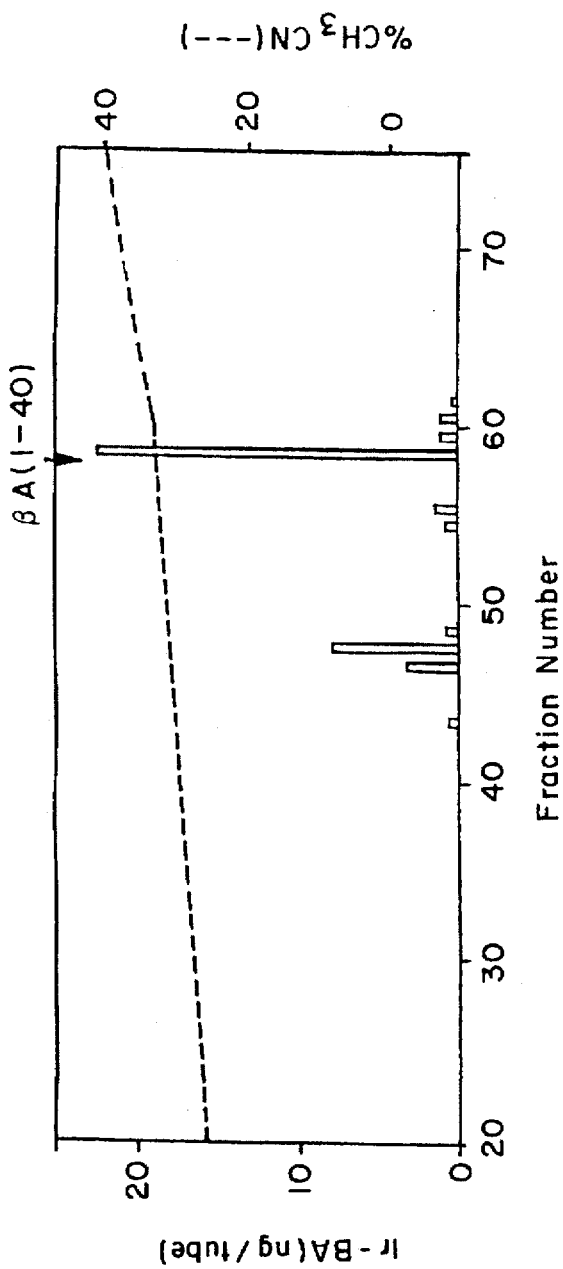
FIGS. 16(a) and 16(b) show the results of assay of the immunological activity of β-amyloids fractions eluted from the cerebrospinal fluid of patients with Alzheimer's disease by reverse-phase HPLC, said immunological activity being assayed by a sandwich EIA using 16(a) BS-85a-HRP and 16(b) BA-27a-HRP as enzyme-labeled antibodies, and BAN-50a as an antibody for solid phases.
Figure 16B:
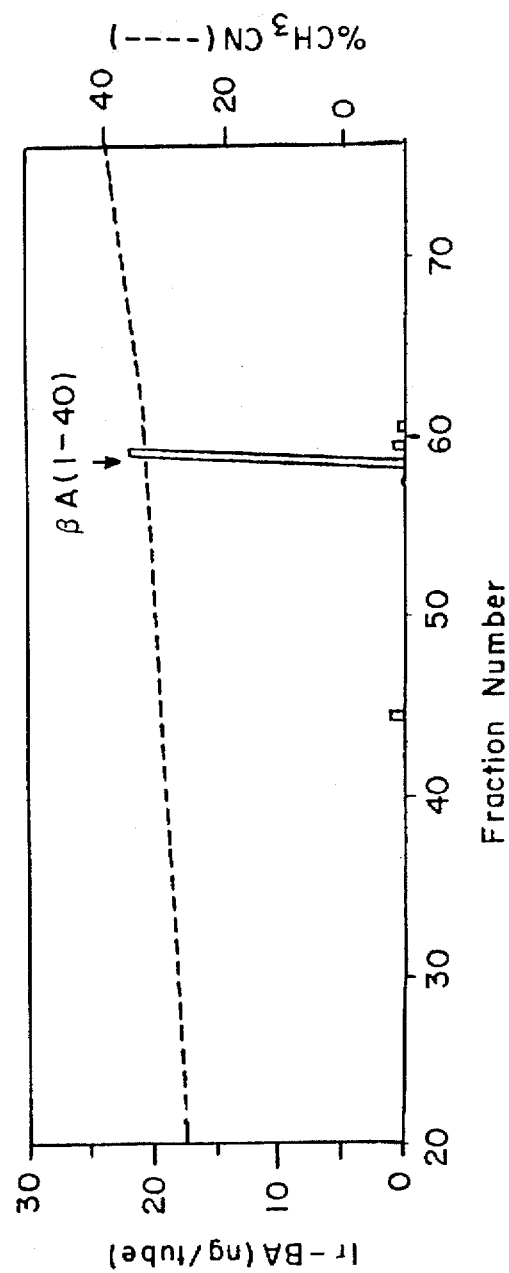

First, 1.5 ml of the cerebrospinal fluid of a patient with Alzheimer's disease was diluted twice with buffer E, followed by elution from a column (0.8×0.3 cm) filled with BAN-052a-Trecyltoyopearl for partial purification. As an eluent, 60% acetonitrile containing 0.2% trifluoroacetic acid was used. Then, after concentration, these eluted fractions were separated by reverse-phase HPLC using Vydac C4 according to the method described in Example 1 (5), and β-amyloids contained in the eluted fractions were determined by the sandwich method-EIA using the BAN-50a binding solid phase and BS-85a-HRP or BA-27a-HRP described in Example 10. Results are shown in FIG. 16. Fraction No. 59 approximately agreed with the elution position of synthetic β-amyloid (1–40), so that the immunological activity detected in both of FIGS. 16(a) and 16(b) was considered to be that to β-amyloid (1–40). The results of FIG. 16 therefore showed that β-amyloid (1–40) existed at a high concentration in the cerebrospinal fluid of the patient with Alzheimer's disease. FIG. 16(a) further revealed that molecular species which were detectable with BS-85a-HRP alone were also contained in small amounts (fraction Nos. 47 and 48). These are eluted at acetonitrile concentrations lower than that at which β-amyloid (1–40) was eluted. Accordingly, materials eluted in fraction Nos. 47 and 48 are considered to be molecular species more hydrophilic than β-amyloid (1–40). The results of Example 11 showed that the assay system using BS-85a-HRP as the labeled material was also sensitive to a molecular species lacking one or two residues from the C-terminus of β-amyloid (1–40), equivalently to β-amyloid (1–40). The possibility is therefore high that the immunological activity observed in fraction Nos. 47 and 48 is that to the molecular species lacking the C-terminal portion of β-amyloid (1–40).

[Example 14] Analysis of β-Amyloids Fractions Derived from Cerebrospinal Fluid of Patient with Alzheimer's Disease In formic acid was dissolved 11 mg of the Alzheimer's disease patient's brain-derived β-amyloid fractions (the formic acid extracts) described in Example 7 (3) mentioned above, and separated by gel filtration using TSK G3000PW.

Figure 17:
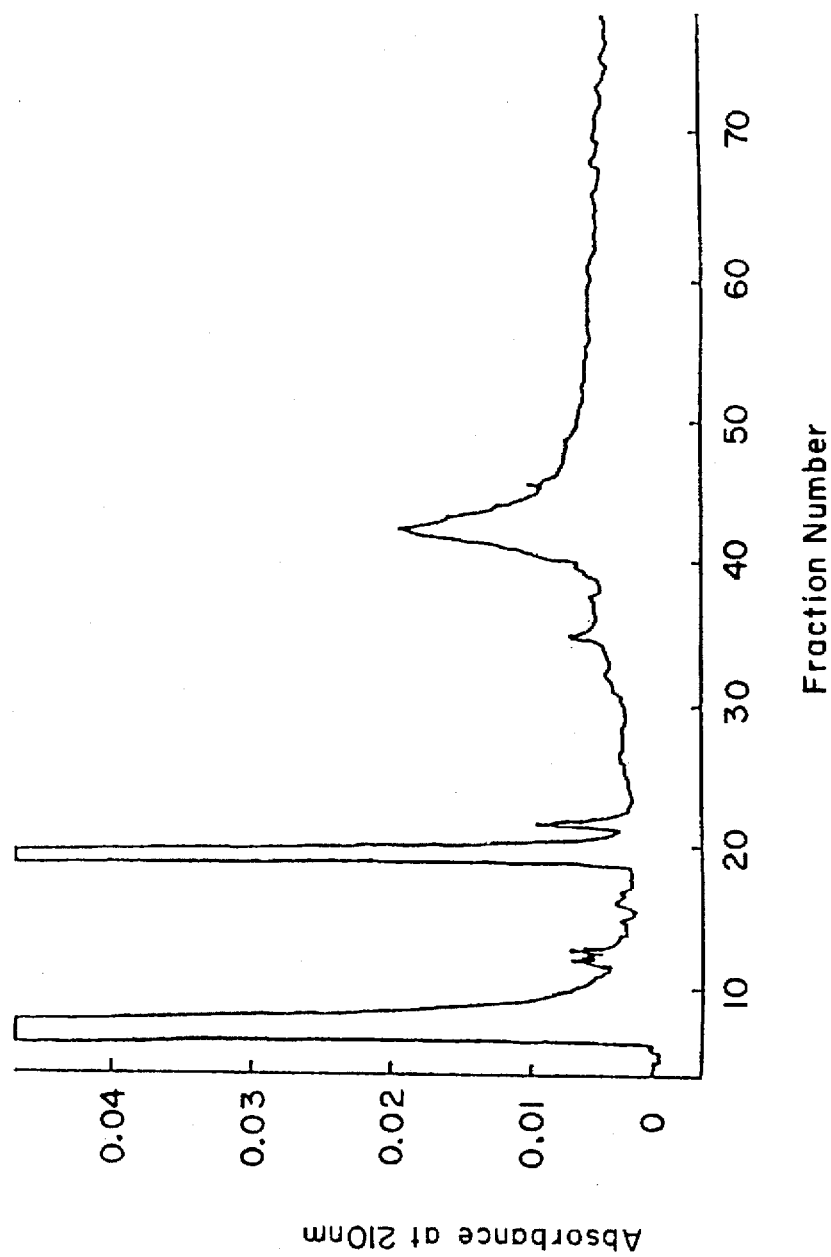
FIG. 17 shows the results of fractionation of Alzheimer's disease patient-derived β-amyloid fractions (formic acid extracts) by reverse-phase HPLC (detection wavelength: 210 nm) after partial purification by gel filtration.
Figure 18A:
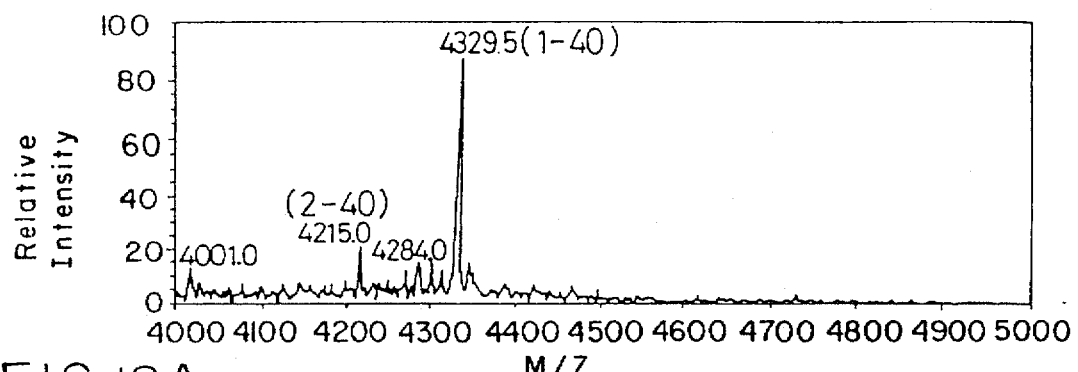
FIGS. 18(a)–18(d) show mass spectra of 18(a) No. 35, 18(b) No. 41 and 18(c) (M/Z: 4000 to 5000) and 18(d) (M/Z: 2000 to 5000) No. 43 of the eluted fractions by reverse-phase HPLC in FIG. 17 of Alzheimer's disease patient's brain-derived β-amyloid fractions (formic acid extracts)
Figure 18B:
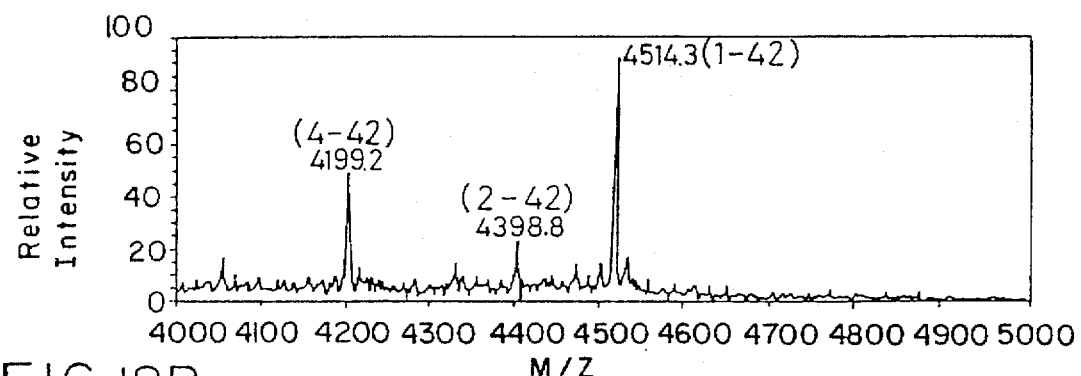
Figure 18C:
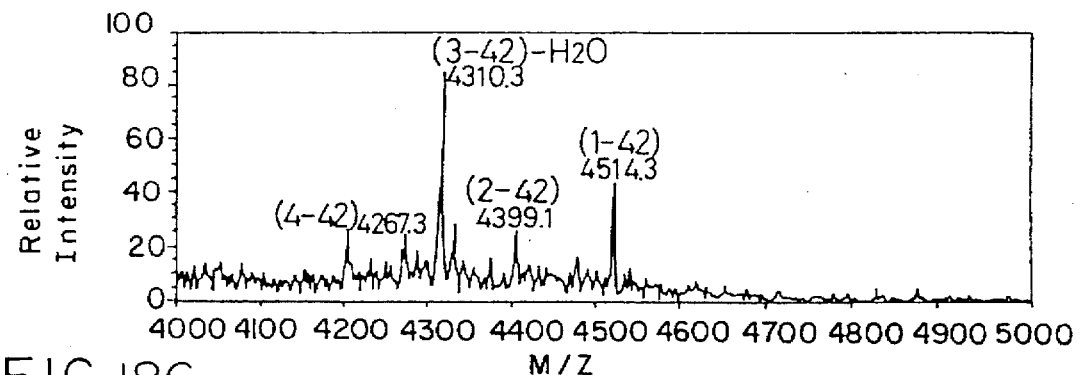
Figure 18D:
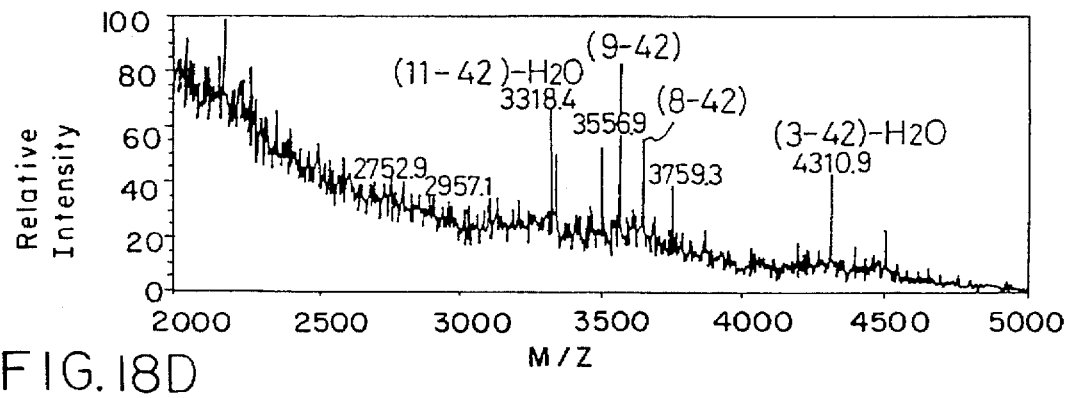

Column conditions
Column: TSK G3000PW (Toso)
Eluents: 40% acetonitrile containing 0.1% trifluoroacetic acid Flow rate: 0.5 ml/minute β-Amyloids contained in the eluted fractions were by the sandwich method-EIA using BAN-50a antibody binding solid phase and BS-85a-HRP described in Example 10 mentioned above. As a result, a high immunological activity was observed between 14 minutes and 15 minutes of HPLC elution time. Then, 0.05% CHAPS was added to this fraction, followed by concentration, and separation was conducted by reverse-phase HPLC using Vydac C4 according to the method described in Example 1 (5). Results of elution are shown in FIG. 17.

After 300 μl of each of the resulting fractions of No. 35 and Nos. 41 to 45 was concentrated, the concentrated fractions were subjected to mass spectrometry (HX110, JEOL). Results of analysis for the fractions of No. 35, No. 41 and No. 43 are shown in FIG. 18. β-Amyloid (1–40) was the major constituent for No. 35, β-amyloid (1–42) for No. 41. For No.43, β-amyloid (3–42) was the major constituent (the N-terminal of β-amyloid (3–42) was estimated to be converted to pyroglutamic acid, because the molecular weight was smaller by 18 than expected). Further, No.43 contained other minor molecular species lacking the N-terminal portions as mixtures. Furthermore, the elution position of No. 35 agreed with that of synthetic β-amyloid (1–40).

Figure 19A:
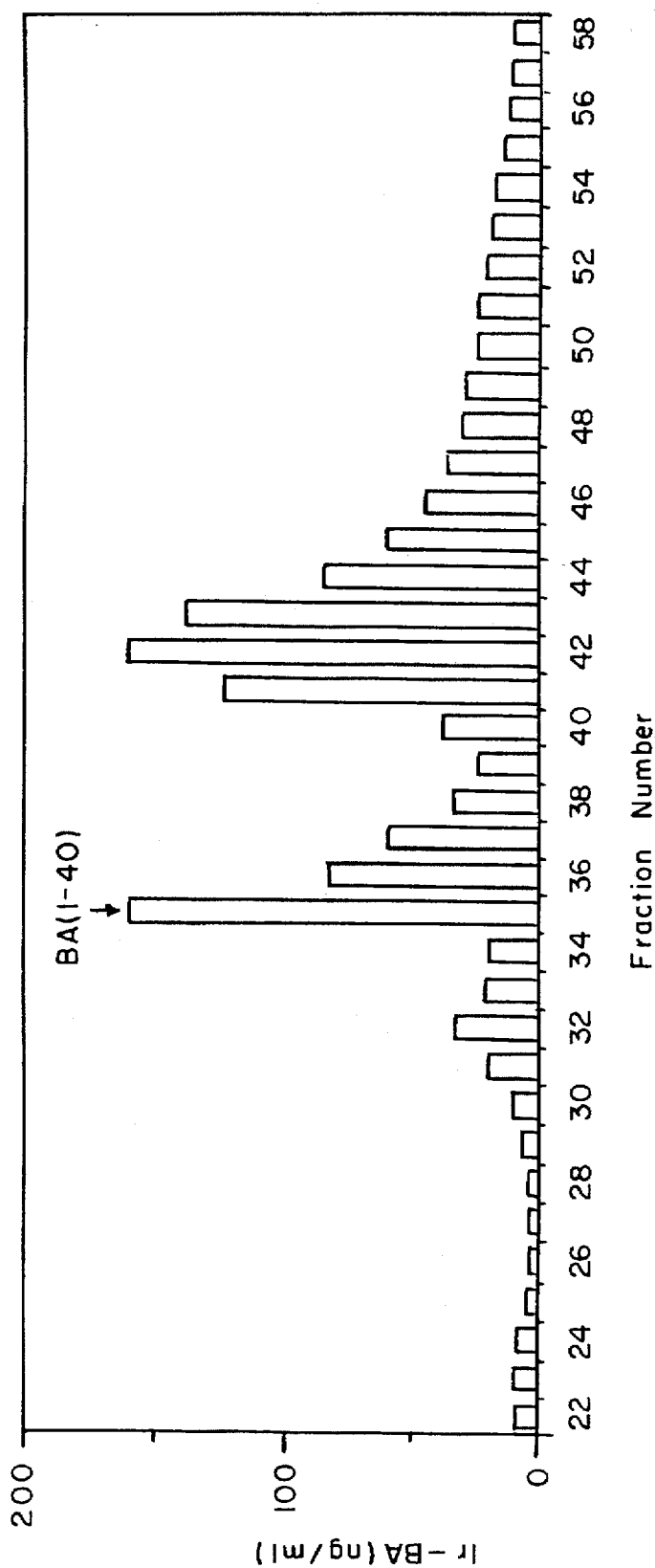
FIGS. 19(a)–19(c) show the results of determination of the eluted fractions by reverse-phase HPLC in FIG. 17 of Alzheimer's disease patient's brain-derived β-amyloid fractions (formic acid extracts), said determination being conducted by a sandwich EIA using 19(a) BS-85a-HRP, 19(b) BA-27a-HRP and 19(c) BC-05a-HRP as enzyme-labeled antibodies, and BAN-50a as an antibody for solid phases.
Figure 19B:
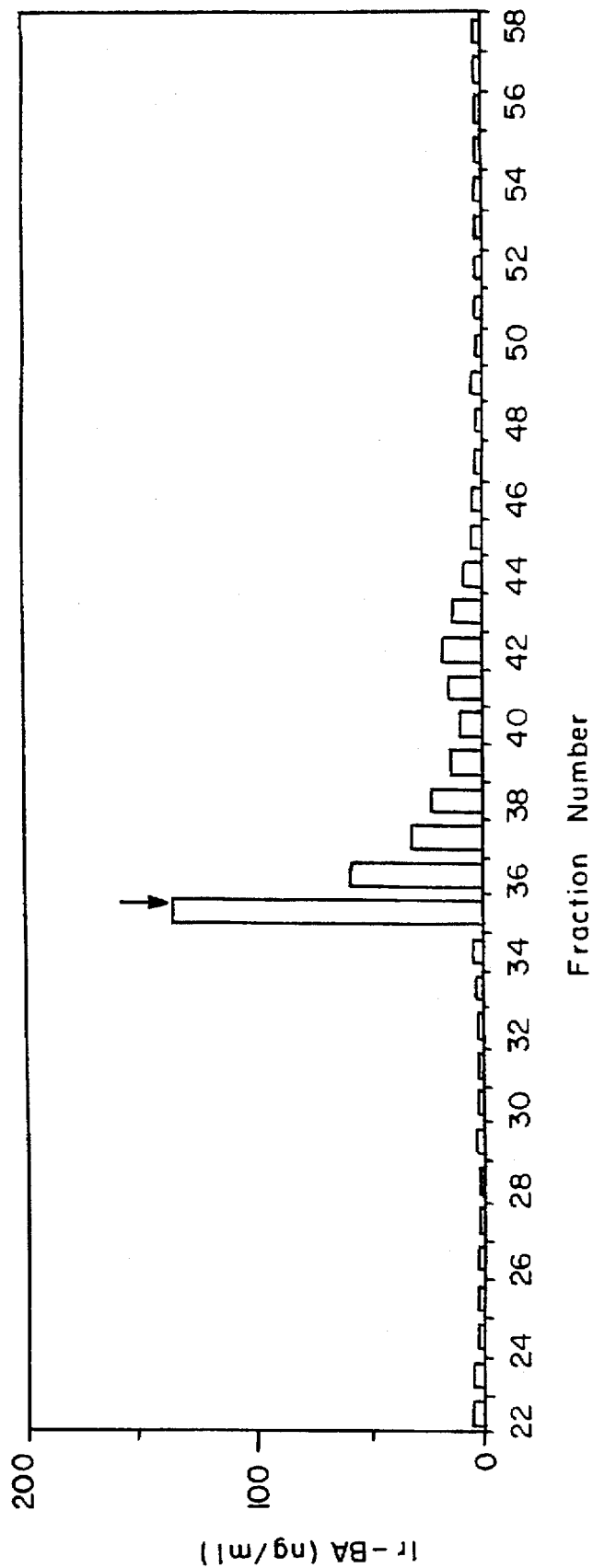
Figure 19C:
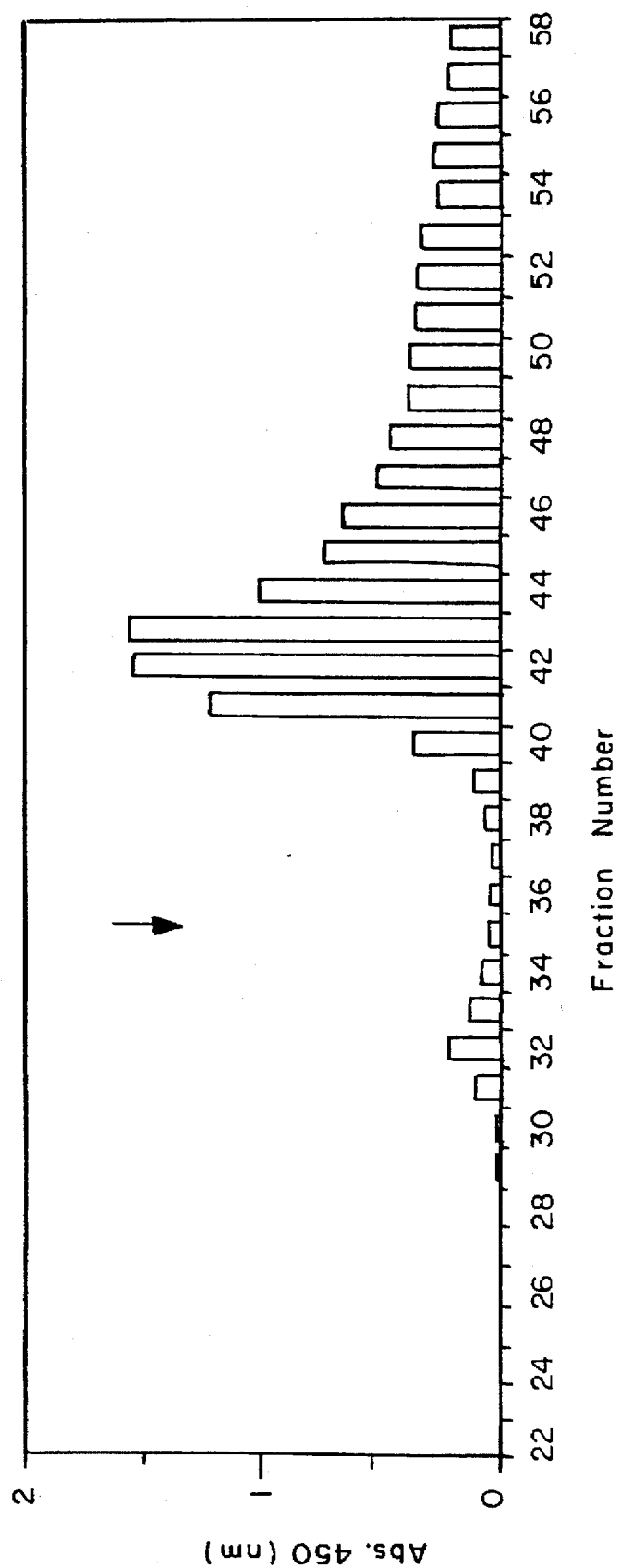

Then, the immunological activity of the eluted fractions was examined by the method described in Example 11 mentioned above. In this case, 3 μl of each of the fractions was used as a sample, and BC-05a-HRP was used as 200-fold dilution. Results are shown in FIG. 19. Both the peaks of No. 35 and Nos. 41–45 were detected in the assay system using BS-85a, the peak of No. 35 was mainly detected in the assay system using BA-27a, and the peak of Nos. 41–45 was detected in the assay system using BC-05a.

The above-mentioned results are based on the specificity of the respective assay systems shown in Example 11, which indicates, together with Example 13, that the assay systems according to the present invention can provide important means for developments of drugs for diagnosis and elucidation of causes of Alzheimer's disease, and prevention and treatment of Alzheimer's disease.

[Example 15] Cloning of Human Type Amyloid Protein Precursor (APP) Gene

β-Amyloids are only parts of a giant precursor protein (APP), and five kinds of cDNAs coding for APP have hitherto been discovered. These cDNAs called APP695, APP714, APP751, APP770 and APP563 are known to be produced from the same APP gene as a result of alternative splicing. Of these, in order to construct plasmid DNA for high expression of human type APP695, a human APP695 gene was cloned.

First, using plasmid pME18s having a strong SRα promoter [*Molecular and Cellular Biology*, 8, 466–472 (1988)] as a vector, a cDNA library of MAC10, human lung cancer cell-derived cells, was prepared. Based on the cDNA nucleotide sequence of human APP already reported, a synthetic DNA having the following sequence upstream from a region coding for the protein (sense):

5'-ATCCCACTCGCACAGCAGCGCACTC-3' (SEQ ID NO:13)

and the following sequence downstream therefrom (antisense):

5'-TGCTGTCCAACTTCAGAGGCTGCTG-3' (SEQ ID NO:14)

were prepared, and using these as a probe, the above-mentioned cDNA library was screened. The resulting cDNA was cloned, and the nucleotide sequence thereof was determined by the synthetic chain termination method. As a result, all were cDNAs coding for APP751. Then, a cDNA library of the human fetal brain prepared using λgt10 as a vector (Stratagene) was screened in a similar manner. As a result, cDNA coding for APP695 was obtained. The cDNA sequence of APP751 completely agreed with that of APP695, except a protease inhibitor region. Accordingly, a plasmid DNA having cDNA of APP751 and a phage DNA having cDNA of APP695 were cleaved and recombined to construct a plasmid DNA in which the cDNA of APP695 was ligated downstream from the SRα promoter.

[Example 16] Breeding of Human APP695 High Expression Rat C6 Glioma Cells

Rat C6 glioma cells (ATCC CCL 107) were cultivated on a culture dish 10 cm in diameter at 37° C. in the presence of 5% $CO_2$, in DMEM containing 10% bovine fetal serum. With 1 µg of plasmid DNA pTB6 [*Cell Structure and Function*, 12, 205–217 (1987)] having a neomycin-resistant gene was mixed 20 µg of plasmid DNA for high expression of human APP695 constructed in Example 15 described above, and the mixture was introduced into C6 glioma cells cultivated to 80% saturation, by calcium phosphate coprecipitation method. After 24 hours, neomycin (GIBCO) was added to give a final concentration of 750 µg/ml, and cultivation was continued to select resistant strains. Each of 18 selected strains thus obtained was suspended in 100 µl of PBS. After lyophilization and ultrasonic treatment, SDS electrophoresis was carried out using 8% polyacrylamide gel. After transcription of the protein to a nitrocellulose membrane, western blot analysis using an anti-human APP mouse monoclonal antibody (Boehringer Mannheim) was carried out to obtain C6–695–18 highest in the expression amount of APP695.

[Example 17] Detection of 3-kDa Peptide Contained in Culture Supernatant of Human APP695 High Expression C6 Glioma Cells In order to identify molecular species of β-amyloids contained in a culture supernatant of the human APP695 high expression C6 glioma cells described in Example 16 mentioned above, the culture supernatant was purified in a manner similar to that of Example 13, and analyzed by the sandwich method-EIA. Namely, 1 liter of the culture supernatant was partially purified by a column filled with BA-27a-Trecyltoyopearl obtained in Example 12 (2) described above, and the resulting eluted fractions were concentrated, followed by fractionation by reverse-phase HPLC using Vydac C4.

Column conditions

Column: Vydac C4 (4.6×250 mm)

Eluents: A (5% acetonitrile containing 0.1% aqueous trifluoroacetic acid)

B (80% acetonitrile containing 0.1% trifluoroacetic acid)

Elution Method: The concentration of eluent B was first increased from 15% to 25% for 5 minutes, and then linearly increased to 25–50% for 60 minutes.

Flow rate: 0.5 ml/minute

Using a 96-well microplate to which BP-90a was solidified, and BA-27a-HRP as a labeled material, according to the method described in Example 9 (1), the above-mentioned reverse-phase HPLC fractions were subjected to the sandwich method-EIA. Fraction No. 28 and Nos. 38–39 in which a high immunological activity was observed were concentrated and subjected to mass spectrometry. As a result, β-amyloid (20–40) or β-amyloid (18–40) was a main constituent for each fraction. The above-mentioned results showed that the sandwich method-EIA using BP-90a and BA-27a could selectively detect derivatives on the C-terminal side of the β-amyloid. This assay system is therefore considered to provide important means when metabolism of APP is studied.

Industrial Applicability

As lesion characteristic of the brains of patients with Alzheimer's disease, deposition of the β-amyloid which is one of the main constituents of senile plaque has been known. By using the monoclonal antibodies of this invention, the β-amyloids having the C-terminal hydrophobic regions can be determined sensitively and specifically, and this determination method is useful for diagnosis of Alzheimer's disease, etc.

What is claimed is:

1. An antibody specifically reactive to a peptide on the C-terminal side of a β-amyloid comprising the amino acid sequence of SEQ ID NO:1, SEQ ID NO:2, SEQ ID NO:3, SEQ ID NO:4, SEQ ID NO:5 or SEQ ID NO:6 or a derivative thereof which is a peptide lacking 1 to 17 amino acid residues from the N-terminal portion of the said β-amyloid, a peptide in which L-aspartic acid of the said β-amyloid is isomerized to L-isoaspartic acid, D-isoaspartic acid or D-aspartic acid, and a peptide in which the N-terminal portion of the said β-amyloid has pyroglutamic acid, and, in which said antibody does not recognize a peptide comprising the amino acid sequence of SEQ ID NO:7.

2. The antibody as claimed in claim 1, which is BA-27a in which said antibody does not recognize a peptide comprising the amino acid sequence of SEQ ID NO:8 and a peptide comprising the amino acid sequence of SEQ ID NO:9.

3. The antibody as claimed in claim 1, in which the said antibody recognizes a peptide comprising the amino acid sequence of SEQ ID NO:8, but does not recognize a peptide comprising the amino acid sequence of SEQ ID NO:9.

4. The antibody as claimed in claim 1, in which said antibody does not recognize a peptide comprising the amino acid sequence of SEQ ID NO:8, but recognizes a peptide comprising the amino acid sequence of SEQ IS NO:9.

5. The antibody as claimed in claim 1, 2, 3 or 4, in which said antibody is a monoclonal antibody.

6. A hybridoma cell producing the monoclonal antibody as claimed in claim 5.

7. A method for determining the presence of a β-amyloid or a derivative thereof in a test solution which comprises contacting said test solution with an antibody as claimed in claim 1, and determining whether said antibody binds a β-amyloid or a derivative thereof in said test solution, wherein said β-amyloid comprises the amino acid sequence of SEQ ID NO:1, SEQ ID NO:2, SEQ ID NO:3, SEQ ID NO:4, SEQ ID NO:5 or SEQ ID NO:6 and said derivative thereof is a peptide lacking 1 to 17 amino acid residues from the N-terminal portion of the said β-amyloid, a peptide in which L-aspartic acid of the said β-amyloid is isomerized to L-isoaspartic acid, D-isoaspartic acid or D-aspartic acid, and a peptide in which the N-terminal portion of the said P-amyloid has pyroglutamic acid.

8. A method for determining the presence of a β-amyloid or a derivative thereof in a test solution which comprises contacting said test solution with an antibody as claimed in claim 1 and (i) a monoclonal antibody designated by BAN-052a secreted by hybridoma NIBH accession number FERM BP-4138 and specifically reactive to a peptide on the N-terminal side of a P-amyloid or a derivative thereof, in which said antibody recognizes a peptide comprising the amino acid sequence of SEQ ID NO:7 and/or a peptide comprising the amino acid sequence of SEQ ID NO:10, or (ii) a monoclonal antibody designated by BAN-50a secreted by hybridoma NIBH accession number FERM BP-4163 and specifically reactive to a peptide on the N-terminal side of a p-amyloid or a derivative thereof, in which said antibody recognizes a peptide comprising the amino acid sequence of SEQ ID NO:7 and/or a peptide comprising the amino acid sequence of SEQ ID NO:10, and determining whether said antibodies bind β-amyloid or a derivative thereof in said solution, wherein said β-amyloid comprises the amino acid sequence of SEQ ID NO:1, SEQ ID NO:2, SEQ ID NO:3, SEQ ID NO:4, SEQ ID NO:5 or SEQ ID NO:6 and said derivative thereof is a peptide lacking 1 to 17 amino acid residues from the N-terminal portion of the said P-amyloid, a peptide in which L-aspartic acid of the said β-amyloid is isomerized to L-isoaspartic acid, D-isoaspartic acid or D-aspartic acid, or a peptide in which the N-terminal portion of the said β-amyloid has pyroglutamic acid.

9. A diagnostic composition for Alzheimer's disease which comprises
 (i) an antibody of claim 1,
 (ii) a monoclonal antibody designated by BAN-052a secreted by hybridoma NIBH accession number FERM BP-4138 and specifically reactive to a peptide on the N-terminal side of a β-amyloid or a derivative thereof, in which said antibody recognizes a peptide comprising the amino acid sequence of SEQ ID NO:7 and/or a peptide comprising the amino acid sequence of SEQ ID NO:10,
 (iii) a monoclonal antibody designated by BAN-50a secreted by hybridoma NIBH accession number FERM BP-4163 and specifically reactive to a peptide on the N-terminal side of a β-amyloid or a derivative thereof, in which said antibody recognizes a peptide comprising the amino acid sequence of SEQ ID NO:7 and/or a peptide comprising the amino acid sequence of SEQ ID NO:10, or
 (iv) an antibody specifically reactive to a p-amyloid or a derivative thereof, in which said antibody does not recognize a peptide comprising the amino acid sequence of SEQ ID NO:7, but recognizes a peptide comprising the amino acid sequence of SEQ ID NO:12, and a labeling substance, wherein said β-amyloid comprises the amino acid sequence of SEQ ID NO:1, SEQ ID NO:2, SEQ ID NO:3, SEQ ID NO:4, SEQ ID NO:5 or SEQ ID NO:6 and said derivative thereof is a peptide lacking 1 to 17 amino acid residues from the N-terminal portion of the said β-amyloid, a peptide in which L-aspartic acid of the said β-amyloid is isomerized to L-isoaspartic acid, D-isoaspartic acid or D-aspartic acid, and a peptide in which the N-terminal portion of the said β-amyloid has pyroglutamic acid.

\* \* \* \* \*